(12) United States Patent
Lipford et al.

(10) Patent No.: US 9,546,168 B2
(45) Date of Patent: Jan. 17, 2017

(54) ERK INHIBITORS

(71) Applicant: Merck Sharp & Dohme Corp., Rahway, NJ (US)

(72) Inventors: Kathryn Lipford, Boston, MA (US); Danielle Falcone, Brookline, MA (US); David L. Sloman, Brookline, MA (US); David J. Witter, Norfolk, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/103,893

(22) PCT Filed: Dec. 12, 2014

(86) PCT No.: PCT/US2014/069873
§ 371 (c)(1),
(2) Date: Jun. 13, 2016

(87) PCT Pub. No.: WO2015/094929
PCT Pub. Date: Jun. 25, 2015

(65) Prior Publication Data
US 2016/0311819 A1    Oct. 27, 2016

Related U.S. Application Data

(60) Provisional application No. 61/917,383, filed on Dec. 18, 2013.

(51) Int. Cl.
*C07D 471/04* (2006.01)
*A61K 31/437* (2006.01)
*A61K 31/444* (2006.01)
*A61K 45/06* (2006.01)

(52) U.S. Cl.
CPC ............ *C07D 471/04* (2013.01); *A61K 31/437* (2013.01); *A61K 31/444* (2013.01); *A61K 45/06* (2013.01)

(58) Field of Classification Search
None
See application file for complete search history.

(56) References Cited

U.S. PATENT DOCUMENTS

| 5,593,997 | A | 1/1997 | Dow et al. |
| 6,171,771 | B1 | 1/2001 | Merkel et al. |
| 8,101,613 | B2 | 1/2012 | Arnold et al. |
| 2015/0258074 | A1* | 9/2015 | Wilson ............... A61K 31/4545 |
| | | | 514/234.2 |
| 2015/0266895 | A1* | 9/2015 | Wilson ................ C07D 519/00 |
| | | | 514/210.18 |

FOREIGN PATENT DOCUMENTS

WO    2013063214 A1    5/2013

* cited by examiner

*Primary Examiner* — Timothy R Rozof
(74) *Attorney, Agent, or Firm* — Catherine D. Fitch; Richard S. Parr

(57) ABSTRACT

Disclosed are the ERK inhibitors of formula (1.0) and the pharmaceutically acceptable salts thereof. Also disclosed are methods of treating cancer using the compounds of formula (1.0). This invention provides compounds that are ERK inhibitors (i.e., ERK2 inhibitors). This invention also provides a pharmaceutical composition comprising an effective amount of at least one (e.g., 1) compound of formula (1.0) and a pharmaceutically acceptable carrier.

15 Claims, No Drawings

ERK INHIBITORS

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (ERK2 activity), which small-molecules would be useful for treating a broad spectrum of cancers, such as, for example, melanoma, pancreatic cancer, thryroid cancer, colorectal cancer, lung cancer, breast cancer, and ovarian cancer. Such a contribution is provided by this invention.

SUMMARY OF THE INVENTION

This invention provides compounds that inhibit the activity of of ERK2.

Thus, this invention provides compounds that are ERK inhibitors (i.e., ERK2 inhibitors), said compounds being of the formula (1.0):

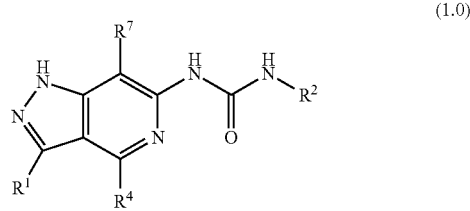

(1.0)

or the pharmaceutically acceptable salts, esters, solvates, and prodrugs thereof, wherein $R^1$, $R^2$, $R^4$, and $R^7$ are defined below.

This invention provides: (1) compounds of formula (1.0); (2) compounds of formula (1.0) in pure or isolated form; (3) pharmaceutically acceptable salts of the compounds of formula (1.0); (4) solvates of the compounds of formula (1.0); (5) compounds of formula (1.0) wherein from one to all of the hydrogens are deuterium; (6) compounds of formula (1.0) wherein at least one H is deuterium; (7) compounds of formula (1.0) wherein 1 to 5 H are deuterium; (8) compounds of formula (1.0) wherein 1 to 2 H are deuterium; and (9) compounds of formula (1.0) wherein one H is deuterium.

This invention also provides the final compounds of Examples 1 to 29.

This invention also provides a pharmaceutical composition comprising an effective amount of at least one (e.g., 1) compound of formula (1.0) and a pharmaceutically acceptable carrier. This invention also provides a pharmaceutical composition comprising an effective amount of at least one (e.g., 1) compound of formula (1.0) and an effective amount of at least one (e.g., 1) other pharmaceutically active ingredient (such as, for example, a chemotherapeutic agent), and a pharmaceutically acceptable carrier.

This invention also provides a method of inhibiting ERK (i.e., inhibiting the activity of ERK2) in a patient in need of such treatment comprising administering to said patient an effective amount of at least one (e.g., 1) compound of formula (1.0).

This invention also provides a method for treating cancer in a patient in need of such treatment, said method comprising administering to said patient an effective amount of at least one (e.g., 1) compound of formula (1.0). This invention also provides a method for treating cancer in a patient in need of such treatment, said method comprising administering to said patient an effective amount of at least one (e.g., 1) compound of formula (1.0), in combination with an effective amount of at least one chemotherapeutic agent. The methods of this invention include the administration of a pharmaceutical composition comprising at least one (e.g., 1) compound of this invention and a pharmaceutically acceptable carrier. This invention also provides any of the above methods of treating cancer wherein the cancer is colorectal. This invention also provides any of the above methods of treating cancer wherein the cancer is melanoma.

The methods of treating cancers described herein can optionally include the administration of an effective amount of radiation (i.e., the methods of treating cancers described herein optionally include the administration of radiation therapy).

DETAILED DESCRIPTION OF THE INVENTION

All patents, publications and pending patent applications identified herein are hereby incorporated by reference.

As described herein, unless otherwise indicated, the use of a drug or compound in a specified period is per treatment cycle. For example, once a day means once per day of each day of the treatment cycle, and once a week means one time per week during the treatment cycle.

The following abbreviations have the following meanings unless defined otherwise: ACN is acetonitrile, BAST is bis(2-methoxyethyl)aminosulfur trifluoride; Bn is benzyl; Brettphos is 2-(Dicyclohexylphosphino)3,6-dimethoxy-2', 4',6'-triisopropyl-1,1'-biphenyl; Brettphos PreCatalyst is BrettPhos palladium(II) phenethylamine chloride; CBZ is carboxybenzyl; Cy is cyclohexyl; DBU is 1,8-Diazabicyclo [5.4.0]undec-7-ene; DCE is dichloroethane; DCM is dichloromethane; DIBAL-H is diisobutylaluminum hydride; DIPEA is diisopropylethylamine; DMA is dimethylacetamide; DMAP is 4-dimethylaminopyridine, DMF is dimethylformamide; DMSO is dimethyl sulfoxide; DPPA is diphenylphosphoryl azide; EtOAc is ethyl acetate; EtOH is ethanol; PdCl$_2$(dppf)-CH$_2$Cl$_2$ is [1,1'-Bis(diphenylphosphino)ferrocene]dichloropalladium(II), complex with dichloromethane; MeOH is methanol; Mes-Cl is methanesulfonyl chloride; NaHMDS is sodium bis(trimethylsilyl)amide; NBS is N-bromosuccinimide; PS-HCO$_3$ cartridge is bicarbonate polystyrene copolymere, anion exchanger cartridge; Rochelle salt is sodium potassium tartarate; RT is room temperature; SFC is Supercritcal fluid chromatography; t-BuOH is tert-butanol; TEA is triethylamine; TFA is trifluoroacetic acid; THF is tetrahydrofuran; TRCl is triphenyl methane chloride; and TRT is trityl or triphenylmethane.

As used herein, unless otherwise specified, the terms below have the meaning indicated.

The term "composition" is intended to encompass a product comprising the specified ingredients in the specified amounts, as well as any product which results, directly or indirectly, from combination of the specified ingredients in the specified amounts.

The term "anti-cancer agent" means a drug (medicament or pharmaceutically active ingredient) for treating cancer.

The term "antineoplastic agent" means a drug (medicament or pharmaceutically active ingredient) for treating cancer (i.e., a chemotherapeutic agent).

The term "at least one" means one or more than one. In one example "at least one" means 1-4, and in another example 1-3, and in another example 1-2, and in another example 1. The meaning of "at least one" with reference to the number of compounds of this invention is independent of the meaning with reference to the number of chemotherapeutic agents.

The term "chemotherapeutic agent" means a drug (medicament or pharmaceutically active ingredient) for treating cancer (i.e., and antineoplastic agent);

The term "compound" with reference to the antineoplastic agents, includes the agents that are antibodies.

The term "consecutively" means one following the other.

The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the ERK inhibitor (i.e., a compound of this invention) is that amount which results in the reduction in ERK (ERK2) activity and phosphorylation. The reduction in ERK activity may be determined by the analysis of pharmacodynamic markers such as phosphorylated RSK1,2 using techniques well known in the art.

The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

The term "one or more" has the same meaning as "at least one".

The term "patient" means an animal, such as a mammal (e.g., a human being, and preferably a human being).

The term sequentially-represents (1) administration of one component of the method ((a) compound of the invention, or (b) chemotherapeutic agent, signal transduction inhibitor and/or radiation therapy) followed by administration of the other component or components. After administration of one component, the next component can be administered substantially immediately after the first component, or the next component can be administered after an effective time period after the first component. The effective time period is the amount of time given for realization of maximum benefit from the administration of the first component.

The term "solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like; "hydrate" is a solvate wherein the solvent molecule is H$_2$O.

The term "fused" with reference to, for example, two fused rings, means that the two rings have two atoms in common.

The term "monocyclic", as used to describe a ring, means the ring is a single ring (i.e., the ring is not a fused ring). Thus, for example, a "monocyclic heteroaryl ring" means a single heteroaryl ring. A bridged monocyclic ring means a monocyclic ring wherein two atoms in the ring are connected by a bridge. Thus, for example, a "bridged monocyclic heterocycloalkyl ring" means a monocyclic heterocycloalkyl ring wherein two atoms in the ring are connected by a bridge.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, unless otherwise specified, the terms below have the meanings indicated, and unless otherwise specified, the definitions of each term (i.e., moiety or substituent) apply when that term is used individually or as a component of another term (e.g., the definition of aryl is the same for aryl and for the aryl portion of arylheterocycloalkyl, and the like).

The term "alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; non-limiting examples of suitable alkenyl groups include ethenyl, propenyl, n-butenyl, 3-methylbut-2-enyl, n-pentenyl, octenyl and decenyl.

The term "alkoxy" means an alkyl-O— group (i.e., the bond to the parent moiety is through the ether oxygen) in which the alkyl group is as defined below. Non-limiting examples of suitable alkoxy groups include methoxy, ethoxy, n-propoxy, isopropoxy, n-butoxy and heptoxy.

The term "alkyl" (including the alkyl portions of other moieties, such as alkoxy) means an aliphatic hydrocarbon group (chain) that can be straight or branched wherein said group comprises about 1 to about 20 carbon atoms in the chain. In one example said alkyl group comprises about 1 to about 12 carbon atoms in the chain, in another example about 1 to about 6 carbon atoms in the chain; in another example 1 to about 4 carbon atoms in the chain; and in another example 1 to about 2 carbon atoms in the chain. Branched alkyl means that one or more lower alkyl groups, such as methyl, ethyl or propyl, are attached to a linear alkyl chain. "Lower alkyl" means a group comprising about 1 to about 6 carbon atoms in the chain, and said chain can be straight or branched.

The term "alkylene" (including the alkylene portions of other moieties, such as -alkylene-aryl) means a chain comprising at least one —(CH$_2$)— group. Examples of alkylene chains include, but are not limited to: —(CH$_2$)$_{1-6}$—, —(CH$_2$)$_{1-4}$—, —(CH$_2$)$_{1-2}$— and —(CH$_2$)—.

The term "amino" means an —NH$_2$ group.

The term "aryl" (sometimes abbreviated "ar") (including the aryl portion of fused heteroarylaryl and fused arylheterocycloalkyl) means an aromatic monocyclic or multicyclic ring system comprising about 6 to about 14 carbon atoms, preferably about 6 to about 10 carbon atoms. Non-limiting examples of suitable aryl groups include phenyl and naphthyl.

The term "arylalkyl" (or aralkyl) means an aryl-alkyl-group (i.e., the bond to the parent moiety is through the alkyl group) wherein the aryl and alkyl moieties are as defined above; preferred arylalkyls comprise a lower alkyl group; non-limiting examples of suitable aralkyl groups include benzyl, 2-phenethyl and naphthalenylmethyl.

The term "cycloalkyl" means a non-aromatic mono- or multicyclic ring system comprising about 3 to about 7 carbon atoms, preferably about 3 to about 6 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

The term "cycloalkylalkyl" means a cycloalkyl-alkyl-group (i.e., the bond to the parent moiety is through the alkyl group) wherein the cycloalkyl and alkyl moieties are as defined above.

The term "cycloalkylalkenyl" means a cycloalkyl-alkenyl-group (i.e., the bond to the parent moiety is through the alkenyl group) wherein the cycloalkyl and alkenyl moieties are as defined above.

The term "halo" means fluoro, chloro, bromo, or iodo groups. Preferred halos are fluoro, chloro or bromo, and more preferred are fluoro and chloro.

The term "halogen" means fluorine, chlorine, bromine, or iodine. Preferred halogens are fluorine, chlorine and bromine.

The term "heteroaryl" means an aromatic monocyclic or multicyclic ring system (e.g., a fused ring system) comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls comprise about 5 to about 6 ring atoms. The prefix aza, oxa or thia before the heteroaryl root name means that at least a nitrogen, oxygen or sulfur atom, respectively, is present as a ring atom. A nitrogen atom of a heteroaryl can be optionally oxidized to the corresponding N-oxide. The heteroaryl multicyclic ring system includes two rings fused together (i.e., there are two atoms common to both rings). Examples of the heteroaryl multicyclic ring system include fused heteroarylaryl rings (i.e., a heteroaryl ring fused to an aryl ring), and fused heteroarylheteroaryl rings (i.e., a heteroaryl ring fused to a heteroaryl ring). Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, benzopyrazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine

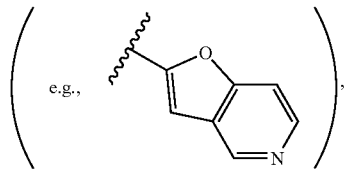

and the like.

The term "heteroarylalkyl" (or heteroaralkyl) means a heteroaryl-alkyl-group (i.e., the bond to the parent moiety is through the alkyl group) in which the heteroaryl and alkyl moieties are as defined above; preferred heteroarylalkyls comprise an alkyl group that is a lower alkyl group; non-limiting examples of suitable aralkyl groups include pyridyl-CH$_2$—, pyrimidinyl-CH$_2$—, imidazolyl-CH$_2$; pyrazinyl-CH$_2$—, and thiazolyl-CH$_2$—.

The term "fused heteroarylaryl" means a monocyclic heteroaryl ring fused to an aryl ring (i.e., the heteroaryl ring and the aryl ring have two atoms in common).

The term "heterocycloalkenyl" (or "heterocyclenyl") means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom, respectively, is present as a ring atom. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. A non-limiting example of a suitable multicyclic oxaheterocyclenyl group is 7-oxabicyclo

[2.2.1]heptenyl; non-limiting examples of suitable monocyclic thiaheterocyclenyl rings include dihydrothiophenyl, dihydrothiopyranyl, and the like.

The term "heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. The heterocycloalkyl rings of this invention can be "bridged heterocycloalkyl" rings. The term "bridged heterocycloalkyl"" (or "bridged heterocyclyl") means a heterocycloalkyl group as defined above having an alkylene chain (generally a 1 or 2 carbon alkylene chain, not counting the atoms in the ring to which the alkylene chain is bound to) bridging two carbon atoms in the ring.

Any carbon or heteroatom with unsatisfied valences in the text, schemes, examples, structural formulae, and any tables herein is assumed to have the hydrogen atom or atoms to satisfy the valences. And any one or more of these hydrogen atoms can be deuterium.

Those skilled the art will appreciate that formulas showing a bond that does not have a substituent at the end of the bond represents a methyl group. Thus, for example,

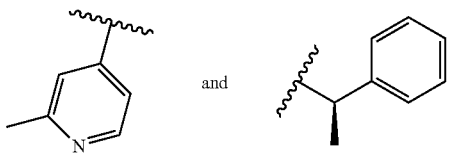

are the same moieties as:

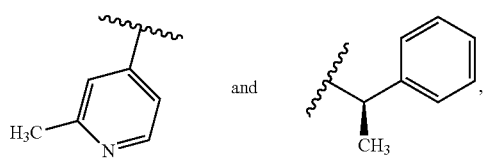

respectively.

One or more compounds of the invention may also exist as, or be optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

The compounds of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. Also, for example, all keto-enol and imine-enamine forms of the compounds are included in the invention.

Tautomeric forms such as, for example, the moieties:

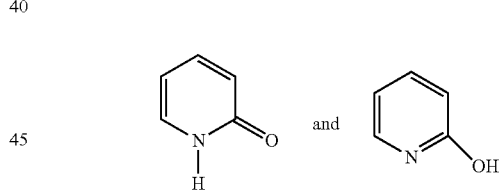

are considered equivalent in certain examples of this invention.

Thus, all stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (1) may be atropisomers and are considered as part of this invention. Enantiomers can also be separated by use of chiral HPLC column.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula (1) or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

This invention also includes the compounds of this invention in isolated and purified form.

Polymorphic forms of the compounds of formula (1), and of the salts, solvates and prodrugs of the compounds of formula (1), are intended to be included in the present invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.,* 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

All such acid and base salts are intended to be pharmaceutically acceptable salts within the scope of the invention and all acid and base salts are considered equivalent to the free forms of the corresponding compounds for purposes of the invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

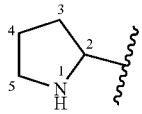

there is no —OH attached directly to carbons marked 2 and 5.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{123}I$, respectively. Certain isotopically-labelled compounds of formula (1) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (1) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

This invention provides compounds of formula (1.0):

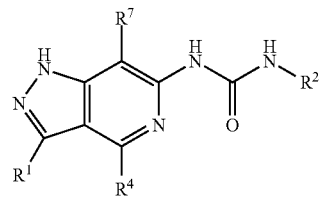

(1.0)

or a pharmaceutically acceptable salt thereof, wherein:

$R^1$ is selected from the group consisting of: H, halo, —CN, $(C_1-C_6)$alkyl, substituted $(C_1-C_6)$alkyl, $(C_2-C_6)$alkenyl, $(C_3-C_6)$cycloalkyl, substituted $(C_3-C_6)$cycloalkyl, heteroaryl, substituted heteroaryl, heterocycloalkenyl-, substituted heterocycloalkenyl, —$(C_1-C_6)$alkyl-O—$(C_1-C_6)$alkyl, —$(C_1-C_6)$alkyl-O-(substituted $(C_1-C_6)$ alkyl), -(substituted $(C_1-C_6)$alkyl)-O-(substituted $(C_1-C_6)$ alkyl), -(substituted $(C_1-C_6)$alkyl)-O—$(C_1-C_6)$ alkyl), aryl, substituted aryl, —C(O)($C_1-C_6$alkyl), —C(O)(substituted $(C_1-C_6)$alkyl), —C(O)O($C_1-C_6$)alkyl, —C(O)NH($C_1-C_6$)alkyl, —C(O)N(($C_1-C_6$)alkyl)$_2$ wherein each alkyl is independently selected, —C(O)—$(C_1-C_6)$alkyl-C(O)—$(C_1-C_6)$alkyl, —$(C_1-C_4)$alkyl-C(O)—O—$(C_1-C_4)$alkyl, —C(O)NH($C_1$-$C_2$)alkyl-fused heteroarylheteroaryl, —C(O)NH($C_1$-$C_2$)alkyl-(substituted fused heteroarylheteroaryl), —C(O)NH($C_1$-$C_2$)alkyl-($C_3$-$C_6$)cycloalkyl-N($R^8$)$_2$, —C(O)NH($C_1$-$C_2$)alkyl-(substituted $(C_3$-$C_6)$cycloalkyl)-N($R^8$)$_2$, —C(O)NH($C_1$-$C_2$)alkylheterocycloalkyl, —C(O)NH—($C_1$-$C_2$)alkyl (substituted heterocycloalkyl), —C(O)NH($C_1$-$C_2$)alkylheteroaryl, —C(O)NH—($C_1$-$C_2$)alkyl(substituted heteroaryl), —C(O)NH($C_1$-$C_6$)alkyl-($C_3$-$C_6$)cycloalkyl, —C(O)NH—($C_1$-$C_6$)alkyl-(substituted $(C_3$-$C_6$)cycloalkyl), —C(O)NH($C_1$-$C_6$)alkyl-O—$(C_1$-$C_6$)alkyl, —C(O)NH—($C_1$-$C_6$)alkylheterocycloalkyl, —C(O)NH($C_1$-$C_6$)alkyl(substituted heterocycloalkyl), —C(O)NH—($C_1$-$C_2$)-(bridged multicyclic cycloalkyl) (e.g., —C(O)NH—($C_1$-$C_2$)-(bridged tricyclic cycloalkyl), —C(O)NH—($C_1$-$C_2$)-(substituted bridged multicyclic cycloalkyl) (e.g., —C(O)NH—($C_1$-$C_2$)-(substituted bridged tricyclic cycloalkyl), —C(O)-heterocycloalkyl-S—($C_1$-$C_6$)alkyl, —C(O)-(substituted heterocycloalkyl-S—($C_1$-$C_6$)alkyl, —C(O)-heterocycloalkyl, —C(O)-(substituted heterocycloalkyl), fused arylheteroaryl, fused (substituted arylheteroaryl), fused heteroarylheteroaryl, fused (substituted heteroarylheteroaryl), —($C_1$-$C_4$)alkyl-S(O)$_2$—$(C_1$-$C_6$)alkyl, and —$(C_1$-$C_4$)alkyl-NH—($C_1$-$C_6$)alkyl;

and wherein said substituted $R^1$ groups, other than said substituted $(C_1-C_6)$alkyl, are substituted with 1 to 3 substituents independently selected from the group consisting of: —$(C_1-C_6)$alkyl, —$(C_1-C_6)$alkoxy, halo, CN, —OH, —CF$_3$, =O, —NH$_2$, —NH($C_1-C_6$)alkyl, —S(O)$_2$($C_1-C_6$) alkyl, —($C_3-C_6$)cycloalkyl, —(($C_1-C_6$)alkyl)OH, —($C_3-C_6$) cycloalkyl-S—($C_3-C_6$)cycloalkyl, —N(($C_1-C_6$)alkyl)$_2$ wherein each alkyl is independently selected, —C(O)O—($C_1-C_6$)alkyl, —C(O)OH, —OCF$_3$, —C(O)NH($C_1-C_6$) alkyl, heteroaryl, —($C_1-C_6$)alkyl)-O—($C_1-C_6$)alkyl, fused heteroarylaryl-, heterocycloalkyl, and heterocycloalkenyl;

and wherein the substituted $(C_1-C_6)$alkyl $R^1$ group, and the substituted $(C_1-C_6)$alkyl moieties of the substituted $R^1$ groups comprising said substituted $(C_1-C_6)$alkyl moieties, are substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

$R^2$ is selected from the group consisting of: H, ($C_6$-$C_{10}$) aryl-($C_1$-$C_4$alkyl)-heterocyclo alkyl-, —($C_1$-$C_6$ alkyl), —($C_1$-$C_6$ alkyl)-O—($C_1$-$C_6$ alkyl), —($C_1$-$C_6$ alkyl)-heterocycloalkyl-($C_6$-$C_{10}$ aryl), ($C_1$-$C_4$alkyl)($C_6$-$C_{10}$)aryl, —($C_1$-$C_3$alkyl)heteroaryl, —($C_3$-$C_6$ cycloalkyl)-($C_6$-$C_{10}$aryl), -heterocycloalkyl-($C_6$-$C_{10}$aryl); and wherein said aryl, heterocycloalkyl, heteroaryl, and cycloalkyl moieties of said $R^2$ groups are optionally substituted with 1-3 substituents independently selected from the group consisting of: halo (e.g., F, Br, and Cl), —O—($C_1$-$C_6$alkyl), —OH, —$CF_3$, and —($C_1$-$C_6$alkyl); and wherein said alkyl moieties of said $R^2$ groups are optionally substituted with 1-3 substituents independently selected from the group consisting of: halo (e.g., F, Br, and Cl), —O—($C_1$-$C_6$alkyl), —O-(substituted $C_1$-$C_6$alkyl), —OH and —$CF_3$, and wherein said substituted $C_1$-$C_6$alkyl moiety of said —O-(substituted $C_1$-$C_6$alkyl) group is substituted with 1-3 independently selected halo atoms;

$R^3$ is selected from the group consisting of: H, ($C_1$-$C_6$) alkyl, or substituted ($C_1$-$C_6$)alkyl, wherein said substituted ($C_1$-$C_6$)alkyl is substituted with 1 to 3 substituents independently selected from the group consisting of: —($C_1$-$C_6$) alkoxy, halo, CN, —OH, =O, —$CF_3$, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

$R^4$ is selected from the group consisting of: —$NHR^3$, —$OR^5$, —CH(OH)$R^6$, halo, —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)$_2$ wherein each alkyl is independently selected, and —($C_1$-$C_6$alkyl)-heterocycloalkyl;

$R^5$ is selected from the group consisting of: H, —($C_1$-$C_6$alkyl), and -(substituted $C_1$-$C_6$alkyl), wherein said substituted alkyl is substituted with 1 to 3 substituents independently selected from the group consisting of: —($C_1$-$C_6$) alkoxy, halo, CN, —OH, =O, —$CF_3$, —$NH_2$, —NH($C_1$-$C_6$)alkyl, —S(O)$_2$($C_1$-$C_6$)alkyl, fused heteroarylaryl-, heterocycloalkyl, and heterocycloalkenyl;

$R^6$ is selected from the group consisting of: —($C_1$-$C_6$alkyl) and —($C_3$-$C_6$ cycloalkyl);

$R^7$ is selected from the group consisting of: H, halo, —($C_1$ to $C_6$alkyl), —($C_3$-$C_6$ cycloalkyl), hydroxy substituted —($C_1$-$C_6$alkyl); and each $R^8$ is independently selected from —($C_1$-$C_6$)alkyl.

Examples of the substituted ($C_1$-$C_6$)alkyl $R^1$ substitutent include ($C_1$-$C_6$)alkyl substituted with 1 to 3 independently selected halo atoms. In one example the substituted ($C_1$-$C_6$) alkyl $R^1$ group is a ($C_1$-$C_6$)alkyl substituted with 1 to 3 F atoms. In another example the ($C_1$-$C_6$)alkyl $R^1$ group is a ($C_1$-$C_2$)alkyl substituted with 1 to 3 F atoms. In another example the ($C_1$-$C_6$)alkyl $R^1$ group is —$CHF_2$, and in another example —$CH_2F$, and in another example —$CF_3$.

In one example the —C(O)($C_1$-$C_6$alkyl) $R^1$ substitutent is —C(O)($C_1$-$C_4$alkyl), and in another example —C(O)($C_1$-$C_2$alkyl), and in another example —C(O)$CH_3$.

In one example the substituted ($C_1$-$C_6$)alkyl $R^1$ substitutent is ($C_1$-$C_6$)alkyl substituted with —OH, and in another example —$CH_2$OH, and in another example —CH($CH_3$)OH.

In one example the $R^1$ heteroaryl substitutent is pyridyl.

Examples of the of the $R^1$ heteroaryl group, and the heteroaryl moiety in the $R^1$ groups comprising a heteroaryl moiety, and the heteroaryl group that is a substituent on a substituted $R^1$ group include, but are not limited to: pyridyl, imidazolyl, thiazolyl, pyrimidinyl, pyrazinyl, pyrrolyl, oxazolyl, and triazinyl. Examples of the of the $R^1$ heteroaryl group, and the heteroaryl moiety in the $R^1$ groups comprising a heteroaryl moiety include, but are not limited to: substituted pyridyl, substituted imidazolyl, substituted thiazolyl, substituted pyrimidinyl, substituted pyrazinyl, substituted pyrrolyl, substituted oxazolyl, and substituted triazinyl.

Examples of the of the $R^1$ heteroaryl group, and the heteroaryl moiety in the $R^1$ groups comprising a heteroaryl moiety, and the heteroaryl group that is a substituent on a substituted $R^1$ group also include fused ring systems (fused ring heteroaryls), such as, for example, benzopyrazolyl, benzothiazolyl and benzoimidazolyl. Examples of the of the $R^1$ heteroaryl group, and the heteroaryl moiety in the $R^1$ groups comprising a heteroaryl moiety also include substituted fused ring systems (fused ring heteroaryls), such as, for example, substituted benzopyrazolyl, substituted benzothiazolyl and substituted benzoimidazolyl.

Examples of the substituted heteroaryl $R^1$ substituent include, but are not limited to, substituted pyridyl. In one example the substituted heteroaryl $R^1$ substitutent is pyridyl substituted with a halo atom, and in another example pyridyl substituted with F, and in another example pyridyl substituted with a $C_1$-$C_6$alkyl group, and in another example pyridyl substituted with methyl, and in another example pyridyl substituted with —CN.

In one example the ($C_3$-$C_6$)cycloalkyl $R^1$ substituent is cyclopropyl.

In one example the substituted aryl $R^1$ substituent is phenyl substituted with 1-3 independently selected halo atoms, and in another example phenyl substituted with one halo atom, and in another example phenyl substituted with F, and in another example phenyl substituted with CN.

Examples of $R^1$ include, but are not limited to: methylpyridyl, fluoropyridyl, —$CF_3$—C(O)$CH_3$, —$CH_2$OH, cyclopropyl, —$CHF_2$, —CH(OH)$CH_3$, fluorophenyl, cyanopyridyl, and cyanophenyl.

Examples of the methylpyridyl, fluoropyridyl, fluorophenyl, cyanopyridyl and cyanophenyl $R^1$ groups include, but are not limited to:

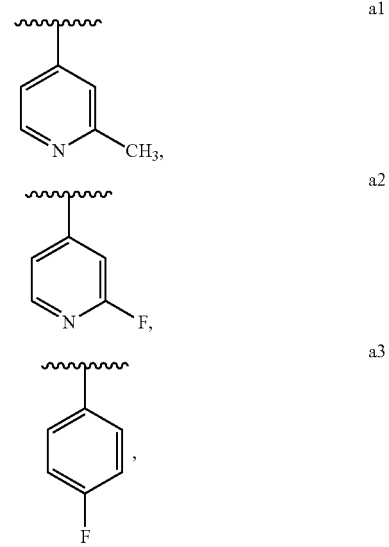

a4

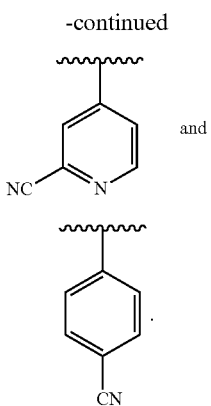

and a5

Thus, in one example $R^1$ is methylpyridyl; in another example $R^1$ is a1; in another example $R^1$ is fluoropyridyl; in another example $R^1$ is a2; in another example $R^1$ is —$CF_3$; in another example $R^1$ is —$C(O)CH_3$; in another example $R^1$ is —$CH_2OH$; in another example $R^1$ is cyclopropyl; in another example $R^1$ is —$CH_2F$; in another example $R^1$ is —$CH(OH)CH_3$; in another example $R^1$ is fluorophenyl; in another example $R^1$ is a3; in another example $R^1$ is cyanopyridyl; in another example $R^1$ is a4; in another example $R^1$ is cyanophenyl; and in another example $R^1$ is a5.

In one example $R^2$ is H.

Examples of the independently selected substitutents that are on the $R^2$ substituted groups (i.e., the groups that the substituted $R^2$ moiety is substituted with) include but are not limited to: halo, such as, for example: F and Cl; ($C_1$ to $C_6$)alkyl, such as, for example: ($C_1$ to $C_3$)alkyl, and ($C_1$-$C_2$) alkyl; and —O—($C_1$-$C_6$)alkyl, such as, for example; —O—($C_1$-$C_4$)alkyl, and in another example —O—($C_1$-$C_3$)alkyl, and in another example, —$OCH_3$).

Examples of the substituents on the substituted aryl, substituted heterocycloalkyl, substituted heteroaryl, and substituted cycloalkyl $R^2$ groups include, for example, halo —O—($C_1$-$C_4$)alkyl, —O—($C_1$-$C_2$)alkyl), and —OH.

In another example $R^2$ is a —($C_1$-$C_6$)alkyl, such as, for example: (i) a ($C_1$-$C_4$)alkyl, (ii) a ($C_1$-$C_3$)alkyl, and (iii) a ($C_1$-$C_2$)alkyl, and (iv) in one example methyl.

Examples of $R^2$ also include the substituted —($C_1$-$C_6$) alkyl moiety substituted with 1 to 3 substitutents independently selected from the group consisting of: halo, —O—($C_1$-$C_6$)alkyl (e.g., —O—($C_1$-$C_4$)alkyl, and —O—($C_1$-$C_2$) alkyl), and —OH.

In another example $R^2$ is a —($C_1$-$C_6$)alkyl-O—($C_1$-$C_6$) alkyl, such as, for example —($C_1$-$C_3$)alkyl-O—($C_1$-$C_2$) alkyl, such as, for example: a —$CH_2CH_2OCH_3$.

Examples of the optional —O-(substituted $C_1$-$C_6$alkyl) moiety on an alkyl moiety of an $R^2$ group include, but are not limited to, —O-(substituted $C_1$-$C_2$alkyl). In one example said —O-(substituted $C_1$-$C_6$alkyl) moiety is a —O-(substituted $C_1$-$C_6$alkyl) substituted with 1-3 F atoms, and in another example an —O-(substituted $C_1$-$C_2$alkyl) substituted with 1-3 F atoms, and in another example an —O-(substituted $C_1$-$C_2$alkyl) substituted with 1-2 F atoms, and in another example an —O-(substituted $C_1$-$C_2$alkyl) substituted with 2 F atoms, and in another example —$OCHF_2$.

Examples of the of the $R^2$ heteroaryl moiety in the $R^2$ groups comprising a heteroaryl moiety include, but are not limited to: pyridyl, imidazolyl, thiazolyl, pyrimidinyl, pyrazinyl, pyrrolyl, oxazolyl, and triazinyl. Examples of the substituted heteroaryl moiety in the $R^2$ groups comprising a substituted heteroaryl moiety include, but are not limited to: substituted pyridyl, substituted imidazolyl, substituted thiazolyl, substituted pyrimidinyl, substituted pyrazinyl, substituted pyrrolyl, substituted oxazolyl, and substituted triazinyl.

Examples of the heteroaryl moiety in the $R^2$ groups comprising a heteroaryl moiety also include fused ring systems (fused ring heteroaryls), such as, for example, benzopyrazolyl, benzothiazolyl and benzoimidazolyl. Examples of the substituted heteroaryl moiety in the $R^2$ groups comprising a substituted heteroaryl moiety also include substituted fused ring systems (fused ring heteroaryls), such as, for example, substituted benzopyrazolyl, substituted benzothiazolyl and substituted benzoimidazolyl.

Examples of $R^2$ also include the substituted —($C_1$-$C_3$alkyl)heteroaryl-moieties substituted with 1 to 3 substitutents independently selected from the group consisting of: halo, —($C_1$-$C_6$)alkoxy (e.g., —($C_1$-$C_4$)alkoxy, and —($C_1$-$C_2$)alkoxy), and —OH.

Examples of $R^2$ also include the substituted ($C_6$-$C_{10}$)aryl-($C_1$-$C_4$alkyl)-moieties substituted with 1 to 3 substitutents independently selected from the group consisting of: halo, —($C_1$-$C_6$)alkoxy (e.g., —($C_1$-$C_4$)alkoxy, and —($C_1$-$C_2$) alkoxy), and —OH.

In one example $R^2$ is a ($C_6$-$C_{10}$)aryl-($C_1$-$C_4$alkyl)-, and in another example phenyl-($C_1$-$C_4$alkyl)-, and in another example phenyl-($C_1$-$C_3$alkyl)-, and in another example phenyl-($C_1$-$C_2$alkyl)-.

In another example $R^2$ is a ($C_6$-$C_{10}$)aryl-($C_1$-$C_4$alkyl)- wherein said $C_1$-$C_4$alkyl moiety is substituted, and in another example a phenyl-($C_1$-$C_4$alkyl)- wherein said $C_1$-$C_4$alkyl moiety is substituted, and in another example a phenyl-($C_1$-$C_4$alkyl)- wherein said $C_1$-$C_4$alkyl is substituted with —OH, and in another example a phenyl-($C_1$-$C_4$alkyl)- wherein said $C_1$-$C_4$alkyl is substituted with —O-(substituted $C_1$-$C_2$alkyl), and in another example a phenyl-($C_1$-$C_4$alkyl)- wherein said $C_1$-$C_4$alkyl is substituted with —OCHF.

In one example $R^2$ is ($C_6$-$C_{10}$)aryl-($C_1$-$C_4$alkyl)- wherein the aryl moiety is substituted and the alkyl moiety is unsubstituted. In another example $R^2$ is ($C_6$-$C_{10}$)aryl-($C_1$-$C_4$alkyl)- wherein the aryl moiety is substituted and the alkyl moiety is substituted. In another example $R^2$ is ($C_6$-$C_{10}$) aryl-($C_1$-$C_4$alkyl)- wherein the aryl moiety is substituted with 1-3 independently selected halo atoms (e.g., F, and in one example one F) and the alkyl moiety is unsubstituted. In another example $R^2$ is ($C_6$-$C_{10}$)aryl-($C_1$-$C_4$alkyl)- wherein the the aryl moiety is substituted with 1-3 independently halo atoms (e.g., F, and in one example one F) and the alkyl moiety is substituted with —OH. In another example $R^2$ is ($C_6$-$C_{10}$)aryl-($C_1$-$C_4$alkyl)- wherein the the aryl moiety is substituted with 1-3 independently halo atoms (e.g., F, and in one example one F) and the alkyl moiety is substituted with —O-(substituted $C_1$-$C_2$alkyl) (e.g., —$OCHF_2$).

Examples of $R^2$ include but are not limited to, —$CH(CH_3)$ phenyl, —$CH(CH_2OCHF_2)$-phenyl, —$CHC(CH_3)_2OH$-phenyl, —$CHC(CH_3)_2OH$—F-phenyl, —$CHC(CH_3)_2OH$-phenyl, —$CHCH(CH_3)(OH)$—F-phenyl, —$CHCH(CH_3)$(OH)-phenyl, and —$CHC(CH_3)_2OH$-phenyl.

In one example, $R^2$ is selected from the group consisting of:

b1

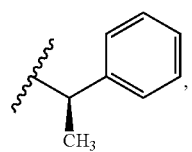

,

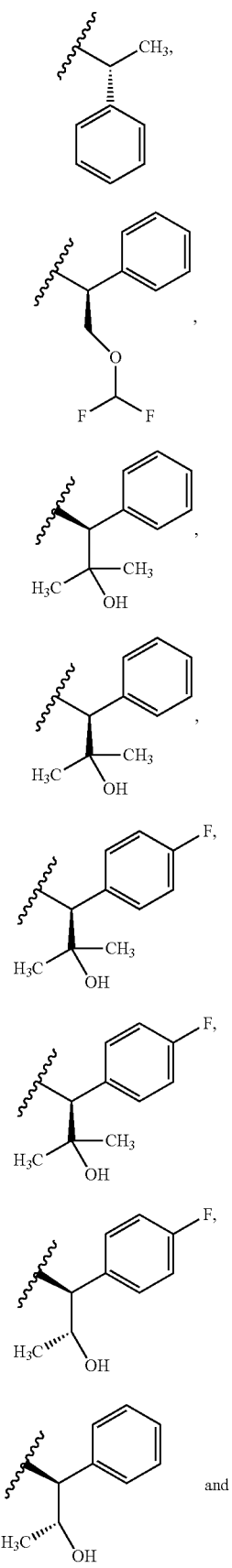

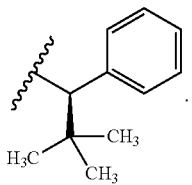

Thus, in one example $R^2$ is b1; in another example $R^2$ is b2; in another example $R^2$ is b3; in another example $R^2$ is b4; in another example $R^2$ is b5; in another example $R^2$ is b6; in another example $R^2$ is b7; in another example $R^2$ is b8; in another example $R^2$ is b9; and in another example $R^2$ is b10.

In one example $R^1$ is selected from the group consisting of: methylpyridyl, fluoropyridyl, —$CF_3$, —$C(O)CH_3$, —$CH_2OH$, cyclopropyl, —$CHF_2$, —$CH(OH)CH_3$, fluorophenyl, cyanopyridyl, and cyanophenyl; and $R^2$ is selected from the group consisting of b1 to b10.

In another example $R^1$ is selected from the group consisting of: a1, a2, a3, a4, a5, —$CF_3$, —$C(O)CH_3$, —$CH_2OH$, cyclopropyl, —$CH_2F$, and —$CH(OH)CH_3$; and $R^2$ is selected from the group consisting of b1 to b10.

In one example $R^3$ is H; and in another example $R^3$ is —$(C_1$-$C_4$ alkyl); and in another example $R^3$ is —$(C_1$-$C_2$ alkyl); and in another example $R^3$ is methyl; and in another example $R^3$ is ethyl.

In another example $R^5$ is —$(C_1$-$C_3$ alkyl); and in another example $R^5$ is methyl; and in another example $R^5$ is ethyl.

In one example $R^6$ is —$(C_1$-$C_4$ alkyl); and in another example $R^6$ is —$(C_1$-$C_3$ alkyl); and in another example $R^6$ is —$(C_3$-$C_4$ cycloalkyl); and in another example $R^6$ is methyl; and in another example $R^6$ is ethyl; and in another example $R^6$ is cyclopropyl.

In one example the $R^4$ substituent is —$(C_1$ to $C_6$alkyl). In another example the $R^4$ substituent is —$(C_1$ to $C_2$alkyl). In another example the $R^4$ substituent is methyl.

In one example the $R^4$ substituent is hydroxy substituted —$(C_1$-$C_6$alkyl). In another example the $R^4$ substituent is hydroxy substituted —$(C_1$-$C_2$alkyl). In another example $R^4$ is —$CH_2OH$.

In one example the $R^4$ substituent is —$(C_1$-$C_6$alkyl)-O—$(C_1$-$C_6$alkyl). In another example the $R^4$ substituent is —$(C_1$-$C_2$alkyl)-O—$(C_1$-$C_2$alkyl). In another example $R^4$ is —$CH_2OCH_3$.

In one example the $R^4$ substituent is —$NHR^3$. In another example the $R^4$ substituent is —$NHR^3$ wherein $R^3$ is selected from the group consisting of: $R^3$ is H and —$(C_1$-$C_4$alkyl). In another example the $R^4$ substituent is —$NHR^3$ wherein $R^3$ is selected from the group consisting of: $R^3$ is H, methyl and ethyl.

In one example the $R^4$ substituent is —$NHR^3$. In another example the $R^4$ substituent is —$NHR^3$ wherein $R^3$ is selected from the group consisting of: $R^3$ is H; and in another example $R^3$ is —$(C_1$-$C_4$ alkyl); and in another example $R^3$ is —$(C_1$-$C_2$ alkyl); and in another example $R^3$ is methyl; and in another example $R^3$ is ethyl.

In one example $R^1$ is selected from the group consisting of: methylpyridyl, fluoropyridyl, —$CF_3$, —$C(O)CH_3$, —$CH_2OH$, cyclopropyl, —$CHF_2$, —$CH(OH)CH_3$, fluorophenyl, cyanopyridyl, and cyanophenyl; $R^2$ is selected from the group consisting of b1 to b10; and $R^4$ is selected from the group consisting of: —$NHR^3$, —$OR^5$, —$CH(OH)R^6$, —$(C_1$ to $C_2$alkyl), hydroxy substituted —$(C_1$-$C_2$alkyl), and —$(C_1$-$C_2$alkyl)-O—$(C_1$-$C_2$alkyl).

In another example $R^1$ is selected from the group consisting of: a1, a2, a3, a4, a5, —$CF_3$, —$C(O)CH_3$, —$CH_2OH$, cyclopropyl, —$CH_2F$, and —$CH(OH)CH_3$; and $R^2$ is selected from the group consisting of b1 to b10; and $R^4$ is selected from the group consisting of: —$NHR^3$, —$OR^5$, —$CH(OH)R^6$, —($C_1$ to $C_2$alkyl), hydroxy substituted —($C_1$-$C_2$alkyl), and —($C_1$-$C_2$alkyl)-O—($C_1$-$C_2$alkyl).

In another example $R^1$ is selected from the group consisting of: a1, a2, a3, a4, a5, —$CF_3$, —$C(O)CH_3$, —$CH_2OH$, cyclopropyl, —$CH_2F$, and —$CH(OH)CH_3$; and $R^2$ is selected from the group consisting of b1 to b10; and $R^4$ is selected from the group consisting of: methyl, —$CH_2OH$, and —$CH_2OCH_3$.

In one example $R^1$ is selected from the group consisting of: methylpyridyl, fluoropyridyl, —$CF_3$, —$C(O)CH_3$, —$CH_2OH$, cyclopropyl, —$CHF_2$, —$CH(OH)CH_3$, fluorophenyl, cyanopyridyl, and cyanophenyl; $R^2$ is selected from the group consisting of b1 to b10; and $R^4$ is selected from the group consisting of: —($C_1$ to $C_2$alkyl), hydroxy substituted —($C_1$-$C_2$alkyl), and —($C_1$-$C_2$alkyl)-O—($C_1$-$C_2$alkyl).

In another example $R^1$ is selected from the group consisting of: a1, a2, a3, a4, a5, —$CF_3$, —$C(O)CH_3$, —$CH_2OH$, cyclopropyl, —$CH_2F$, and —$CH(OH)CH_3$; and $R^2$ is selected from the group consisting of b1 to b10; and $R^4$ is selected from the group consisting of: —($C_1$ to $C_2$alkyl), hydroxy substituted —($C_1$-$C_2$alkyl), and —($C_1$-$C_2$alkyl)-O—($C_1$-$C_2$alkyl).

In another example $R^1$ is selected from the group consisting of: a1, a2, a3, a4, a5, —$CF_3$, —$C(O)CH_3$, —$CH_2OH$, cyclopropyl, —$CH_2F$, and —$CH(OH)CH_3$; and $R^2$ is selected from the group consisting of b1 to b10; and $R^4$ is selected from the group consisting of: methyl, —$CH_2OH$, and —$CH_2OCH_3$.

Examples of the $R^6$—($C_1$-$C_6$)alkyl groups include, but are not limited to: —($C_1$-$C_4$)alkyl and —($C_1$-$C_2$)alkyl).

Examples of the $R^7$ halo groups include but are not limited to: Cl and F. Examples of the $R^7$—($C_1$-$C_6$)alkyl groups include, but are not limited to: —($C_1$-$C_4$)alkyl and —($C_1$-$C_2$)alkyl).

In one example $R^7$ is H.

One example of this invention is directed to a pharmaceutically acceptable salt of the compounds of formula (1.0).

Another example of this invention is directed to the compounds of formula (1.0), that is the free base form of the compounds of formula (1.0).

Examples of $R^1$ include but are not limited to:

(a) halo, such as, for example, (i) Br: (ii) Cl and (iii) F;

(b) ($C_1$-$C_6$)alkyl, such as, for example: (i) ($C_1$-$C_4$)alkyl, (ii) ($C_1$-$C_3$)alkyl, and (iv) ($C_1$-$C_2$)alkyl;

(c) ($C_1$-$C_6$)alkenyl, such as, for example: (i) ($C_2$-$C_4$) alkenyl, and (ii) ($C_2$-$C_3$)alkenyl;

(d) ($C_3$-$C_6$)cycloalkyl, such as, for example: (i) ($C_3$-$C_6$) cycloalkyl, and (ii) ($C_3$-$C_5$)cycloalkyl;

(e) heteroaryl, such as, for example: (i) a 5 or 6 membered ring comprising 1 to 3 heteroatoms independently selected from the group consisting of: O, S, and N, and wherein the remaining ring atoms are carbon, (ii) a 5 or 6 membered ring comprising one nitrogen, and wherein the remaining ring atoms are carbon, (iii) a 5 or 6 membered ring comprising two nitrogens, and wherein the remaining ring atoms are carbon, (iv) a 9 to 10 membered two ring system (i.e., the two rings are fused together) comprising 1 to 3 heteroatoms independently selected from the group consisting of: O, S, and N, and wherein the remaining ring atoms are carbon, (v) a 9 to 10 membered two ring system (i.e., the two rings are fused together) comprising 1 to 3 heteroatoms independently selected from the group consisting of: S, and N, and wherein the remaining ring atoms are carbon;

(f) substituted heteroaryl, such as, for example: (i) a substituted 5 or 6 membered ring comprising 1 to 3 heteroatoms independently selected from the group consisting of: O, S, and N, and wherein the remaining ring atoms are carbon, (ii) a substituted 5 or 6 membered ring comprising one nitrogen, and wherein the remaining ring atoms are carbon, (iii) a substituted 5 or 6 membered ring comprising two nitrogens, and wherein the remaining ring atoms are carbon, (iv) a substituted 9 to 10 membered two ring system (i.e., the two rings are fused together) comprising 1 to 3 heteroatoms independently selected from the group consisting of: O, S, and N, and wherein the remaining ring atoms are carbon, (v) a substituted 9 to 10 membered two ring system (i.e., the two rings are fused together) comprising 1 to 3 heteroatoms independently selected from the group consisting of: S, and N, and wherein the remaining ring atoms are carbon, and (vi) any one of the substituted heteroaryl moieties described in (f)(i)-(v) substituted with 1 to 3 substitutents independently selected from the group consisting of: ($C_1$-$C_6$)alkyl (e.g., methyl), halo (e.g., F and Cl) and ($C_1$-$C_3$)alkoxy (e.g., isopropyloxy-);

(g) heterocycloalkenyl, such as, for example: (i) a 5 or 6 membered ring comprising one or two double bonds and comprising 1 to 3 heteroatoms selected from the group consisting of: O, S, and N, (ii) a 5 or 6 membered ring comprising one or two double bonds and comprising 1 heteroatom selected from the group consisting of: O, and N, (iii) a 6 membered ring comprising one or two double bonds and comprising 1 N, (iv) a 6 membered ring comprising two double bonds and comprising one N, (v) a 6 membered ring comprising one double bond and comprising one O;

(h) substituted heterocycloalkenyl, such as, for example: (i) a substituted 5 or 6 membered ring comprising one or two double bonds and comprising 1 to 3 heteroatoms selected from the group consisting of: O, S, and N, (ii) a substituted 5 or 6 membered ring comprising one or two double bonds and comprising 1 heteroatom selected from the group consisting of: O, and N, (iii) a substituted 6 membered ring comprising one or two double bonds and comprising 1 N, (iv) a substituted 6 membered ring comprising two double bonds and comprising one N, (v) a 6 substituted membered ring comprising one double bond and comprising one O, and (vi) any one of the substituted heterocycloalkenyl moieties described in (h)(i)-(v) substituted with 1 to 3 substituents independently selected from the group consisting of: ($C_1$ to $C_6$)alkyl (e.g., ($C_1$-$C_3$)alkyl, and in one example methyl) and =O;

(i) —($C_1$-$C_6$)alkyl-O—($C_1$-$C_6$)alkyl, such as, for example: (i) a —($C_1$-$C_4$)alkyl-O—($C_1$-$C_3$)alkyl, and (ii) a-($C_1$-$C_3$)alkyl-O—($C_1$-$C_2$)alkyl);

(j) aryl, such as, for example: (i) a ($C_6$ to $C_{10}$) aryl, (ii) a ($C_6$ to $C_{10}$) multicyclic ring system (i.e., a fused ring system having two atoms common to both rings), wherein at least one ring is a ($C_6$ to $C_{10}$) aryl, and the remaining rings are selected from the group consisting of: ($C_6$ to $C_{10}$) aryl heterocyloalkyl (as defined above), cycloalkyl (as defined above), and heterocyloalkenyl (as defined above), and (iii) wherein examples include, but are not limited to: phenyl, naphthyl and dihydrobenzodioxinyl, and in one example, phenyl and dihydrobenzodioxinyl; and (k) substituted aryl, such as, for example: (i) a substituted ($C_6$ to $C_{10}$) aryl, and (ii) a substituted ($C_6$ to $C_{10}$) multcyclic iring system (i.e., a fused ring system having two atoms common to both rings), wherein at least one ring is a ($C_6$ to $C_{10}$) aryl, and the remaining rings are selected from the group consisting of: ($C_6$ to $C_{10}$) aryl heterocyloalkyl (as defined above), cycloalkyl (as defined above), and heterocyloalkenyl (as defined above), and wherein examples include, but are not limited to: substituted phenyl (e.g., phenyl substituted with 1-3 substitutents independently selected from the group consisting of: halo (e.g., F and Cl), CN, and —S(O)$_2$($C_1$-$C_6$)alkyl (e.g., —S(O)$_2$($C_1$-$C_2$)alkyl, and —S(O)$_2$CH$_3$).

In one example $R^1$ is selected from the group consisting of: —CF$_3$, —C(O)CH$_3$, —CH$_2$OH, cyclopropyl, —CHF$_2$, —CH(CH$_3$)OH, —C(CH$_3$)F$_2$,

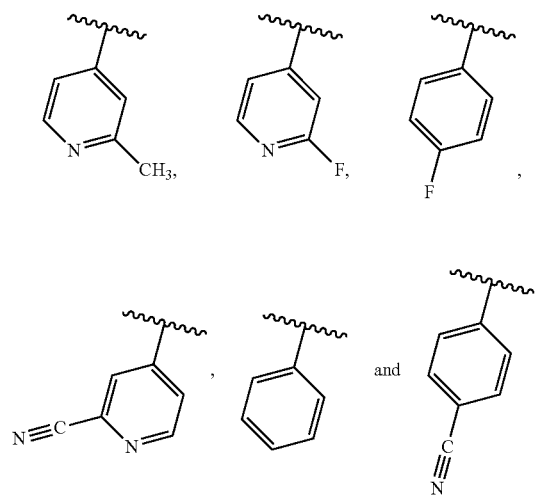

Other examples of $R^1$ include but are not limited to: —(CH$_2$)$_3$—O—CH$_3$, CH$_3$CH$_2$CH$_2$—, cyclopropyl, CH$_3$CH=CH—, Br, pyridyl,

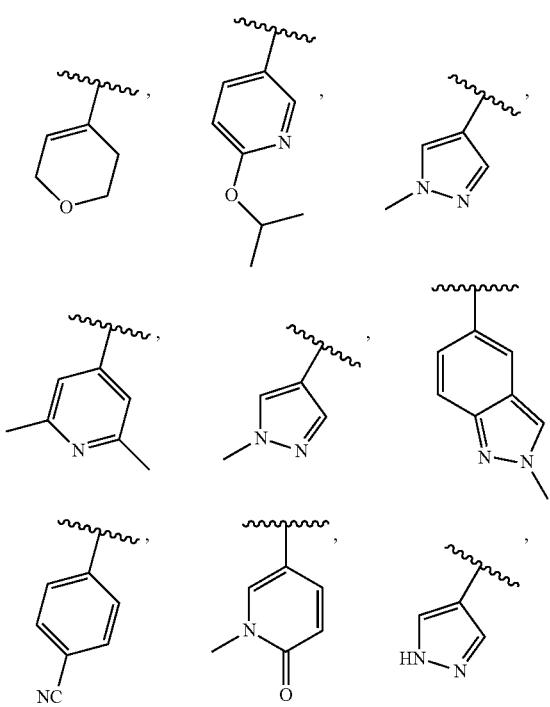

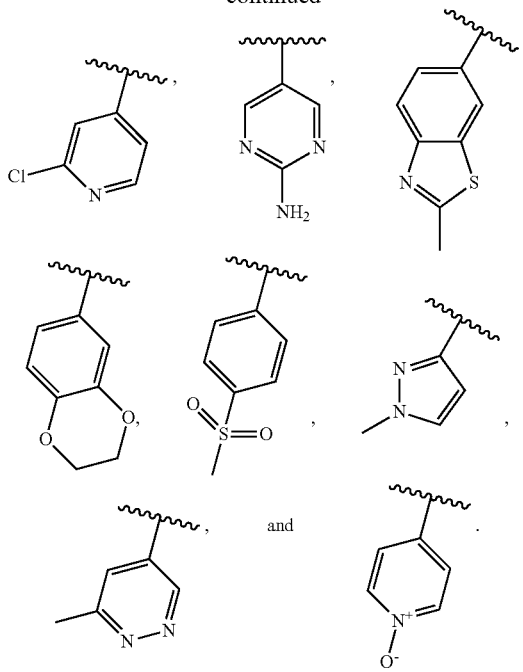

Other examples of this invention are directed to any one of the compounds described herein wherein the compounds are in the free base form.

In another example of this invention the compounds of formula (1) are selected from the group consisting of the compounds
(R)-1-(4-Methyl-3-(2-methylpyridin-4-yl)-1H-pyrazolo[4,3-c]pyridin-6-yl)-3-(1-phenylethyl)urea,
1-[3-(2-fluoropyridin-4-yl)-4-methyl-1H-pyrazolo[4,3-c]pyridin-6-yl]-3-[(1R)-1-phenylethyl]urea,
(R)-1-(3-(2-fluoropyridin-4-yl)-4-(hydroxymethyl)-1H-pyrazolo[4,3-c]pyridin-6-yl)-3-(1-phenylethyl)urea,
(R)-1-(4-(hydroxymethyl)-3-(2-methylpyridin-4-yl)-1H-pyrazolo[4,3-c]pyridin-6-yl)-3-(1-phenylethyl)urea,
(R)-1-(3-cyclopropyl-4-(hydroxymethyl)-1H-pyrazolo[4,3-c]pyridin-6-yl)-3-(1-phenylethyl)urea,
1-[3-cyclopropyl-4-(hydroxymethyl)-1H-pyrazolo[4,3-c]pyridin-6-yl]-3-[(1S)-2-hydroxy-2-methyl-1-phenylpropyl]urea,
1-[3-cyclopropyl-4-(hydroxymethyl)-1H-pyrazolo[4,3-c]pyridin-6-yl]-3-[(1S)-1-(4-fluorophenyl)-2-hydroxy-2-methylpropyl]urea,
1-[3-cyclopropyl-4-(hydroxymethyl)-1H-pyrazolo[4,3-c]pyridin-6-yl]-3-[(1S,2R)-1-(4-fluorophenyl)-2-hydroxypropyl]urea,
1-[3-cyclopropyl-4-(hydroxymethyl)-1H-pyrazolo[4,3-c]pyridin-6-yl]-3-[(1S,2R)-2-hydroxy-1-phenylpropyl]urea,
1-[(1S)-2-(difluoromethoxy)-1-phenylethyl]-3-[4-(hydroxymethyl)-3-(2-methylpyridin-4-yl)-1H-pyrazolo[4,3-c]pyridin-6-yl]urea,
1-[3-(4-fluorophenyl)-4-(hydroxymethyl)-1H-pyrazolo[4,3-c]pyridin-6-yl]-3-[(1R)-1-phenylethyl]urea,
1-[3-(2-cyanopyridin-4-yl)-4-(hydroxymethyl)-1H-pyrazolo[4,3-c]pyridin-6-yl]-3-[(1R)-1-phenylethyl]urea,
1-[3-(4-fluorophenyl)-4-(hydroxymethyl)-1H-pyrazolo[4,3-c]pyridin-6-yl]-3-[(1S)-2-hydroxy-2-methyl-1-phenylpropyl]urea, 1-[3-(4-fluorophenyl)-4-(hydroxymethyl)-1H-pyrazolo[4,3-c]pyridin-6-yl]-3-[(1S,2R)-1-(4-fluorophenyl)-2-hydroxypropyl]urea, 1-[(1S)-1-(4-fluorophenyl)-2-hydroxy-2-methylpropyl]-3-[3-(4-fluorophenyl)-4-(hydroxymethyl)-1H-pyrazolo[4,3-c]pyridin-6-yl]urea, 1-[3-(4-fluorophenyl)-4-(hydroxymethyl)-1H-pyrazolo[4,3-c]pyridin-6-yl]-3-[(1S,2R)-2-hydroxy-1-phenylpropyl]urea, 1-[(1R)-2,2-dimethyl-1-phenylpropyl]-3-[3-(4-fluorophenyl)-4-(hydroxymethyl)-1H-pyrazolo[4,3-c]pyridin-6-yl]urea, 1-[(1S)-2-hydroxy-2-methyl-1-phenylpropyl]-3-[4-(hydroxymethyl)-3-phenyl-1H-pyrazolo[4,3-c]pyridin-6-yl]urea, 1-[3-(4-cyanophenyl)-4-(hydroxymethyl)-1H-pyrazolo[4,3-c]pyridin-6-yl]-3-[(1S)-2-hydroxy-2-methyl-1-phenylpropyl]urea, (R)-1-(4-(Methoxymethyl)-3-(2-methylpyridin-4-yl)-1H-pyrazolo[4,3-c]pyridin-6-yl)-3-(1-phenylethyl)urea, (S)-1-(3-(difluoromethyl)-4-methyl-1H-pyrazolo[4,3-c]pyridin-6-yl)-3-(2-hydroxy-2-methyl-1-phenylpropyl)urea, (S)-1-(3-(difluoromethyl)-4-(hydroxymethyl)-1H-pyrazolo[4,3-c]pyridin-6-yl)-3-(2-hydroxy-2-methyl-1-phenylpropyl)urea, 1-[3-(difluoromethyl)-4-(hydroxymethyl)-1H-pyrazolo[4,3-c]pyridin-6-yl]-3-[(1S)-1-(4-fluorophenyl)-2-hydroxy-2-methylpropyl]urea, 1-[3-(difluoromethyl)-4-(hydroxymethyl)-1H-pyrazolo[4,3-c]pyridin-6-yl]-3-[(1R)-1-phenylethyl]urea, (R)-1-(3,4-bis(hydroxymethyl)-1H-pyrazolo[4,3-c]pyridin-6-yl)-3-(1-phenylethyl)urea, (R)-1-(3-acetyl-4-(hydroxymethyl)-1H-pyrazolo[4,3-c]pyridin-6-yl)-3-(1-phenylethyl)urea, 1-(3-(1-hydroxyethyl)-4-(hydroxymethyl)-1H-pyrazolo[4,3-c]pyridin-6-yl)-3-((R)-1-phenylethyl)urea, (S)-1-(3-(1,1-difluoroethyl)-4-(hydroxymethyl)-1H-pyrazolo[4,3-c]pyridin-6-yl)-3-(2-hydroxy-2-methyl-1-phenylpropyl)urea, or (R)-1-(4-(hydroxymethyl)-3-(trifluoromethyl)-1H-pyrazolo[4,3-c]pyridin-6-yl)-3-(1-phenylethyl)urea, or a pharmaceutically acceptable salt thereof.

In another example of this invention the compounds of formula (1) are selected from the group consisting of the final compounds of Examples 1 to 29. Thus, in one example the compound is the final compound of Ex. 1; and in another example the final compound of Ex. 2; and in another example the final compound of Ex. 3; and in another example the final compound of Ex. 4; and in another example the final compound of Ex. 5; and in another example the final compound of Ex. 6; and in another example the final compound of Ex. 7; and in another example the final compound of Ex. 8; and in another example the final compound of Ex. 9; and in another example the final compound of Ex. 10; and in another example the final compound of Ex. 11; and in another example the final compound of Ex. 12; and in another example the final compound of Ex. 13; and in another example the final compound of Ex. 14; and in another example the final compound of Ex. 15; and in another example the final compound of Ex. 16; and in another example the final compound of Ex. 17; and in another example the final compound of Ex. 18; and in another example the final compound of Ex. 19; and in another example the final compound of Ex. 20; and in another example the final compound of Ex. 21; and in another example the final compound of Ex. 22; and in another example the final compound of Ex. 23; and in another example the final compound of Ex. 24; and in another example the final compound of Ex. 25; and in another example the final compound of Ex. 26; and in another example the final compound of Ex. 27; and in another example the final compound of Ex. 28; and in another example the final compound of Ex. 29.

Another example of this invention is directed to the pharmaceutically acceptable salts of the compounds of formula (1.0). Thus, other examples of this invention are directed to any one of the examples described above wherein the compound of formula (1.0) is in the form of a pharmaceutically acceptable salt.

Another example of this invention is directed to pharmaceutically acceptable salts of the final compounds of Examples 1-29.

Another example of this invention is directed to the solvates of the compounds of formula (1.0).

Other examples of this invention are directed to any one of the examples of formula (1.0) wherein the compound is in pure and isolated form. Other examples of this invention are directed to any one of the examples of formula (1.0) wherein the compound is in pure form. Other examples of this invention are directed to any one of the examples of formula (1.0) wherein the compound is in isolated form.

Another example of this invention is directed to a pharmaceutical composition comprising an effective amount of at least one compound (e.g., 1, 2 or 3, or 1 or 2, or 1, and usually 1) of formula (1.0), or a pharmaceutically acceptable salt thereof, and a pharmaceutically acceptable carrier. Another example of this invention is directed to a pharmaceutical composition comprising an effective amount of a compound of formula (1.0), or a pharmaceutically acceptable salt thereof, and a pharmaceutically acceptable carrier.

Another example of this invention is directed to a pharmaceutical composition comprising an effective amount of at least one compound selected from the group consisting of the final compounds of Examples 1-29, or a pharmaceutically acceptable salt thereof, and a pharmaceutically acceptable carrier.

Another example of this invention is directed to a pharmaceutical composition comprising an effective amount of one compound selected from the group consisting of the final compounds of Examples 1-29, or a pharmaceutically acceptable salt thereof, and a pharmaceutically acceptable carrier.

Another example of this invention is directed to a pharmaceutical composition comprising an effective amount of a compound of formula (1.0), a chemotherapeutic agent, and a pharmaceutically acceptable carrier.

The compounds of the invention are useful in preparing a medicament that may be useful in treating cancer.

The compounds of this invention inhibit the activity of ERK2. Thus, this invention further provides a method of inhibiting ERK in mammals, especially humans, by the administration of an effective amount of one or more (e.g., one) compounds of this invention. The administration of the compounds of this invention to patients, to inhibit ERK2, may be useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention. In the treatment of breast cancer, the compounds of formula (1) can be be administered in a treatment protocol which also includes the administration of an effective amount of at least one (e.g., 1-3, or 1-2, or 1) antihormonal agent (i.e., the methods of treating breast cancer can include hormonal therapies).

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

The methods of treating cancer described herein include methods of treating cancer that comprise administering a therapeutically effective amount of a compound of the instant invention in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein.

In any of the methods of treating cancer described herein, unless stated otherwise, the methods can optionally include the administration of an effective amount of radiation therapy. For radiation therapy, γ-radiation is preferred.

Thus, another example of this invention is directed to a method of treating cancer in a patient in need of such treatment, said method comprising administering an effective amount of a compound of formula (1.0). Another example of this invention is directed to a method of treating cancer in a patient in need of such treatment, said method comprising administering to said patient an effective amount of a compound of formula (1.0), and an effective amount of at least one (e.g., 1-3, 1-2, or 1) chemotherapeutic agent.

The compounds, compositions and methods provided herein may be useful for the treatment of cancer whose growth, progression and or metastasis are at least in part mediated by activation of the ERK pathway. Cancers that may be treated by the compounds, compositions and methods of the invention include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

In one example of this invention the cancer treated is colo-rectal cancer (such as, for example, colon adenocarcinoma and colon adenoma). Thus, another example of this invention is directed to a method of treating colo-rectal cancer in a patient in need of such treatment, said method comprising administering an effective of a compound of formula (1.0) (e.g., a final compound of Examples 1 to 29), or a pharmaceutically acceptable salt thereof, to said patient. Another example of this invention is directed to a method of treating colo-rectal cancer in a patient in need of such treatment, said method comprising administering to said patient an effective amount of a compound of formula (1.0) (e.g., a final compound of Examples 1 to 29), or a pharmaceutically acceptable salt thereof, and an effective amount of at least one (e.g., 1-3, or 1-2, or 1) chemotherapeutic agent.

In one example of this invention the cancer treated is melanoma. Thus, another example of this invention is directed to a method of treating melanoma in a patient in need of such treatment, said method comprising administering an effective amount of a compound of formula (1.0) (e.g. a final compound of Examples 1 to 29), or a pharmaceutically acceptable salt thereof, to said patient. Another example of this invention is directed to a method of treating melanoma in a patient in need of such treatment, said method comprising administering to said patient an effective amount of a compound of formula (1.0) (e.g., a final compound of Examples 1 to 29), or a pharmaceutically acceptable salt thereof, and an effective amount of at least one (e.g., 1-3, or 1-2, or 1) chemotherapeutic agent.

The compounds of the invention are also useful in preparing a medicament that may be useful in treating cancer.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or *arachis* oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a composition according to this invention is administered into a human subject, the daily dosage will normally be determined by the prescribing physician with the dosage generally varying according to the age, weight, and response of the individual patient, as well as the severity of the patient's symptoms.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease. Compounds of this invention can be administered in a total daily dose of 10 mg to 3000 mg. For example, compounds of the instant invention can be administered in a total daily dose of up to 3000 mg. Compounds of the instant invention can be administered once daily (QD), or divided into multiple daily doses such as twice daily (BID), and three times daily (TID). Compounds of the instant invention can be administered at a total daily dosage of up to 3000 mg, e.g., 200 mg, 300 mg, 400 mg, 600 mg, 800 mg, 1000 mg, 2000 mg or 3000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days. The compounds of this invention may be administered discontinuously rather than continuously during the treatment cycle. Thus, the compounds of this invention may be administered daily for one or more weeks during the cycle and discontinued for one or more weeks during the cycle, with this pattern of administration repeating during the treatment cycle (e.g., administration for a week and then discontinued for a week). This discontinuous treatment may also be based upon numbers of days rather than a full week. The number of days (or weeks) that the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal to or greater than the number of days or weeks that the compounds of this invention are not dosed.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular example, the compounds of the instant invention may be administered three times daily for two consecutive weeks, followed by one week of rest.

Any one or more of the specific dosages and dosage schedules of the compounds of the instant invention, may also be applicable to any one or more of the therapeutic agents to be used in the combination treatment (hereinafter refered to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an example, the administration for a compound of the instant invention is oral administration. In another example, the administration for a compound of the instant invention is intravenous administration. Thus, in accordance with these examples, a compound of the instant invention is administered orally or intravenously, and the second therapeutic agent can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6<sup>th</sup> edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydro0xy-3,5-dimethoxyphenyl]-5,5a,6,8,8a,9-hexahydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. No. 60/310,927 (filed Aug. 8, 2001) and 60/349, 925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another example of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an example, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); DROMOSTANOLONE PROPIONATE (DROMOSTANOLONE®); DROMOSTANOLONE PROPIONATE (MASTERONE INJECTION®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®).

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention in combination with paclitaxel or trastuzumab.

The invention further encompasses a method of treating or preventing cancer that comprises administering a therapeutically effective amount of a compound of the instant invention in combination with a COX-2 inhibitor.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCHinhibitors, agents that interfere with receptor tyrosine kinases (RTKs), an agent that interferes with a cell cycle checkpoint, and any of the therapeutic agents listed above.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physicians'Desk Reference, 56th Edition, 2002 (published by Medical Economics company, Inc. Montvale, N.J. 07645-1742), the Physicians' Desk Reference, 57th Edition, 2003 (published by Thompson PDR, Montvale, N.J. 07645-1742), the Physicians' Desk Reference, 60th Edition, 2006 (published by Thompson PDR, Montvale, N.J. 07645-1742), and the Physicians' Desk Reference, 64th Edition, 2010 (published by PDR Network, LLC at Montvale, N.J. 07645-1725); the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes.

Substituent numbering as shown in the Reaction Schemes do not necessarily correlate to that used in the claims and often, for clarity, a single substituent is shown attached to the compound where multiple substituents are optionally allowed under the definitions of formula (1.0) hereinabove.

General Schemes

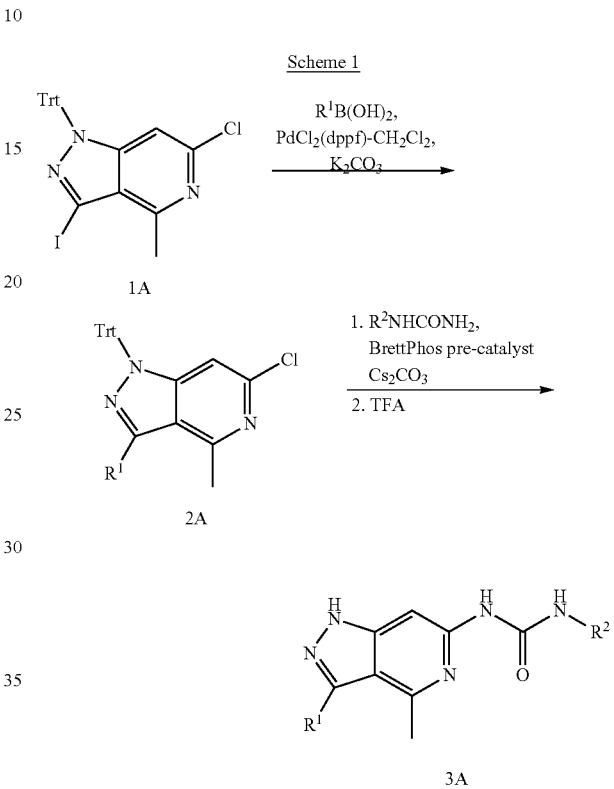

Step 1: 3-Aryl derivatives 2A have been prepared by subjecting 6-chloro-3-iodo-4-methyl-1-trityl-1H-pyrazolo[4,3-c]pyridine 1A and the appropriate boronic ester or acid to suitable cross-coupling conditions such as $PdCl_2(dppf)$-$CH_2Cl_2$ and $K_2CO_3$ in 1,4-dioxane and water (4:1 ratio) at 80° C. for 1-4 hours.

Step 2: Urea derivatives 3A have been prepared by subjecting various 6-chloro-4-methyl-1-trityl-1H-pyrazolo[4,3-c]pyridine intermediates 2A and the appropriate primary urea to suitable cross-coupling conditions, such as BrettPhos pre-catalyst and $Cs_2CO_3$ in 1,4-dioxane at 100° C. for 1 to 16 hr, followed by treatment with TFA and triethylsilane (with or without DCM).

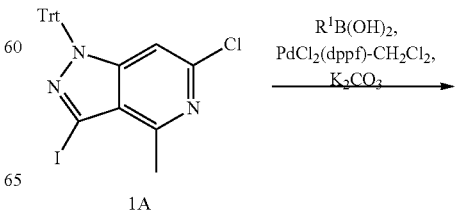

Scheme 2

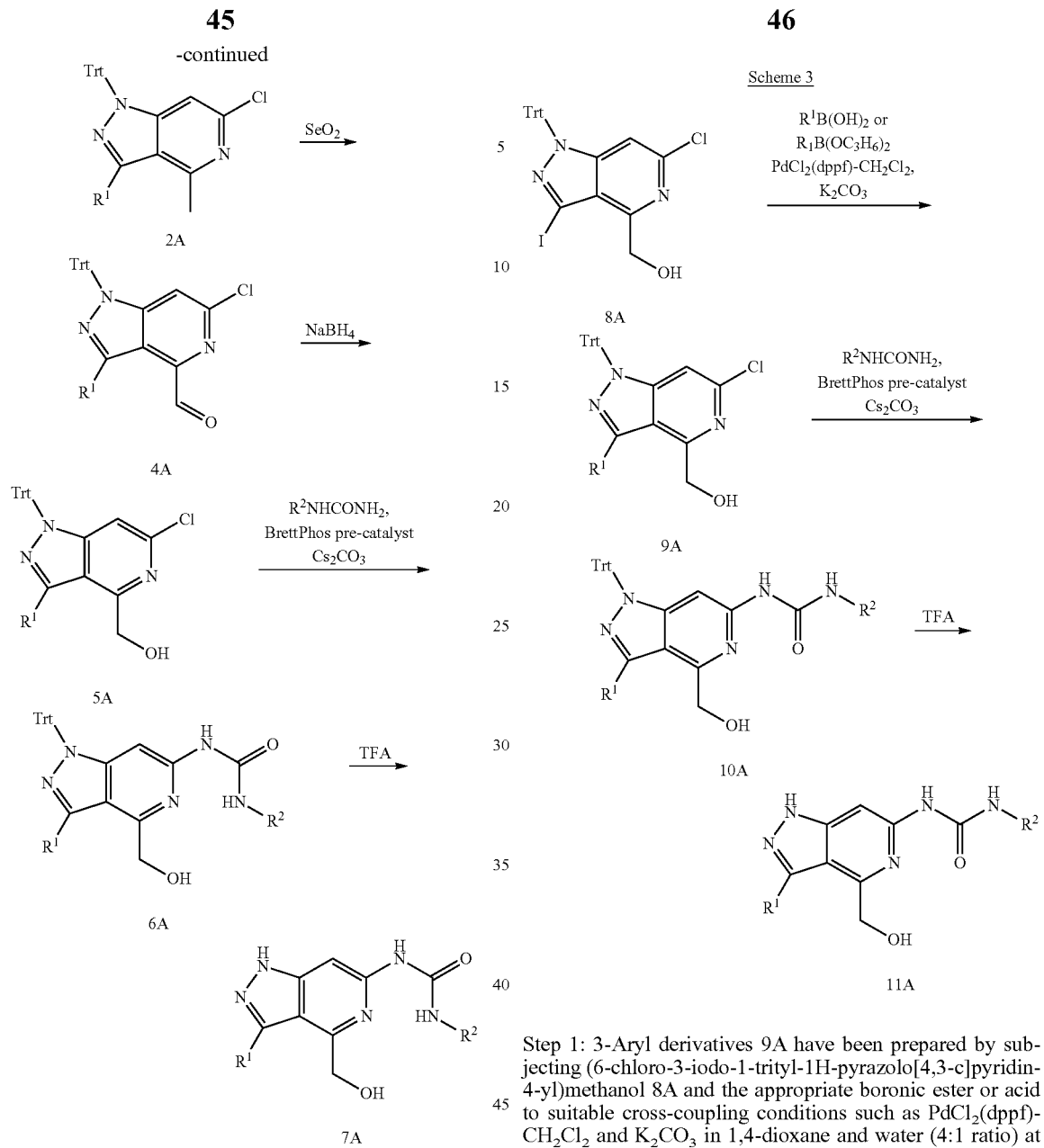

Step 1: 3-Aryl derivatives 2A have been prepared by subjecting 6-chloro-3-iodo-4-methyl-1-trityl-1H-pyrazolo[4,3-c]pyridine 1A and the appropriate boronic ester or acid to suitable cross-coupling conditions such as PdCl₂(dppf)-CH₂Cl₂ and K₂CO₃ in 1,4-dioxane and water (4:1 ratio) at 80° C. for 1-4 hours.

Step 2: 4-Carboxaldehyde derivatives 4A have been prepared by subjecting 4-methyl intermediates 2A to selenium dioxide in 1,4-dioxane at reflux for 1-4 days.

Step 3: 4-Hydroxymethyl compounds 5A have been prepared by subjecting 4A to suitable reduction conditions, such as sodium borohydride in DCM and MeOH at 0° C.

Step 4: Urea derivatives 7A have been prepared by subjecting 5A and the appropriate primary urea to suitable cross-coupling conditions, such as BrettPhos pre-catalyst and Cs₂CO₃ in 1,4-dioxane at 100° C. for 1 to 16 hr, followed by treatment with TFA and triethylsilane (with or without DCM).

Step 1: 3-Aryl derivatives 9A have been prepared by subjecting (6-chloro-3-iodo-1-trityl-1H-pyrazolo[4,3-c]pyridin-4-yl)methanol 8A and the appropriate boronic ester or acid to suitable cross-coupling conditions such as PdCl₂(dppf)-CH₂Cl₂ and K₂CO₃ in 1,4-dioxane and water (4:1 ratio) at 80° C. for 1-4 hours.

Step 2: Urea derivatives 11A have been prepared by subjecting 3-aryl derivatives 9A and the appropriate primary urea to suitable cross-coupling conditions, such as BrettPhos pre-catalyst and Cs₂CO₃ in 1,4-dioxane at 100° C. for 1 to 16 hr, followed by treatment with TFA and triethylsilane (with or without DCM).

Scheme 4

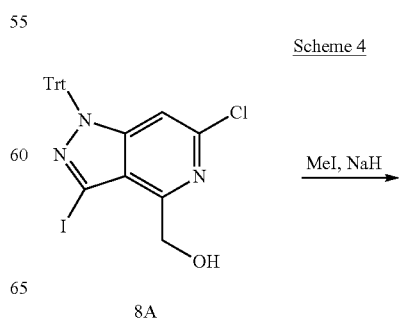

-continued

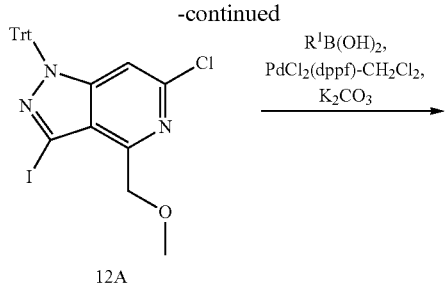

12A

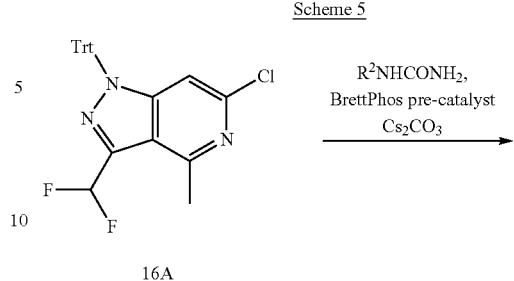

Scheme 5

16A

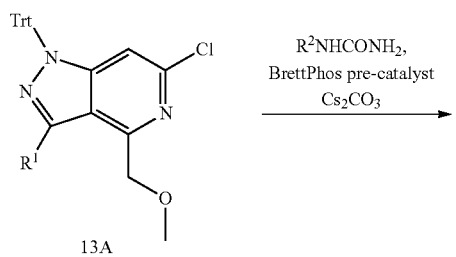

13A

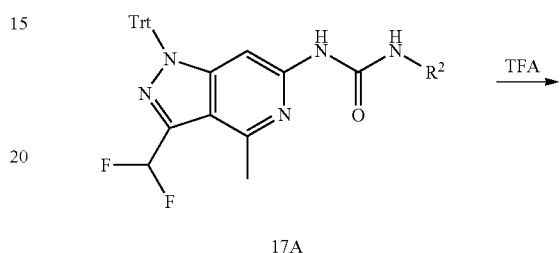

17A

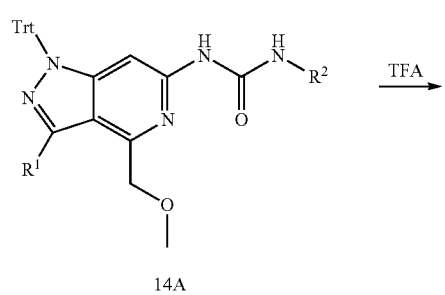

14A

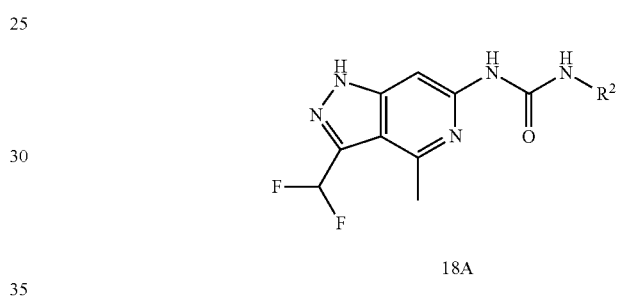

18A

Step 1: Urea derivatives 18A have been prepared by subjecting 6-chloro-3-(difluoromethyl)-4-methyl-1-trityl-1H-pyrazolo[4,3-c]pyridine 16A and the appropriate primary urea to suitable cross-coupling conditions, such as BrettPhos pre-catalyst and $Cs_2CO_3$ in 1,4-dioxane at 100° C. for 1 to 16 hr, followed by treatment with TFA and triethylsilane (with or without DCM).

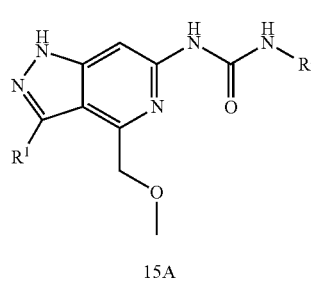

15A

Step 1: 4-Methoxymethyl derivatives 12A have been prepared by subjecting 8A to suitable nucleophilic substitution conditions, such as iodomethane with a suitable base, such as NaH, in DMF at 0° C. to rt.

Step 2: 3-Aryl derivatives 13A have been prepared by subjecting 6-chloro-3-iodo-4-(methoxymethyl)-1-trityl-1H-pyrazolo[4,3-c]pyridine intermediates 12A and the appropriate boronic ester or acid to suitable cross-coupling conditions, such as $PdCl_2(dppf)$-$CH_2Cl_2$ and $K_2CO_3$ in 1,4-dioxane and water (4:1 ratio) at 80° C. for 1-4 hours.

Step 3: Urea derivatives 15A have been prepared by subjecting 13A and the appropriate primary urea to suitable cross-coupling conditions, such as BrettPhos pre-catalyst and $Cs_2CO_3$ in 1,4-dioxane at 100° C. for 1 to 16 hr, followed by treatment with TFA and triethylsilane (with or without DCM).

Scheme 6

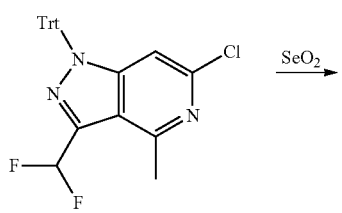

16A

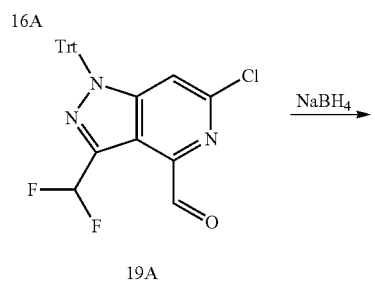

19A

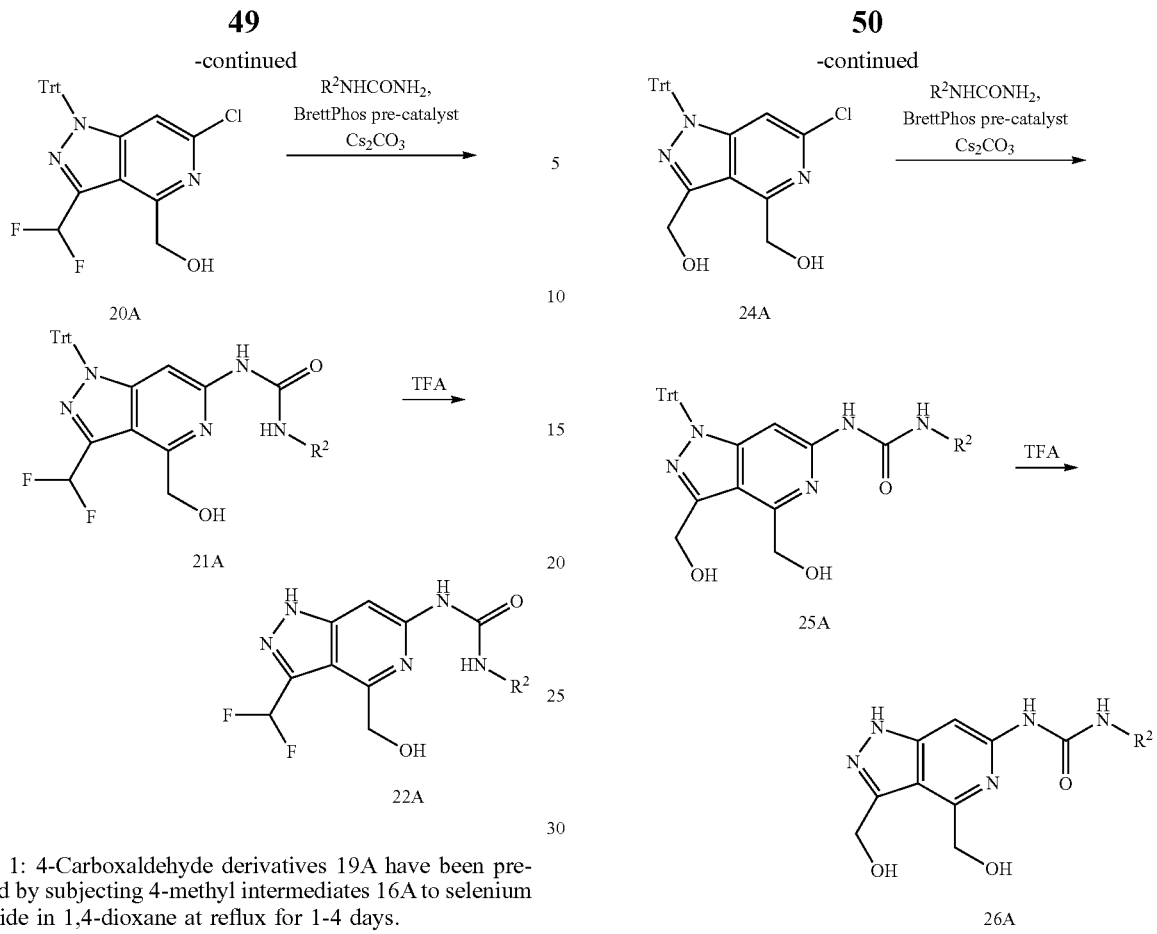

Step 1: 4-Carboxaldehyde derivatives 19A have been prepared by subjecting 4-methyl intermediates 16A to selenium dioxide in 1,4-dioxane at reflux for 1-4 days.

Step 2: 4-Hydroxymethyl compounds 20A have been prepared by subjecting 19A to suitable reduction conditions, such as sodium borohydride in DCM and MeOH at 0° C.

Step 3: Urea derivatives 22A have been prepared by subjecting (6-chloro-3-(difluoromethyl)-1-trityl-1H-pyrazolo[4,3-c]pyridin-4-yl)methanol 20A and the appropriate primary urea to suitable cross-coupling conditions, such as BrettPhos pre-catalyst and Cs₂CO₃ in 1,4-dioxane at 100° C. for 1 to 16 hr, followed by treatment with TFA and triethylsilane (with or without DCM).

Step 1: Methyl ester derivatives have been prepared by subjecting (6-chloro-3-iodo-1-trityl-1H-pyrazolo[4,3-c]pyridin-4-yl)methanol 8A to suitable carbonylation conditions, such as PdCl₂(dppf)-CH₂Cl₂ and sodium acetate in MeOH under a CO atmosphere at 65° C. and 80 psi for 3 days.

Step 2: 3-Hydroxymethyl compounds 24A were prepared by subjecting 23A to appropriate reduction conditions, such as DIBAL-H in THF at −78° C.

Step 3: Urea derivatives 26A have been prepared by subjecting (6-chloro-1-trityl-1H-pyrazolo[4,3-c]pyridine-3,4-diyl)dimethanol 24A and the appropriate primary urea to suitable cross-coupling conditions, such as BrettPhos pre-catalyst and Cs₂CO₃ in 1,4-dioxane at 100° C. for 1 to 16 hr, followed by treatment with TFA and triethylsilane (with or without DCM).

Scheme 7

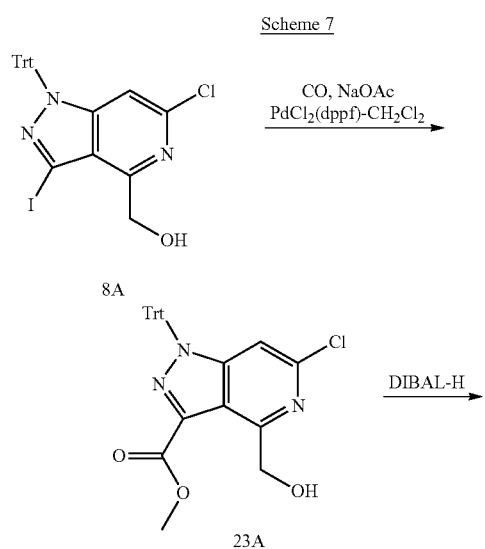

Scheme 8

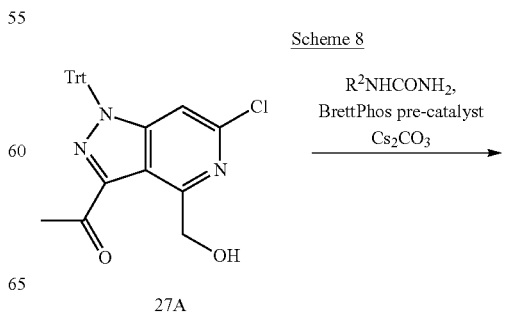

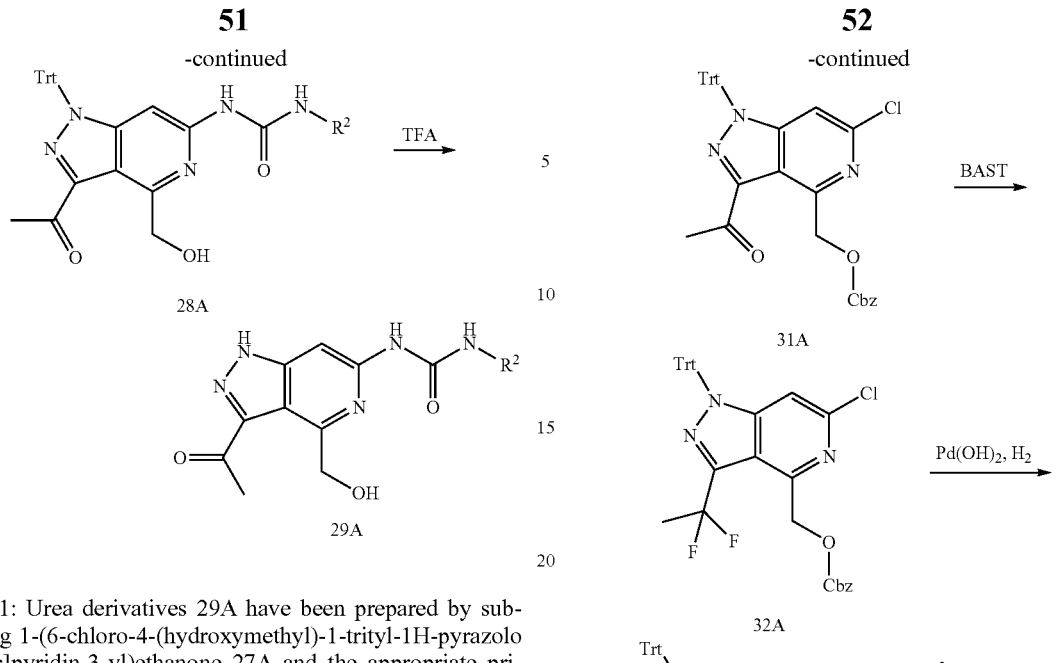

Step 1: Urea derivatives 29A have been prepared by subjecting 1-(6-chloro-4-(hydroxymethyl)-1-trityl-1H-pyrazolo[4,3-c]pyridin-3-yl)ethanone 27A and the appropriate primary urea to suitable cross-coupling conditions, such as BrettPhos pre-catalyst and Cs$_2$CO$_3$ in 1,4-dioxane at 100° C. for 1 to 16 hr, followed by treatment with TFA and triethylsilane (with or without DCM).

Scheme 9

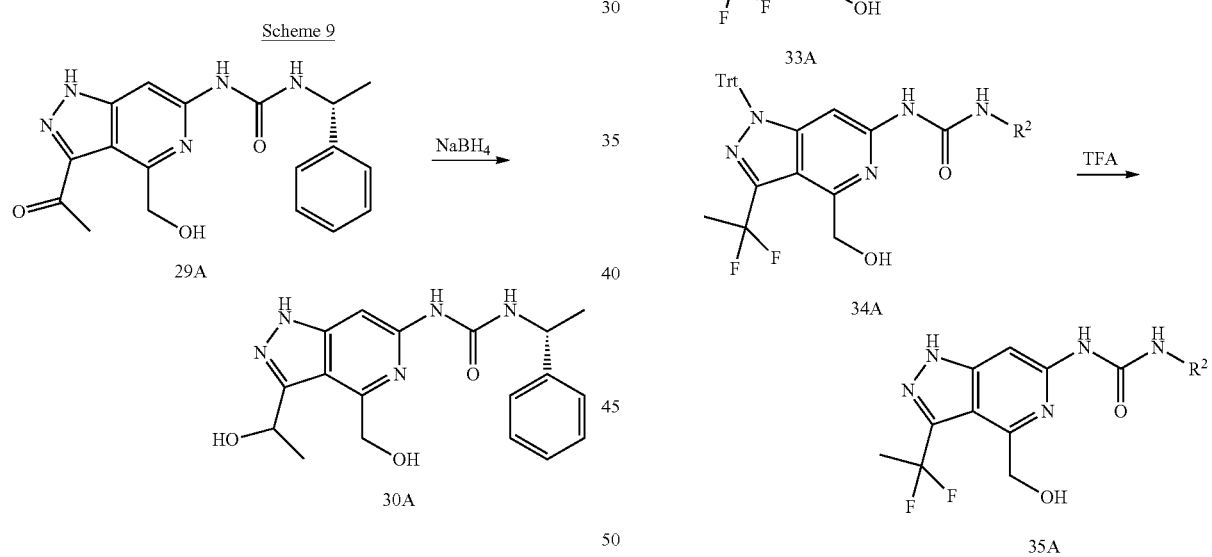

Step 1: 30A was prepared by subjecting 29A to appropriate reducing conditions such as sodium borohydride in DCM and MeOH at room temperature for 1 hour.

Scheme 10

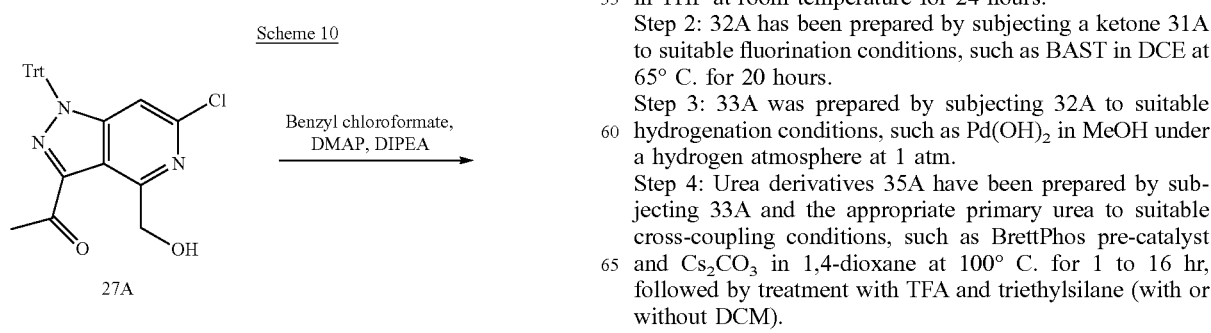

Step 1: The CBZ-protected alcohol 31A was prepared by treating 27A with benzyl chloroformate, DMAP, and DIPEA in THF at room temperature for 24 hours.

Step 2: 32A has been prepared by subjecting a ketone 31A to suitable fluorination conditions, such as BAST in DCE at 65° C. for 20 hours.

Step 3: 33A was prepared by subjecting 32A to suitable hydrogenation conditions, such as Pd(OH)$_2$ in MeOH under a hydrogen atmosphere at 1 atm.

Step 4: Urea derivatives 35A have been prepared by subjecting 33A and the appropriate primary urea to suitable cross-coupling conditions, such as BrettPhos pre-catalyst and Cs$_2$CO$_3$ in 1,4-dioxane at 100° C. for 1 to 16 hr, followed by treatment with TFA and triethylsilane (with or without DCM).

Scheme 11

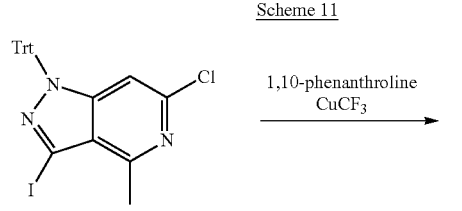

1A

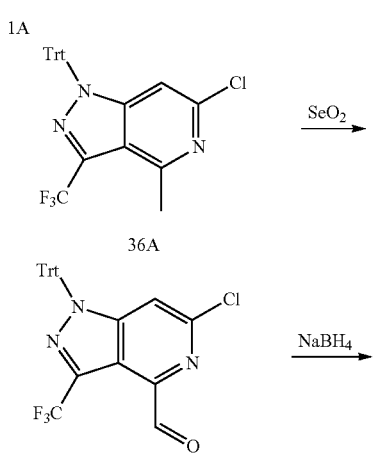

36A

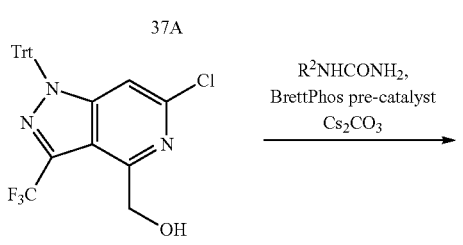

37A

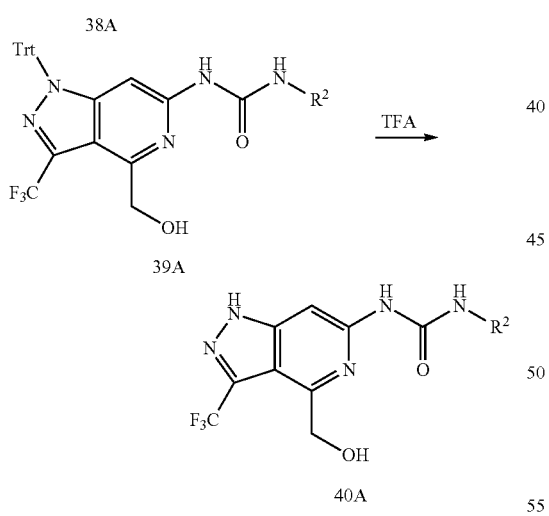

Step 1: 3-Trifluoromethyl derivatives 36A have been prepared by treating 1A with trifluoromethyl (1,10-phenanthroline)copper in DMF at 50° C. for 12 hours.

Step 2: 4-Carboxaldehyde derivatives 37A have been prepared by subjecting 4-methyl intermediates 36A to selenium dioxide in 1,4-dioxane at reflux for 1-4 days.

Step 3: 4-Hydroxymethyl compounds 38A have been prepared by subjecting 37A to suitable reducing conditions, such as sodium borohydride in MeOH and THF at room temperature.

Step 4: Urea derivatives 40A have been prepared by subjecting 38A and the appropriate primary urea to suitable cross-coupling conditions, such as BrettPhos pre-catalyst and $Cs_2CO_3$ in 1,4-dioxane at 100° C. for 1 to 16 hr, followed by treatment with TFA and triethylsilane (with or without DCM).

Scheme 12

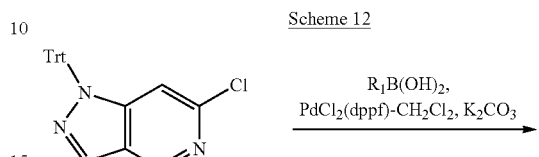

1A

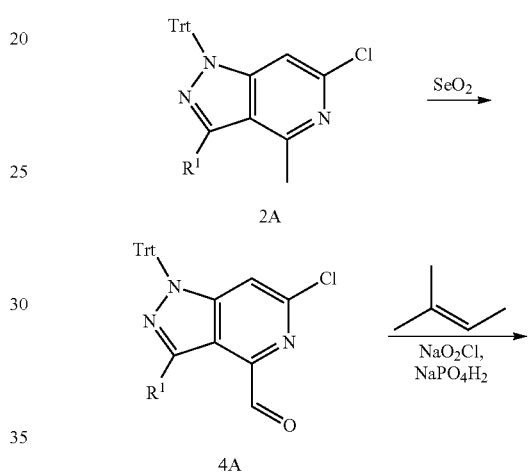

2A

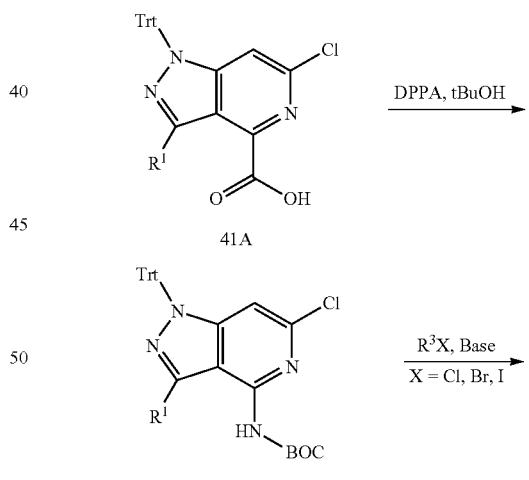

4A

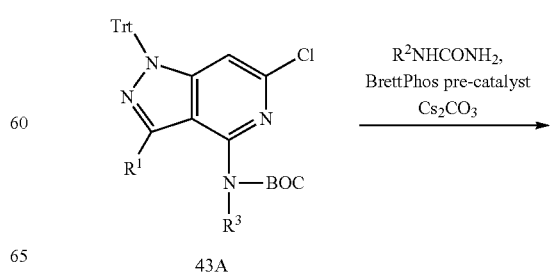

41A

42A

43A

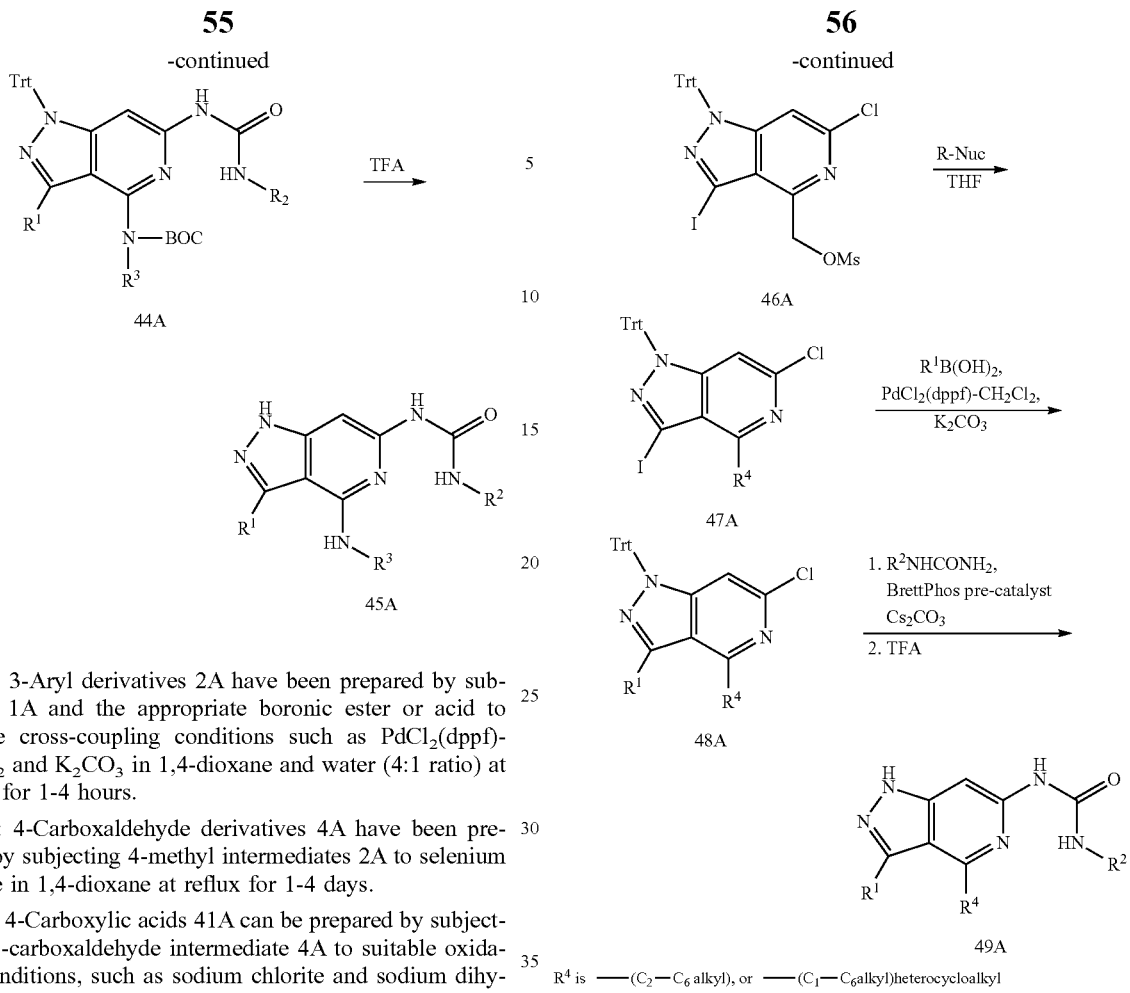

Step 1: 3-Aryl derivatives 2A have been prepared by subjecting 1A and the appropriate boronic ester or acid to suitable cross-coupling conditions such as PdCl$_2$(dppf)-CH$_2$Cl$_2$ and K$_2$CO$_3$ in 1,4-dioxane and water (4:1 ratio) at 80° C. for 1-4 hours.

Step 2: 4-Carboxaldehyde derivatives 4A have been prepared by subjecting 4-methyl intermediates 2A to selenium dioxide in 1,4-dioxane at reflux for 1-4 days.

Step 3: 4-Carboxylic acids 41A can be prepared by subjecting a 4-carboxaldehyde intermediate 4A to suitable oxidation conditions, such as sodium chlorite and sodium dihydrogen phosphate with 2-methyl-2-butyne in THF, t-BuOH, and water at rt for 24 hours.

Step 4: 4-Carboxylic acids 41A have been converted into Boc-protected amines 42A through suitable Curtius Rearrangement conditions such as DPPA, TEA and t-BuOH at 100° C. for 24 hrs.

Step 5: 4-Boc-protected alkylamines 43A have been prepared by treating 42A with the appropriate halide in the presence of a suitable base (i.e. NaH or Cs$_2$CO$_3$) in a suitable solvent (i.e. DMF) at 35-60° C. for 1-4 hrs.

Step 6: Urea derivatives 45A have been prepared by subjecting 43A and the appropriate primary urea to suitable cross-coupling conditions, such as BrettPhos pre-catalyst and Cs$_2$CO$_3$ in 1,4-dioxane at 100° C. for 1 to 16 hr, followed by treatment with TFA and triethylsilane (with or without DCM).

$R^4$ is ——(C$_2$—C$_6$ alkyl), or ——(C$_1$—C$_6$alkyl)heterocycloalkyl

Step 1: 4-methyl mesylate 46A was prepared by subjecting 8A to suitable mesylation conditions such as Mes-Cl and TEA in DCM at rt.

Step 2: 4-Alkyl derivatives 47A have been prepared by stirring at room temperature for 1 h the appropriate nucleophile with 46A (with or without a suitable base) to afford the desired product 47A.

Step 3: 3-Aryl derivatives 48A have been prepared by subjecting 47A and the appropriate boronic ester or acid to suitable cross-coupling conditions such as PdCl$_2$(dppf)-CH$_2$Cl$_2$ and K$_2$CO$_3$ in 1,4-dioxane and water (4:1 ratio) at 80° C. for 1-4 hours.

Step 4: Urea derivatives 49A have been prepared by subjecting 48A and the appropriate primary urea to suitable cross-coupling conditions, such as BrettPhos pre-catalyst and Cs$_2$CO$_3$ in 1,4-dioxane at 100° C. for 1 to 16 hr, followed by treatment with TFA and triethylsilane (with or without DCM).

Scheme 13

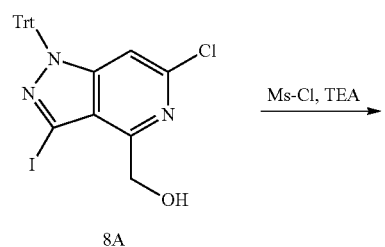

Scheme 14

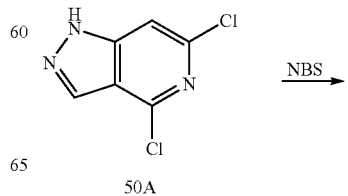

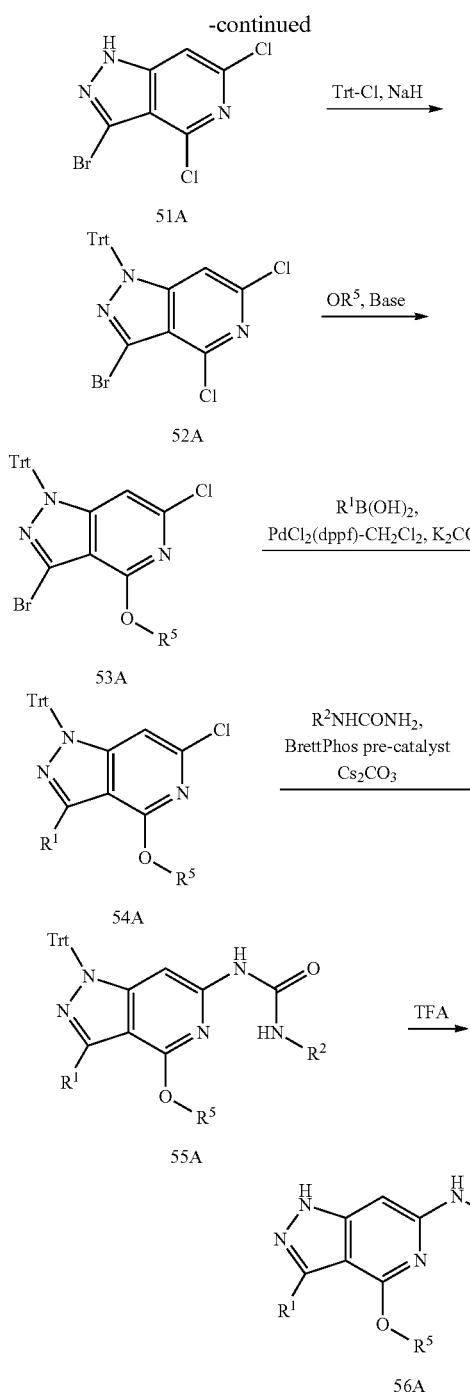

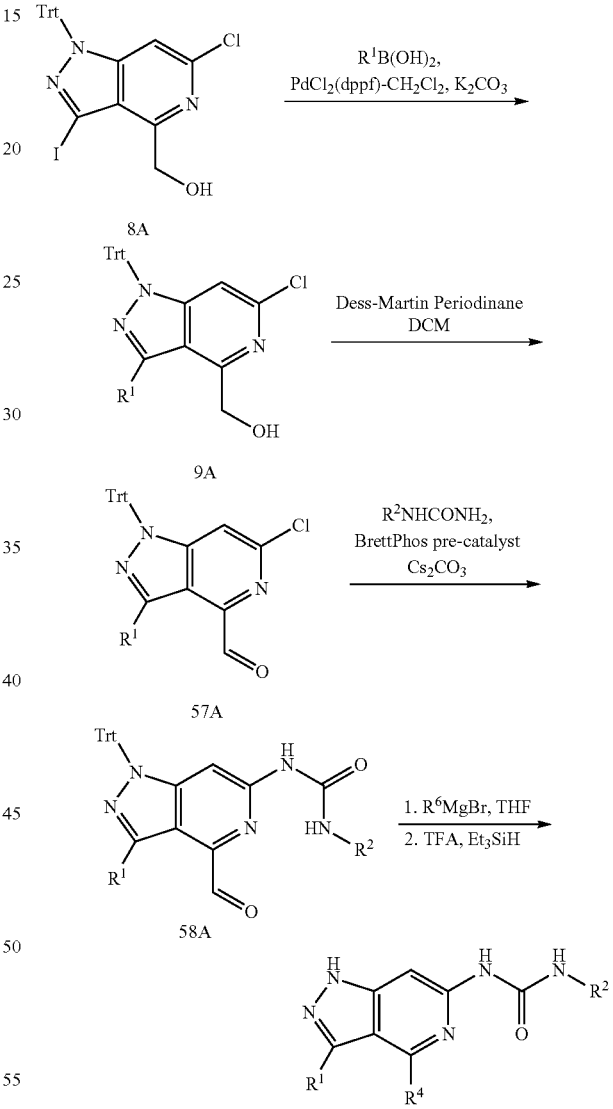

Scheme 15

Step 4: 3-Aryl derivatives 54A have been prepared by subjecting 53A and the appropriate boronic ester or acid to suitable cross-coupling conditions such as PdCl$_2$(dppf)-CH$_2$Cl$_2$ and K$_2$CO$_3$ in 1,4-dioxane and water (4:1 ratio) at 80° C. for 1-4 hours.

Step 5: Urea derivatives 56A have been prepared by subjecting 54A and the appropriate primary urea to suitable cross-coupling conditions, such as BrettPhos pre-catalyst and Cs$_2$CO$_3$ in 1,4-dioxane at 100° C. for 1 to 16 hr, followed by treatment with TFA and triethylsilane (with or without DCM).

Step 1: 3-bromo-4,6-dichloro-1H-pyrazolo[4,3-c]pyridine 51A was prepared by treating 4,6-dichloro-1H-pyrazolo[4,3-c]pyridine 50A to suitable bromination conditions, such as NBS in ACN at 120° C. for 0.5-1 hr.

Step 2: 3-bromo-4,6-dichloro-1-trityl-1H-pyrazolo[4,3-c]pyridine 52A was prepared by treating 51A in the presence of Trt-Cl and a suitable base (i.e. NaH) in a suitable solvent (i.e. DMF).

Step 3: 4-Ether derivatives 53A have been prepared by stirring 52A from 0° C. to rt (from 0.5-2 h) with the appropriate halide in the presence of a suitable base (i.e. NaHMDS).

Step 1: 3-Aryl derivatives 9A have been prepared by subjecting 8A and the appropriate boronic ester or acid to suitable cross-coupling conditions such as PdCl$_2$(dppf)-CH$_2$Cl$_2$ and K$_2$CO$_3$ in 1,4-dioxane and water (4:1 ratio) at 80° C. for 1-4 hours Step 2: 4-Carboxaldehyde derivatives 57A have been prepared by subjecting 9A to suitable oxidation conditions such as Dess-Martin Periodinane in DCM at rt for 1 hr.

Step 3: Urea derivatives 58A have been prepared by subjecting 57A and the appropriate primary urea to suitable cross-coupling conditions, such as BrettPhos pre-catalyst and $Cs_2CO_3$ in 1,4-dioxane at 100° C. for 1 to 16 hr.

Step 4: Secondary alcohol derivatives 59A have been prepared by stirring 59A with the appropriate Grignard in THF at −78° C. to 0° C., followed by treatment with TFA and triethylsilane (with or without DCM) to yield the desired product 60A Intermediate 1A

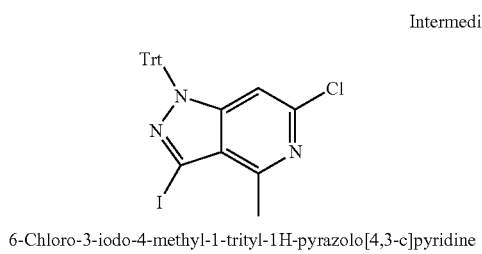

6-Chloro-3-iodo-4-methyl-1-trityl-1H-pyrazolo[4,3-c]pyridine

6-Chloro-3-iodo-4-methyl-1-trityl-1H-pyrazolo[4,3-c]pyridine was synthesized according to the following scheme and procedures.

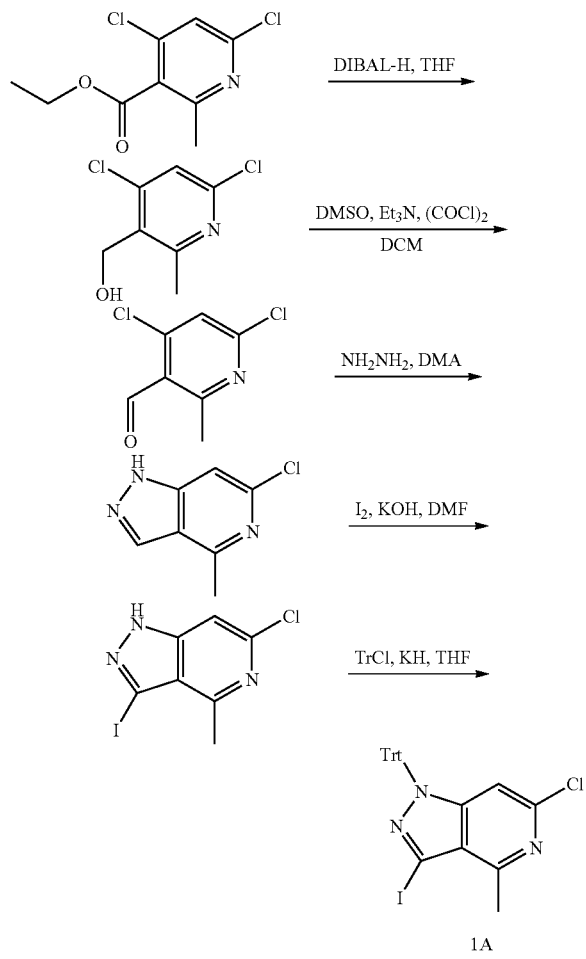

Step 1:
(4,6-Dichloro-2-methylpyridin-3-yl)methanol

THF (52.3 mL) was cooled to 0° C. in a dry round bottomed flask under an atmosphere of $N_2$ gas. Ethyl 4,6-dichloro-2-methylnicotinate (4.60 mL, 26.1 mmol) was then added followed by diisobutylaluminum hydride (57.5 mL, 57.5 mmol). The reaction was stirred at 0° C. for 3 h. The reaction was then poured into cold saturated sodium potassium tartrate solution. The mixture was stirred for several hours to allow the precipitate to dissolve, then the aqueous phase was extracted with EtOAc. The organic layer was dried over magnesium sulfate, filtered, and concentrated in vacuo. The residue was purified by flash chromatography (0-50% EtOAc/hexanes) to give (4,6-dichloro-2-methyl-pyridin-3-yl)methanol. MS ESI calc'd. for $C_7H_8Cl_2NO$ $[M+1]^+$ 192. found 192.

Step 2: 4,6-Dichloro-2-methylnicotinaldehyde

A dry flask was charged with DCM (59.9 mL) and oxalyl chloride (3.15 mL, 35.9 mmol) and cooled to −78° C. Dimethyl sulfoxide (3.40 mL, 47.9 mmol) was added and the reaction was stirred for 30 min. A solution of (4,6-dichloro-2-methylpyridin-3-yl)methanol (4.60 g, 23.95 mmol) in DCM (2 mL) was then added. The reaction was stirred for 30 min then triethylamine (6.74 mL, 71.9 mmol) was added and the reaction mixture was stirred at −78° C. for 30 min. The reaction was warmed to 0° C. and stirred for 1 h. The reaction was then quenched with sodium bicarbonate, diluted with water, and the aqueous layer extracted with EtOAc. The organic phase was washed with sat. sodium bicarbonate, dried over $MgSO_4$, filtered, and concentrated in vacuo to afford 4,6-dichloro-2-methylnicotinaldehyde, which was carried onto the next step without further purification. $^1$H NMR (500 MHz, DMSO-$d_6$) δ 10.60 (s, 1H), 7.37 (s, 1H), 2.80 (s, 3H).

Step 3:
6-Chloro-4-methyl-1H-pyrazolo[4,3-c]pyridine

A solution of 4,6-dichloro-2-methylnicotinaldehyde (5.25 g, 23.48 mmol) in DMA (50 mL) was treated with hydrazine (7.37 mL, 235 mmol) at 0° C. The reaction was stirred for 15 min and then warmed to 80° C. for 2 h. The reaction was cooled and diluted with EtOAc and washed with water. The organic phase was dried over $MgSO_4$, filtered, and concentrated in vacuo. The residue was purified by flash chromatography (0-100% EtOAc/hexanes) to give 6-chloro-4-methyl-1H-pyrazolo[4,3-c]pyridine. MS ESI calc'd. for $C_7H_7ClN_3[M+1]^+$ 168. found 168.

Step 4: 6-Chloro-3-iodo-4-methyl-1H-pyrazolo[4,3-c]pyridine

A 100 mL round bottom flask was charged with 6-chloro-4-methyl-1H-pyrazolo[4,3-c]pyridine (1.20 g, 7.16 mmol) and DMF (28.5 mL). The reaction flask was warmed to 70° C. and KOH (1.2 g, 21.48 mmol) was added. Iodine (5.45 g, 21.48 mmol) was added gradually over 1 h. The reaction mixture was stirred for 3 h then additional KOH (3.2 g, 57.0 mmol) and iodine (15.6 g, 61.5 mmol) were added. The reaction was heated at 70° C. for 2 h. The reaction was poured into saturated sodium thiosulfate (500 mL) and diluted with EtOAc (200 mL). The aqueous phase was extracted with EtOAc (200 mL, ×2). The combined organic phase was washed with water (200 mL) and brine (200 mL), dried over magnesium sulfate, filtered, and concentrated in vacuo to give 6-chloro-3-iodo-4-methyl-1H-pyrazolo[4,3-c]pyridine. MS ESI calc'd. for $C_7H_6ClIN_3$ $[M+1]^+$ 294. found 294.

Step 5: 6-Chloro-3-iodo-4-methyl-1-trityl-1H-pyrazolo[4,3-c]pyridine

A flask containing 6-chloro-3-iodo-4-methyl-1H-pyrazolo[4,3-c]pyridine (2.06 g, 7.02 mmol) in THF (60 mL) was cooled to 0° C. and potassium hydride (1.126 g, 14.04 mmol) was added. The reaction was stirred for 30 min followed by addition of trityl chloride (2.94 g, 10.53 mmol). The reaction mixture was warmed to room temperature and stirred for 4 h. The reaction was poured into sat. sodium bicarbonate and extracted with EtOAc. The organic phase was dried over MgSO4, filtered, and concentrated in vacuo. The residue was purified by flash chromatography (0-10% DCM/EtOAc) to give 6-chloro-3-iodo-4-methyl-1-trityl-1H-pyrazolo[4,3-c]pyridine. MS ESI calc'd. for $C_{26}H_{20}ClIN_3$ $[M+1]^+$ 536. found 536.

Intermediate 8A

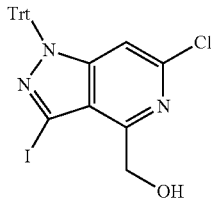

(6-chloro-3-iodo-1-trityl-1H-pyrazolo[4,3-c]pyridin-4-yl)methanol (6-chloro-3-iodo-1-trityl-1H-pyrazolo[4,3-c]pyridin-4-yl)methanol was synthesized according to the following scheme and procedures.

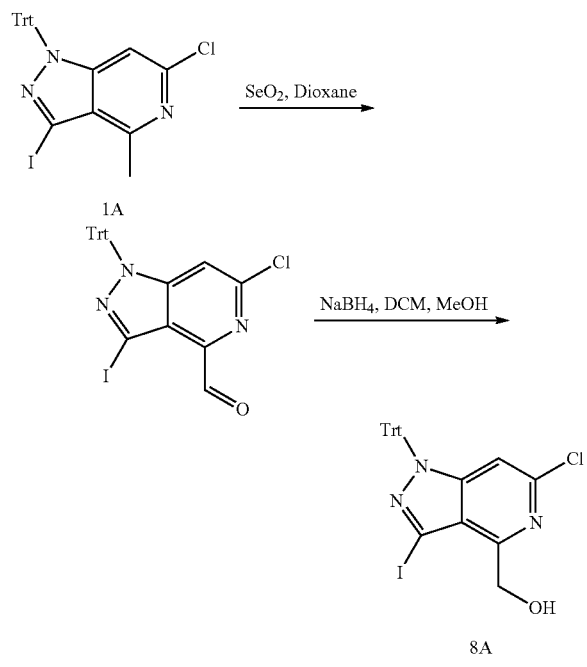

Step 1: 6-Chloro-3-iodo-1-trityl-1H-pyrazolo[4,3-c]pyridine-4-carbaldehyde

6-Chloro-3-iodo-4-methyl-1-trityl-1H-pyrazolo[4,3-c]pyridine (Intermediate 1A; 20 g, 37.3 mmol) was dissolved in dioxane (400 mL) and selenium dioxide (12.43 g, 112 mmol) was added. The reaction mixture was stirred at 100° C. for 6 hrs. Selenium dioxide (4.14 g, 37.3 mmol) was added and the reaction mixture continued stirring at 100° C. overnight. The reaction was filtered over celite, rinsed with DCM, and concentrated in vacuo. The residue was dissolved in DCM (1.0 L) and filtered over celite for a second time. The material was concentrated in vacuo while loading onto silica gel. Purification by flash chromatography (0-5% DCM/EtOAc) gave 6-chloro-3-iodo-1-trityl-1H-pyrazolo[4,3-c]pyridine-4-carbaldehyde. $^1$H NMR (500 MHz, DMSO-$d_6$) δ 10.54 (s, 1H), 7.39-7.35 (m, 10H), 7.17-7.11 (m, 5H), 6.29 (s, 1H).

Step 2: (6-Chloro-3-iodo-1-trityl-1H-pyrazolo[4,3-c]pyridin-4-yl)methanol

6-Chloro-3-iodo-1-trityl-1H-pyrazolo[4,3-c]pyridine-4-carbaldehyde (10.26 g, 18.66 mmol) was dissolved in DCM (250 mL) and methanol (125 mL). The reaction mixture was then cooled to 0° C. and sodium borohydride (0.706 g, 18.66 mmol) was added. The reaction mixture was stirred at room temperature for 15 min. The reaction was quenched with water and extracted with DCM. The combined organic layers were washed with brine, dried over sodium sulfate, filtered, and concentrated in vacuo while loading on silica gel. Purification by flash chromatography (2-10% DCM/EtOAc) gave (6-chloro-3-iodo-1-trityl-1H-pyrazolo[4,3-c]pyridin-4-yl)methanol. MS ESI calc'd. for $C_{26}H_{20}ClN_3O$ $[M+1]^+$ 552. found 552.

Intermediate 16A

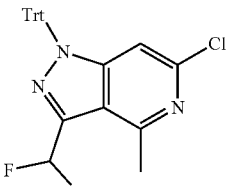

6-chloro-3-(diflouromethyl)-4-methyl-1-trityl-1H-pyrazolo[4,3-c]pyridine 6-chloro-3-(difluoromethyl)-4-methyl-1-trityl-1H-pyrazolo[4,3-c]pyridine was synthesized according to the following schemes (A and B) and procedures.

Scheme A:

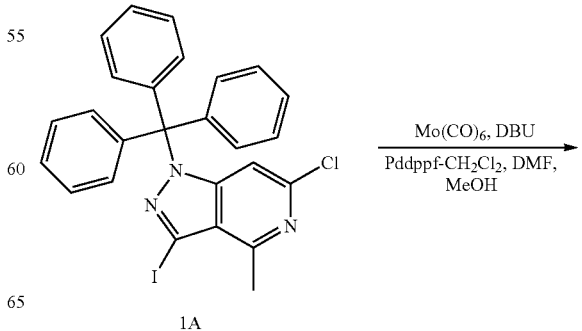

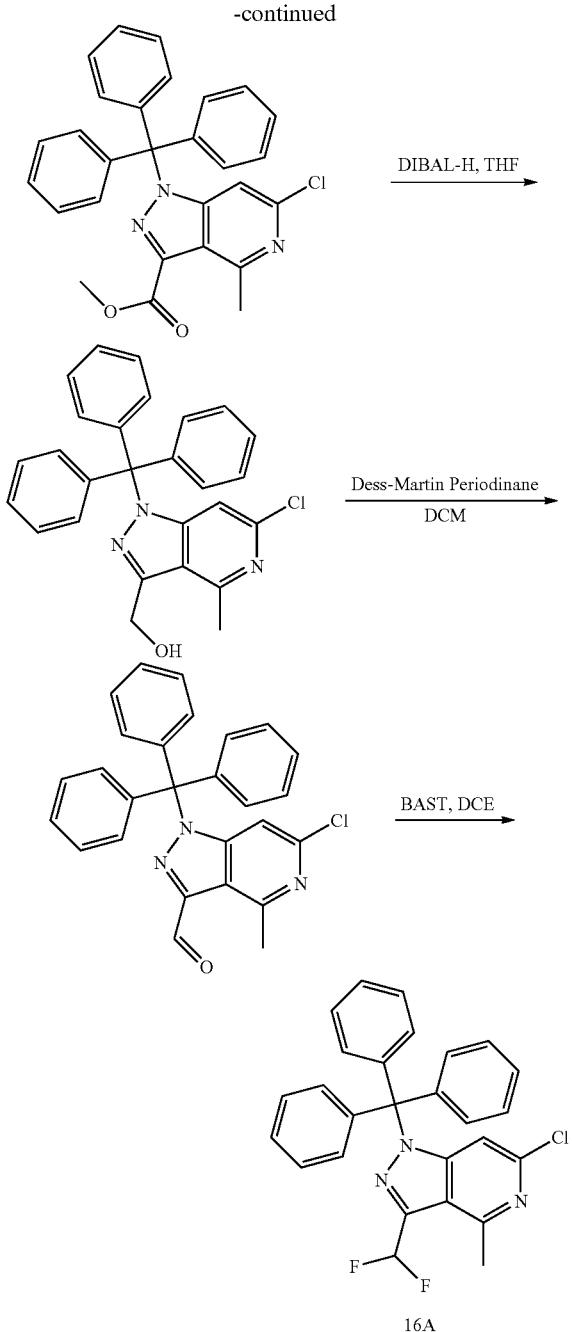

Scheme A

Step 1: methyl 6-chloro-4-methyl-1-trityl-1H-pyrazolo[4,3-c]pyridine-3-carboxylate A mixture of 6-chloro-3-iodo-4-methyl-1-trityl-1H-pyrazolo[4,3-c]pyridine (Intermediate 1A, 5.0 g, 9.33 mmol), molybdenum hexacarbonyl (3.70 g, 14.00 mmol) and 1,1'-bis(diphenylphosphino)ferrocene-palladium(II)dichloride dichloromethane complex (2.286 g, 2.80 mmol) in DMF (25 ml) and MeOH (25 ml) was sparged with argon, charged with DBU (4.22 ml, 28.0 mmol), sealed, and heated to 50° C. for 24 hrs. The reaction mixture was filtered through celite, washed with EtOAc, concentrated in vacuo and purified via flash chromatography 0-50% EtOAc/Hexanes to provide methyl 6-chloro-4-methyl-1-trityl-1H-pyrazolo[4,3-c]pyridine-3-carboxylate. MS ESI calc'd. for $C_{28}H_{23}ClN_3O_2$ [M+1]$^+$ 468. found 468.

Step 2: (6-chloro-4-methyl-1-trityl-1H-pyrazolo[4,3-c]pyridin-3-yl)methanol

A dry flask was charged with methyl 6-chloro-4-methyl-1-trityl-1H-pyrazolo[4,3-c]pyridine-3-carboxylate (1.42 g, 3.03 mmol) and THF (30.3 ml) and was cooled to −78° C. DIBAL-H (9.10 ml, 9.10 mmol) was added dropwise. The mixture was stirred at −78° C. for 2 hrs and was then allowed to reach 0° C. While stirring at 0° C., MeOH (10 mL) was added slowly, stirred at 0° C. for 10 min. Aqueous Potassium Sodium Tartrate (Rochelle's salt) (saturated, 60 mL) was added, followed by EtOAc (100 mL), and the biphasic mixture was stirred at room temperature for 20 min. The aqeuous phase was separated and was extracted with EtOAc (1×100 mL). The combined organic layers were washed with brine (saturated, 1×100 mL), dried (MgSO$_4$), and filtered. The mixture was then concentrated in vacuo while loading onto silica gel. Purification by MPLC 0-35% EtOAc/Hexanes gave (6-chloro-4-methyl-1-trityl-1H-pyrazolo[4,3-c]pyridin-3-yl)methanol. MS ESI calc'd. for $C_{27}H_{23}ClN_3O$ [M+1]$^+$ 440. found 440.

Step 3: 6-chloro-4-methyl-1-trityl-1H-pyrazolo[4,3-c]pyridine-3-carbaldehyde (6-chloro-4-methyl-1-trityl-1H-pyrazolo[4,3-c]pyridin-3-yl)methanol (1.10 g, 2.50 mmol) was taken up in DCM (25.0 ml) and Dess-MartinPeriodinane (1.27 g, 3.00 mmol) was added. The reaction was allowed to stir at room temperature for 1 hr. The reaction mixture was diluted with DCM (20 mL) and 1N NaOH was added (15 ml) and the mixture was allowed to stir. The phases were separated and the aqueous phase was washed with DCM (3×). The combined organic layers were washed with brine, dried over MgSO$_4$, and concentrated in vacuo to give 6-chloro-4-methyl-1-trityl-1H-pyrazolo[4,3-c]pyridine-3-carbaldehyde. MS ESI calc'd. for $C_{27}H_{21}ClN_3O$ [M+1]$^+$ 438. found 438.

Step 4: 6-chloro-3-(difluoromethyl)-4-methyl-1-trityl-1H-pyrazolo[4,3-c]pyridine Bis(2-methoxymethyl)aminosulfur trifluoride (3957 µl, 21.47 mmol) was added dropwise to a solution of 6-chloro-4-methyl-1-trityl-1H-pyrazolo[4,3-c]pyridine-3-carbaldehyde (940 mg, 2.147 mmol) in DCE (1.1 ml) at room temperature. The resulting mixture was allowed to stir at 65° C. for 3 hrs. The reaction mixture was cooled to 0° C. and was poured into a flask containing 100 ml of saturated NaHCO$_3$ at 0° C. EtOAc was added and the mxiture was stirred in the icebath for 20 mins until bubbling ceased. Once quenched, the desired products were extracted into EtOAc (3×). The combined organic layers were washed with brine, dried over MgSO$_4$, and concentrated in vacuo while loading onto silica gel. Purification by MPLC 0-25% EtOAc/ hexanes gave 6-chloro-3-(difluoromethyl)-4-methyl-1-trityl-1H-pyrazolo[4,3-c]pyridine 16A. MS ESI calc'd. for $C_{27}H_{21}ClF_2N_3$ [M+1]$^+$ 460. found 460.

Scheme B:

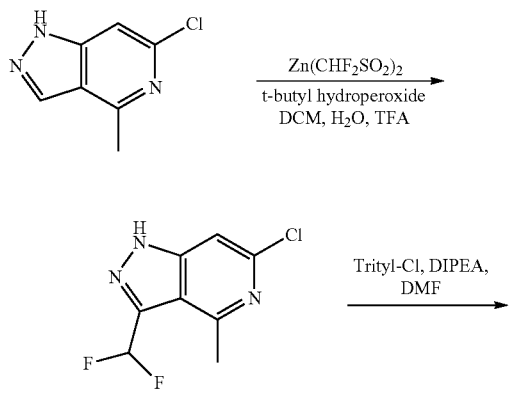

Step 1: 6-chloro-3-(difluoromethyl)-4-methyl-1H-pyrazolo[4,3-c]pyridine 6-chloro-4-methyl-1H-pyrazolo[4,3-c]pyridine (400 mg, 2.387 mmol), bis((difluoromethyl)sulfonyl)zinc (1410 mg, 4.77 mmol) were added to a 4 ml microwave vial, charged with DCM (8 ml), water (4 ml), TFA (0.184 ml, 2.387 mmol) and cooled to 0° C. tert-butyl hydroperoxide (1.70 ml, 11.93 mmol) was added dropwise, the icebath was removed, and the reaction was allowed to stir for 72 h at room temperature. The reaction was diluted with water and 25 ml DCM/MeOH 10:1, and filtered through celite. The organic layer was washed with brine and concentrated in vacuo. The residue was purified on silica gel 10-50% EtOAc//DCM to provide 6-chloro-3-(difluoromethyl)-4-methyl-1H-pyrazolo[4,3-c]pyridine. MS ESI calc'd. for $C_8H_7ClF_2N_3$ [M+1]$^+$ 218. found 218.

Step 2: 6-chloro-3-(difluoromethyl)-4-methyl-1-trityl-1H-pyrazolo[4,3-c]pyridine 6-chloro-3-(difluoromethyl)-4-methyl-1H-pyrazolo[4,3-c]pyridine (115 mg, 0.528 mmol) was dissolved in THF (4 ml), charged with trityl chloride (177 mg, 0.634 mmol) and DIPEA (0.138 ml, 0.793 mmol) and the reaction mixture was allowed to stir at rt for 1 hr. A second portion of DIPEA (0.138 ml, 0.793 mmol) and trityl chloride (177 mg, 0.634 mmol) was added and the reaction was allowed to stir at ambient temperature for 20 minutes. The reaction was quenched with water and the precipitate formed was collected via filtration, washed with water, dried under high vacuum and used without further purification crude 16A. MS ESI calc'd. for $C_{27}H_{21}ClF_2N_3$ [M+1]$^+$ 460. found 460.

Intermediate 27A

1-(6-chloro-4-(hydroxymethyl)-1-trityl-1H-pyrazolo[4,3-c]pyridin-3-yl)ethanone 1-(6-chloro-4-(hydroxymethyl)-1-trityl-1H-pyrazolo[4,3-c]pyridin-3-yl)ethanone was synthesized according to the following scheme and procedures.

Step 1: 1-(6-chloro-4-(hydroxymethyl)-1-trityl-1H-pyrazolo[4,3-c]pyridin-3-yl)ethanone A suspension of Intermediate 8A, tetrakis(triphenylphosphine)palladium(0) (88 mg, 0.076 mmol), lithium chloride (81 mg, 1.903 mmol) and tributyl(1-ethoxyvinyl)tin (0.386 ml, 1.142 mmol) in DMF (8.0 ml) was degassed and backfilled with nitrogen gas, sealed, and heated at 80° C. for 18 hrs. After cooling to ambient temperature, 3 mL of 1N HCL was added. The reaction mixture was stirred at ambient temperature for 4 hrs. The reaction contents were extracted with EtOAc and washed with aq. NaHCO$_3$, dried with Na$_2$SO$_4$ and concentrated in vacuo. Purification by column chromatography eluting from 0-30% EtOAc/Hexanes gave 1-(6-chloro-4-(hydroxymethyl)-1-trityl-1H-pyrazolo[4,3-c]pyridin-3-yl)ethanone (Intermediate 27A). MS ESI calc'd. for $C_{28}H_{23}ClN_3O_2$[M+1]$^+$ 468. found 468.

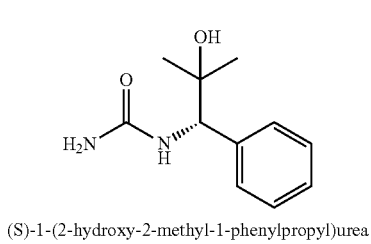

(S)-1-(2-hydroxy-2-methyl-1-phenylpropyl)urea (S)-1-(2-hydroxy-2-methyl-1-phenylpropyl)urea was synthesized according to the following scheme and procedures.

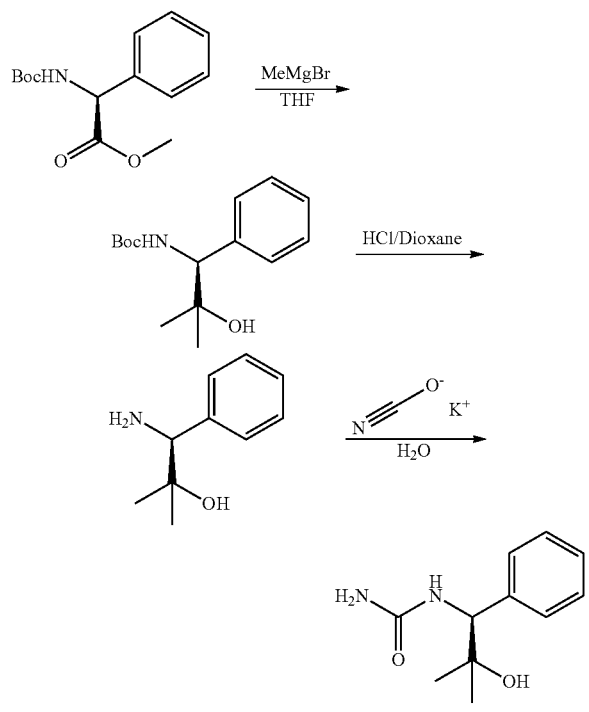

60A

Step 1: (S)-tert-butyl (2-hydroxy-2-methyl-1-phenylpropyl)carbamate

At 0° C., to a solution of (S)-methyl 2-((tert-butoxycarbonyl)amino)-2-phenylacetate 1 (4.0 g, 15 mmol) in THF (40 mL) was added MeMgBr (3 M solution in THF, 20 mL, 60 mmol) dropwise and the contents were stirred at ambient temperature. After 2 h, the reaction was carefully quenched with aqueous saturated $NH_4Cl$ (20 mL) and the organic contents were extracted with EtOAc (2×50 mL). The EtOAc layer was washed successively with $H_2O$ (2×10 mL), brine (1×20 mL) and the volatiles were removed under reduced pressure to afford (S)-tert-butyl (2-hydroxy-2-methyl-1-phenylpropyl)carbamate. The residue thus obtained was pure enough and is taken directly for the next step.

Step 2: (S)-1-amino-2-methyl-1-phenylpropan-2-ol

To a solution of (S)-tert-butyl (2-hydroxy-2-methyl-1-phenylpropyl)carbamate (3.5 g, 13 mmol) in $CH_2Cl_2$ (20 mL) was added dioxane saturated with HCl gas (10 mL) and the contents were stirred at ambient temperature for 30 min. The volatiles were then removed under reduced pressure and the residue thus obtained was triturated with $Et_2O$ to afford (S)-1-amino-2-methyl-1-phenylpropan-2-ol. $^1H$ NMR (300 MHz, DMSO-$d_6$) δ 8.3 (bs, 2H), 7.47-7.37 (m, 5H), 5.34 (s, 1H), 4.1 (bs, 1H), 1.17 (s, 3H), 0.97 (s, 3H). Anal. Calcd. $C_{10}H_{15}NO$ 165.2. Found 166.2 (M+H).

Step 3: (S)-1-(2-hydroxy-2-methyl-1-phenylpropyl)urea

To a solution of (S)-1-amino-2-methyl-1-phenylpropan-2-ol (2.0 g, 10 mmol) in $H_2O$ (10 mL) was added potassium cyanate (0.85 g, 12 mmol) and the contents were stirred at ambient temperature for 2 h. The solid thus obtained was filtered and washed successively with $H_2O$ (2×5 mL) and dried in air to afford (S)-1-(2-hydroxy-2-methyl-1-phenylpropyl)urea, Intermediate 60A. $^1H$ NMR (400 MHz, DMSO-$d_6$) δ 7.25-7.15 (m, 5H), 6.52 (d, J=9.2 Hz, 1H), 5.50 (s, 2H), 4.50 (s, 1H), 4.41 (d, J=9.2 Hz, 1H), 1.10 (s, 3H), 0.93 (s, 3H). Anal. Calcd. $C_{11}H_{16}N_2O_2$ 208.3. Found 209.2 (M+H).

Intermediates 61A (Table 1) were prepared following similar procedures described for Intermediate 60A using the appropriate boc-protected amino ester, which can be achieved by those of ordinary skill in the art of organic synthesis.

TABLE 1

| Intermediate | Structure | IUPAC Name | Exact Mass [M + H]+ |
|---|---|---|---|
| 61A | 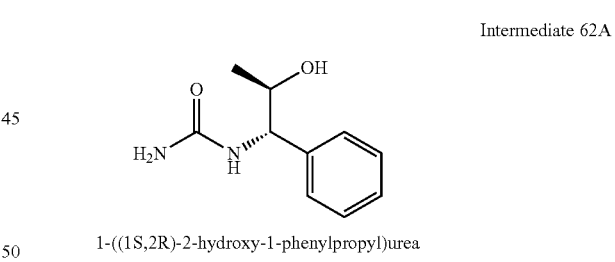 | (S)-1-(1-(4-fluorophenyl)-2-hydroxy-2-methylpropyl)urea | Calc'd 227, found 213 |

Intermediate 62A

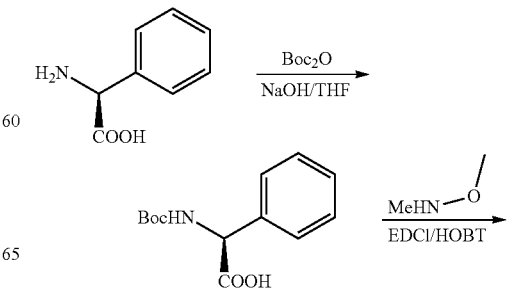

1-((1S,2R)-2-hydroxy-1-phenylpropyl)urea 1-((1S,2R)-2-hydroxy-1-phenylpropyl)urea was synthesized according to the following scheme and procedures.

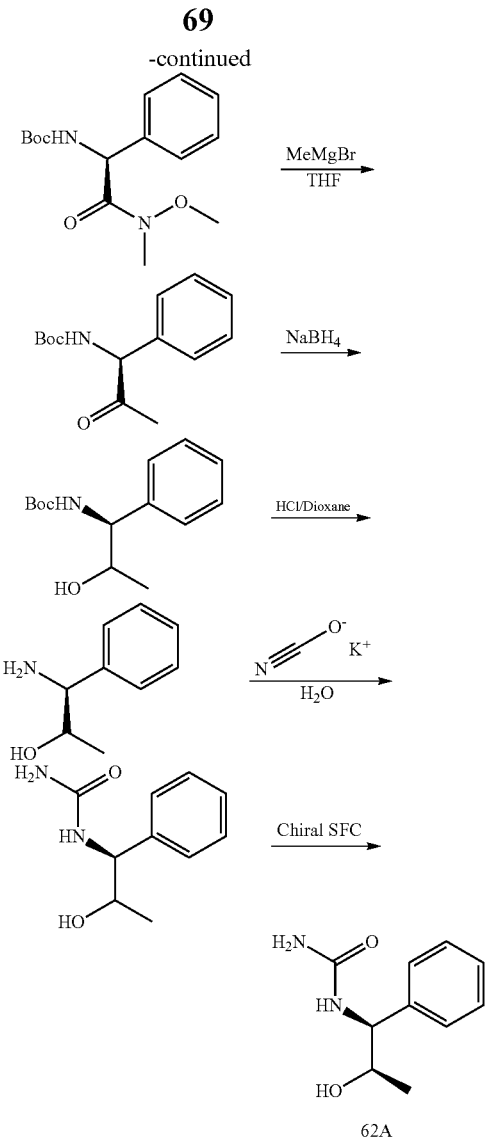

62A

Step 1: (S)-2-((tert-butoxycarbonyl)amino)-2-phenylacetic acid

At 0° C., to a solution of (S)-2-amino-2-phenylacetic acid (3.0 g, 19.9 mmol) in THF (20 mL) were added 10% NaOH solution (20 mL, 50 mmol) and Boc$_2$O (4.8 g, 22 mmol) and the contents were stirred at ambient temperature. After 3 hr, the reaction mixture was cooled to 0° C. and was acidified carefully with 50% citric acid solution (10 mL) until the pH of the solution is 4. The organic contents were extracted with EtOAc (3×25 mL) and the combined organic extracts were washed with brine (1×20 mL), dried over Na$_2$SO$_4$, concentrated to afford (S)-2-((tert-butoxycarbonyl)amino)-2-phenylacetic acid. The residue thus obtained was taken directly for step 2 without further purification. MS ESI calc'd. for C$_{13}$H$_{18}$NO$_4$ [M+1]$^+$ 252. found 252.2.

Step 2: (S)-tert-butyl (2-(methoxy(methyl)amino)-2-oxo-1-phenylethyl)carbamate

To a solution of (S)-2-((tert-butoxycarbonyl)amino)-2-phenylacetic acid (1.0 g, 4.0 mmol) in dichloromethane (10 mL) were added N,O-dimethyl hydroxylamine hydrochloride (0.77 g, 8.0 mmol), EDCI (1.2 g, 6.0 mmol), HOBt (0.05 g, 0.4 mmol), Et$_3$N (0.8 g, 8.0 mmol) and the contents were stirred at ambient temperature. After 2 hr, the reaction was quenched with ice cold H$_2$O (10 mL), and the organic contents were extracted with CH$_2$Cl$_2$ (2×30 mL). The combined organic extracts were washed with brine (1×20 mL), dried over Na$_2$SO$_4$, concentrated and the residue thus obtained was purified by flash column chromatography to afford (S)-tert-butyl (2-(methoxy(methyl)amino)-2-oxo-1-phenylethyl)carbamate. $^1$H NMR (300 MHz, CDCl$_3$) δ 7.39-7.29 (m, 5H), 5.77 (bs, 1H), 5.73 (bs, 1H), 3.47 (s, 3H), 3.20 (s, 3H), 1.42 (s, 9H).

Step 3: ((S)-tert-butyl (2-oxo-1-phenylpropyl)carbamate

At 0° C., to a solution of (S)-tert-butyl (2-(methoxy(methyl)amino)-2-oxo-1-phenylethyl)carbamate (0.9 g, 3.06 mmol) in anhydrous THF (15 mL), was added MeMgBr (3M solution in Et$_2$O, 2.0 mL, 6.1 mmol) and resultant mixture was allowed to warm and stirred at ambient temperature. After 2 hrs, the reaction was carefully quenched with saturated aqueous NH$_4$Cl solution (10 mL), and the organic contents were extracted with CH$_2$Cl$_2$ (3×25 mL). The volatiles were removed under reduced pressure to afford (S)-tert-butyl (2-oxo-1-phenylpropyl)carbamate. The compound obtained is pure and no further purification is necessary. $^1$H NMR (300 MHz, CDCl$_3$) δ 7.40-7.33 (m, 5H), 5.88 (bs, 1H), 5.28 (bs, 1H), 2.08 (s, 3H), 1.41 (s, 9H).

Step 4: tert-butyl ((1S)-2-hydroxy-1-phenylpropyl)carbamate

At 0° C., to a solution of ((S)-tert-butyl (2-oxo-1-phenylpropyl)carbamate (0.7 g, 2.8 mmol) in MeOH (10 mL) was added NaBH$_4$ (0.1 g, 2.8 mmol) and the contents were stirred at ambient temperature. After 30 min, the reaction mixture was quenched carefully with ice cold H$_2$O (10 mL), and the organic contents were extracted with EtOAc (3×25 mL). The combined organic extracts were washed with brine (1×20 mL), dried over Na$_2$SO$_4$, concentrated to afford tert-butyl ((1S)-2-hydroxy-1-phenylpropyl)carbamate. The product thus obtained was pure and taken directly for the next step without further purification. MS ESI calc'd. for C$_{14}$H$_{22}$NO$_3$ [M+1]$^+$ 252. found 152.2 [(M+H)-Boc]. [M+1]$^+$ 252. found 252.2

Step 5: tert-butyl ((1S)-2-hydroxy-1-phenylpropyl)carbamate

A solution of tert-butyl ((1S)-2-hydroxy-1-phenylpropyl)carbamate (0.68 g, 2.7 mmol) in dioxane (2 mL) was added dioxane saturated with HCl (3 mL) and the contents were allowed to stir and ambient temperature. After 30 min, the volatiles were removed under reduced pressure. The residue thus obtained was triturated with Et$_2$O to afford tert-butyl ((1S)-2-hydroxy-1-phenylpropyl)carbamate. MS ESI calc'd. for C$_9$H$_{14}$NO [M+1]$^+$ 152.2. found 152.

Steps 6: 1-((1S)-2-hydroxy-1-phenylpropyl)urea

To a solution of (1S)-1-amino-1-phenylpropan-2-ol (0.43 g, 2 mmol) in H$_2$O (2 mL) was added potassium cyanate (0.23 g, 2.7 mmol) and the contents were stirred at ambient temperature for 2 hr. The solid thus obtained was filtered and washed successively with H$_2$O (2×5 mL) and dried in air to afford 1-((1S)-2-hydroxy-1-phenylpropyl)urea. MS ESI calc'd. for $C_{10}H_{15}N_2O_2$ [M+1]$^+$ 195.2. found 195.

Step 7: 1-((1S,2R)-2-hydroxy-1-phenylpropyl)urea and 1-((1S,2S)-2-hydroxy-1-phenylpropyl)urea The enantiomers of 1-((1S)-2-hydroxy-1-phenylpropyl)urea (2.86 g, 14.72 mmol) were separated by SFC (Thar 80, Column: Phenomenex Lux-4 21×250 (mm), UV wavelength: 220 nM, mobile phase: 25:75 Ethanol+0.25% dimethyl ethyl amine in $CO_{2(1)}$, flow rate: 70 mL/min, Run Time: 7.1 min). The fractions were collected and the solvent evaporated in vacuo to afford 1-((1S,2R)-2-hydroxy-1-phenylpropyl)urea. MS ESI calc'd. for $C_{10}H_{15}N_2O_2$ [M+1]$^+$ 195. found 195 (Intermediate 62A).

Intermediates 63A (Table 2) were prepared following similar procedures described for Intermediate 62A using the appropriate amino acid, which can be achieved by those of ordinary skill in the art of organic synthesis.

TABLE 2

| Intermediate | Structure | IUPAC Name | Exact Mass [M + H]+ |
|---|---|---|---|
| 63A | 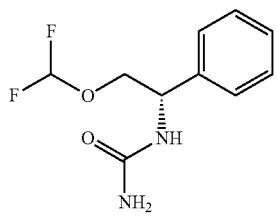 | 1-((1S,2R)-1-(4-fluorophenyl)-2-hydroxypropyl)urea | Calc'd 213, found 213 |

Intermediate 64A

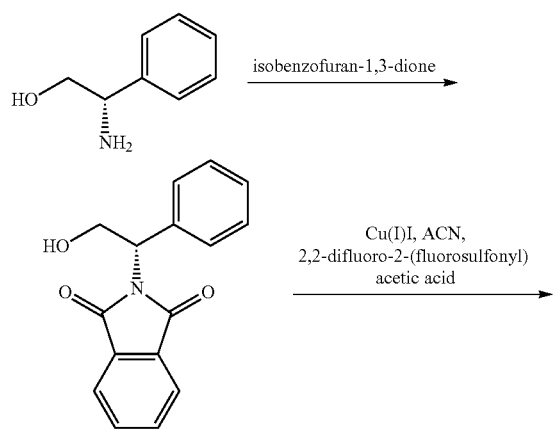

(S)-1-(2-(difluoromethoxy)-1-phenylethyl)urea (S)-1-(2-(difluoromethoxy)-1-phenylethyl)urea was synthesized according to the following scheme and procedures.

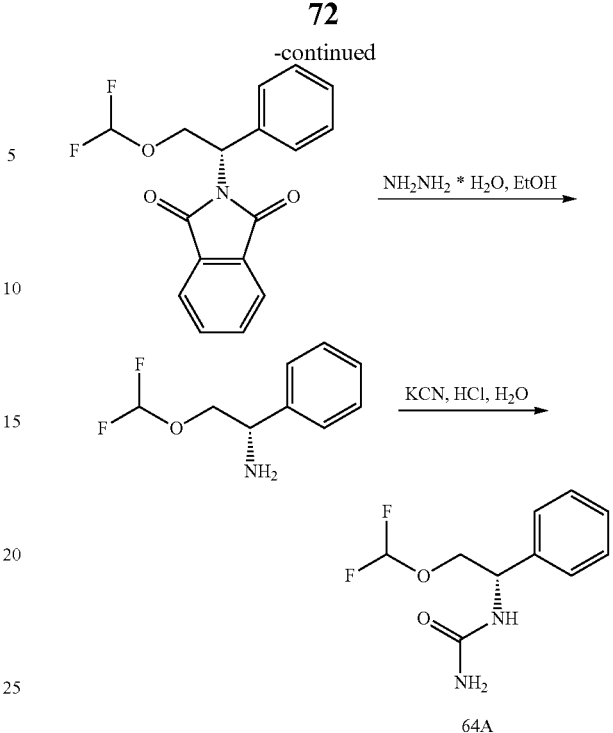

Step 1: (S)-2-(2-hydroxy-1-phenylethyl)isoindoline-1,3-dione (S)-2-amino-2-phenylethanol (2 g, 14.58 mmol) and isobenzofuran-1,3-dione (2.267 g, 15.31 mmol) were combined in a 20 mL microwave tube, sealed and heated to 150° C. for 6 hrs. The tube was cooled to ambient temperature, diluted with DCM, loaded directly onto a 50 g SNAP column and purified 10-60% hexane/EtOAc to provide (S)-2-(2-hydroxy-1-phenylethyl)isoindoline-1,3-dione. MS ESI calc'd. for $C_{16}H_{14}NO_3$ [M+1]$^+$ 268. found 268.

Step 2: (S)-2-(2-(difluoromethoxy)-1-phenylethyl)isoindoline-1,3-dione (S)-2-(2-hydroxy-1-phenylethyl)isoindoline-1,3-dione (1.06 g, 3.97 mmol) was dissolved in anhydrous acetonitrile (20 ml), charged with copper (I) iodide (1.133 g, 5.95 mmol), 2,2-difluoro-2-(fluorosulfonyl)acetic acid (0.615 ml, 5.95 mmol), degassed under nitrogen and heated to 80° C. The solution was allowed to stir at 80° C. for 1 hr. The reaction was cooled in an ice bath, quenched with 5 mL water, filtered through a 10 g celite cartridge, and the solvents were removed in vacuo. The residue was purified by MPLC 10-50% EtOAc/hexanes to provide (S)-2-(2-(difluoromethoxy)-1-phenylethyl)isoindoline-1,3-dione. MS ESI calc'd. for $C_{17}H_{14}F_2NO_3$ [M+1]$^+$ 318. found [M+Na] 340.

Step 3: (S)-2-(difluoromethoxy)-1-phenylethanamine (S)-2-(2-(difluoromethoxy)-1-phenylethyl)isoindoline-1,3-dione (659 mg, 2.077 mmol) was dissolved in EtOH (7 ml), charged with hydrazine hydrate (1.01 ml, 20.77 mmol) and heated to 85° C. for 90 minutes. The reaction was diluted with 10 mL EtOH, filtered, and the solvents were evaporated in vacuo. The residue was purified on silica gel 2-10% MeOH/DCM to provide (S)-2-(difluoromethoxy)-1-phenylethanamine. MS ESI calc'd. for $C_9H_{12}F_2NO$ $[M+1]^+$ 188. found 188.

Step 4: (S)-1-(2-(difluoromethoxy)-1-phenylethyl)urea

To a solution of (S)-2-(difluoromethoxy)-1-phenylethanamine (169 mg, 0.903 mmol) in water (6 ml), was added 1N HCl (3.6 ml, 3.61 mmol) and potassium cyanate (366 mg, 4.51 mmol). The reaction was heated at 80° C. for 2 hrs, then allowed to cool to ambient temperature overnight. The precipitate formed was filtered, washed with water, and dried under high vacuum to provide (S)-1-(2-(difluoromethoxy)-1-phenylethyl)urea (Intermediate 64A). MS ESI calc'd. for $C_{10}H_{13}F_2N_2O_2[M+1]^+$ 231. found 231. $^1H$ NMR (500 MHz, DMSO-$d_6$) δ 7.42-7.30 (m, 4H), 7.29-7.17 (m, 1H), 6.84-6.45 (m, 2H), 5.61 (s, 2H), 4.97-4.83 (m, 1H), 4.08-3.89 (m, 2H).

EXAMPLES

The following examples were prepared according to scheme 1.

Example 1

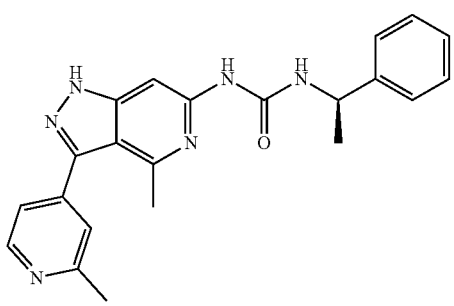 [SMILES: Cc1cc(-c2n[nH]c3cc(NC(=O)N[C@H](C)c4ccccc4)nc(C)c23)ccn1]

(R)-1-(4-Methyl-3-(2-methylpyridin-4-yl)-1H-pyrazolo[4,3-c]pyridin-6-yl)-3-(1-phenylethyl)urea

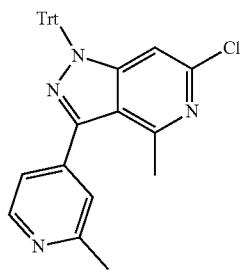

Step 1: 6-Chloro-4-methyl-3-(2-methylpyridin-4-yl)-1-trityl-1H-pyrazolo[4,3-c]pyridine 6-Chloro-3-iodo-4-methyl-1-trityl-1H-pyrazolo[4,3-c]pyridine (Intermediate 1A; 200 mg, 0.373 mmol), 1,1'-bis(diphenylphosphino)ferrocene-palladium(II)dichloride dichloromethane complex (45.7 mg, 0.056 mmol), 2-methylpyridine-4-boronic acid (77 mg, 0.560 mmol), and potassium carbonate (155 mg, 1.120 mmol) were dissolved in water (0.5 mL) and dioxane (2 mL). The vial was degassed with argon for 5 min, sealed, and the reaction stirred at 80° C. for 2 hrs. The reaction mixture was diluted with EtOAc and washed with sat. ammonium chloride and brine. The organic layer was dried over sodium sulfate, filtered, and concentrated in vacuo while loading onto silica gel. Purification by flash chromatography (7-70% EtOAc/Hexanes) gave 6-chloro-4-methyl-3-(2-methylpyridin-4-yl)-1-trityl-1H-pyrazolo[4,3-c]pyridine. MS ESI calc'd. for $C_{32}H_{26}ClN_4$ $[M+1]^+$ 501. found 501.

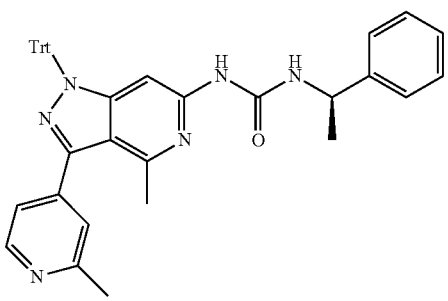

Step 2: (R)-1-(4-Methyl-3-(2-methylpyridin-4-yl)-1-trityl-1H-pyrazolo[4,3-c]pyridin-6-yl)-3-(1-phenylethyl)urea 6-Chloro-4-methyl-3-(2-methylpyridin-4-yl)-1-trityl-1H-pyrazolo[4,3-c]pyridine (62.9 mg, 0.126 mmol), (R)-1-(1-phenylethyl)urea (30.9 mg, 0.188 mmol), brettphos palladacycle (10.03 mg, 0.013 mmol), and cesium carbonate (106 mg, 0.326 mmol) were dissolved in dioxane (1.2 mL). The vial was degassed with argon for 5 min, sealed, and the reaction stirred at 100° C. for 6 hrs. (R)-1-(1-phenylethyl)urea (15.0 mg, 0.09 mmol), brettphos palladacycle (5.0 mg, 0.006 mmol), and cesium carbonate (53 mg, 0.163 mmol) were added and the reaction mixture stirred for another 2 hrs at 100° C. The reaction mixture was filtered through celite, eluting with MeOH, and the filtrate was concentrated in vacuo while loading onto silica gel. Purification by flash chromatography 10-80% EtOAc/Hexanes gave (R)-1-(4-methyl-3-(2-methylpyridin-4-yl)-1-trityl-1H-pyrazolo[4,3-c]pyridin-6-yl)-3-(1-phenylethyl)urea. MS ESI calc'd. for $C_{41}H_{37}N_6O$ $[M+1]^+$ 629. found 629.

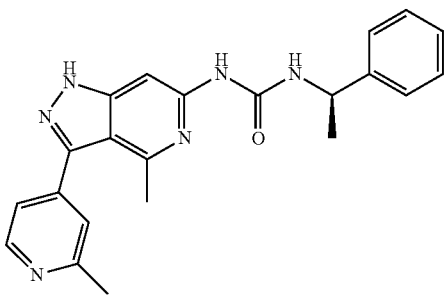 [SMILES: Cc1cc(-c2n[nH]c3cc(NC(=O)N[C@H](C)c4ccccc4)nc(C)c23)ccn1]

Step 3: (R)-1-(4-Methyl-3-(2-methylpyridin-4-yl)-1H-pyrazolo[4,3-c]pyridin-6-yl)-3-(1-phenylethyl)urea (R)-1-(4-Methyl-3-(2-methylpyridin-4-yl)-1-trityl-1H-pyrazolo[4,3-c]pyridin-6-yl)-3-(1-phenylethyl)urea (29.8 mg, 0.047 mmol) was dissolved in TFA (0.5 mL) and triethylsilane (0.030 mL, 0.188 mmol) was added. The reaction mixture was stirred at room temperature for 15 min. The mixture was then concentrated in vacuo. The resulting oil was taken up in EtOAc and saturated NaHCO$_3$ was added. The combined organic layers were dried over Na$_2$SO$_4$, filtered, and concentrated in vacuo while loading onto silica gel. Purification of the residue by flash chromatography 2-20% CH$_2$Cl$_2$/MeOH gave (R)-1-(4-methyl-3-(2-methylpyridin-4-yl)-1H-pyrazolo[4,3-c]pyridin-6-yl)-3-(1-phenylethyl)urea. MS ESI calc'd. for C$_{22}$H$_{23}$N$_6$O [M+1]$^+$ 387. found 387. $^1$H NMR (500 MHz, DMSO-d$_6$) δ 13.33 (s, 1H), 9.06 (s, 1H), 8.54 (d, J=4.9 Hz, 1H), 7.94 (d, J=3.5 Hz, 1H), 7.51 (s, 1H), 7.48-7.34 (m, 4H), 7.23 (t, J=6.9 Hz, 1H), 4.86 (t, J=7.0 Hz, 1H), 3.29 (s, 3H), 2.46 (s, 3H), 1.40 (d, J=6.9 Hz, 3H).

The following examples were prepared according to Scheme 1 following similar procedures described for Example 1 using the appropriate pyrazolopyridine (Intermediate 1A), the appropriate boronic acids or esters, and commercial urea, which can be achieved by those of ordinary skill in the art of organic synthesis. The compound of example 2 was obtained as the trifluoroacetic acid salt.

(R)-1-(3-(2-fluoropyridin-4-yl)-4-(hydroxymethyl)-1H-pyrazolo[4,3-c]pyridin-6-yl)-3-(1-phenylethyl)urea

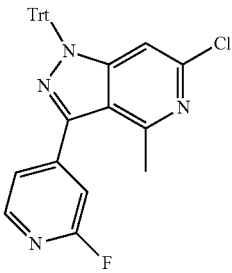

Step 1: 6-Chloro-3-(2-fluoropyridin-4-yl)-4-methyl-1-trityl-1H-pyrazolo[4,3-c]pyridine 6-Chloro-3-(2-fluoropyridin-4-yl)-4-methyl-1-trityl-1H-pyrazolo[4,3-c]pyridine was prepared using the same procedure as 6-chloro-4-methyl-3-(2-methylpyridin-4-yl)-1-trityl-1H-pyrazolo[4,3-c]pyridine (Example 1, Step 1). MS ESI calc'd. for C$_{31}$H$_{23}$ClFN$_4$ [M+1]$^+$ 505. found 505.

TABLE 3

| Example | Structure | IUPAC Name | Exact Mass [M + H]+ |
|---|---|---|---|
| 2 | 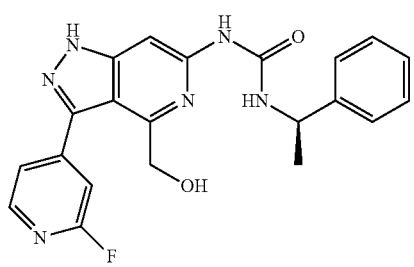 [SMILES: C[C@@H](NC(=O)Nc1cc2[nH]nc(-c3ccnc(F)c3)c2c(CO)n1)c1ccccc1] | 1-[3-(2-fluoropyridin-4-yl)-4-methyl-1H-pyrazolo[4,3-c]pyridin-6-yl]-3-[(1R)-1-phenylethyl]urea | Calc'd 391.0, found 391 |

The following examples were prepared according to scheme 2.

Example 3

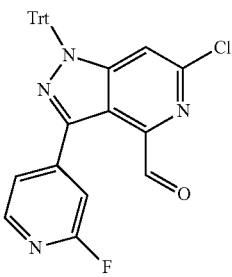

Step 2: 6-Chloro-3-(2-fluoropyridin-4-yl)-1-trityl-1H-pyrazolo[4,3-c]pyridine-4-carbaldehyde 6-Chloro-3-(2-fluoropyridin-4-yl)-4-methyl-1-trityl-1H-pyrazolo[4,3-c]pyridine (630 mg, 1.248 mmol) was dissolved in dioxane (11 mL) and selenium dioxide (415 mg, 3.74 mmol) was added. The reaction mixture was stirred overnight at reflux. The reaction was filtered through celite, rinsed with EtOAc, and concentrated in vacuo while loading onto silica gel. Purification by flash chromatography (5-40% EtOAc/Hexanes) gave 6-chloro-3-(2-fluoropyridin-4-yl)-1-trityl-1H-pyrazolo[4,3-c]pyridine-4-carbaldehyde. MS ESI calc'd. for $C_{31}H_{21}ClFN_4O$ [M+1]$^+$ 519. found 519.

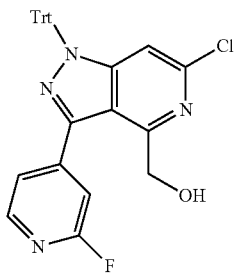

Step 3: (6-Chloro-3-(2-fluoropyridin-4-yl)-1-trityl-1H-pyrazolo[4,3-c]pyridin-4-yl)methanol (6-Chloro-3-(2-fluoropyridin-4-yl)-1-trityl-1H-pyrazolo[4,3-c]pyridin-4-yl)methanol was prepared using the same procedure as (6-chloro-3-iodo-1-trityl-1H-pyrazolo[4,3-c]pyridin-4-yl)methanol (Intermediate 8A, Step 2). MS ESI calc'd. for $C_{31}H_{23}ClFN_4O$ [M+1]$^+$ 521. found 521.

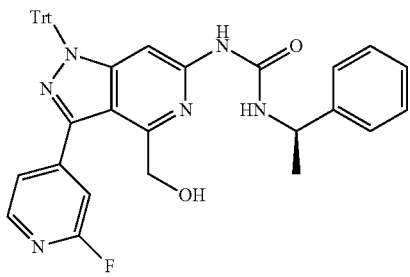

Step 4: (R)-1-(3-(2-Fluoropyridin-4-yl)-4-(hydroxymethyl)-1-trityl-1H-pyrazolo[4,3-c]pyridin-6-yl)-3-(1-phenylethyl)urea Chloro[2-(dicyclohexylphosphino)-3,6-dimethoxy-2'-4'-6'-tri-i-propyl-1,1'-biphenyl][2-(2-aminoethyl)phenyl]palladium(II) (38.4 mg, 0.048 mmol), (6-chloro-3-(2-fluoropyridin-4-yl)-1-trityl-1H-pyrazolo[4,3-c]pyridin-4-yl)methanol (250.2 mg, 0.480 mmol), cesium carbonate (469 mg, 1.441 mmol), 2-(dicyclohexylphosphino)-3,6-dimethoxy-2'-4'-6'-triisopropyl-1,1'-biphenyl (25.8 mg, 0.048 mmol), and (R)-1-(1-phenylethyl)urea (118 mg, 0.720 mmol) were dissolved in dioxane (2.5 mL). The vial was degassed with argon for 5 min and the reaction stirred at 100° C. for 4 hrs. Room temperature was attained, the reaction mixture was filtered through celite, eluting with MeOH, and the filtrate was concentrated in vacuo while loading onto silica gel. Purification by flash chromatography 7-100% EtOAc/Hexanes gave (R)-1-(3-(2-fluoropyridin-4-yl)-4-(hydroxymethyl)-1-trityl-1H-pyrazolo[4,3-c]pyridin-6-yl)-3-(1-phenylethyl) urea. MS ESI calc'd. for $C_{40}H_{34}FN_6O_2$ [M+1]$^+$ 649. found 649.

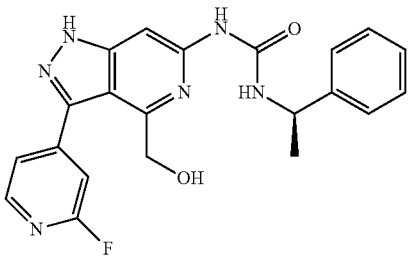 [SMILES: C[C@@H](NC(=O)Nc1cc2[nH]nc(-c3ccnc(F)c3)c2c(CO)n1)c1ccccc1]

Step 5: (R)-1-(3-(2-Fluoropyridin-4-yl)-4-(hydroxymethyl)-1H-pyrazolo[4,3-c]pyridin-6-yl)-3-(1-phenylethyl)urea (R)-1-(3-(2-Fluoropyridin-4-yl)-4-(hydroxymethyl)-1H-pyrazolo[4,3-c]pyridin-6-yl)-3-(1-phenylethyl)urea was prepared using the same procedure as (R)-1-(4-methyl-3-(2-methylpyridin-4-yl)-1H-pyrazolo[4,3-c]pyridin-6-yl)-3-(1-phenylethyl)urea (Example 1, Step 3). MS ESI calc'd. for $C_{21}H_{20}FN_6O_2$ [M+1]$^+$ 407. found 407. $^1$H NMR (500 MHz, DMSO-$d_6$) δ 13.56 (s, 1H), 9.16 (s, 1H), 8.33 (d, J=5.1 Hz, 1H), 7.72 (d, J=4.8 Hz, 1H), 7.59 (s, 1H), 7.32-7.20 (m, 4H), 7.11 (t, J=8.3 Hz, 1H), 5.28 (t, J=5.3 Hz, 1H), 4.88 (t, J=7.0 Hz, 1H), 4.63 (d, J=5.5 Hz, 2H), 1.40 (d, J=6.9 Hz, 3H).

The following examples were prepared according to scheme 3.

Example 4

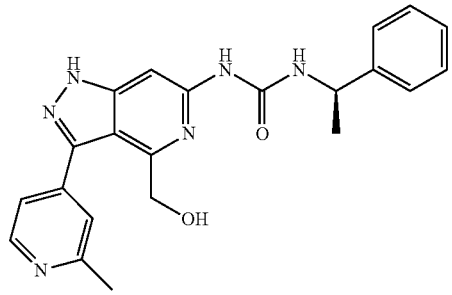 [SMILES: Cc1cc(-c2n[nH]c3cc(NC(=O)N[C@H](C)c4ccccc4)nc(CO)c23)ccn1]

(R)-1-(4-(hydroxymethyl)-3-(2-methylpyridin-4-yl)-1H-pyrazolo[4,3-c]pyridin-6-yl)-3-(1-phenylethyl) urea

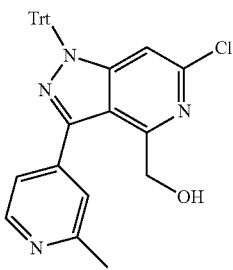

Step 1: (6-Chloro-3-(2-methylpyridin-4-yl)-1-trityl-1H-pyrazolo[4,3-c]pyridin-4-yl)methanol (6-Chloro-3-(2-methylpyridin-4-yl)-1-trityl-1H-pyrazolo[4,3-c]pyridin-4-yl)methanol was prepared using the same procedure as 6-chloro-4-methyl-3-(2-methylpyridin-4-yl)-1-trityl-1H-pyrazolo[4,3-c]pyridine (Example 1, Step 1). MS ESI calc'd. for $C_{32}H_{26}ClN_4O$ [M+1]$^+$ 517. found 517.

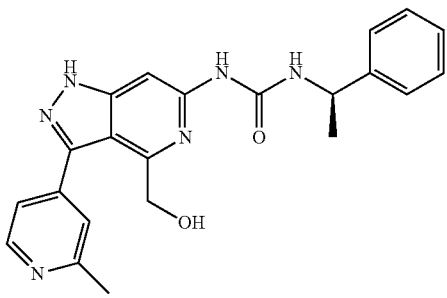 [SMILES: Cc1cc(-c2n[nH]c3cc(NC(=O)N[C@H](C)c4ccccc4)nc(CO)c23)ccn1]

Step 2: (R)-1-(4-(Hydroxymethyl)-3-(2-methylpyridin-4-yl)-1H-pyrazolo[4,3-c]pyridin-6-yl)-3-(1-phenylethyl)urea (6-Chloro-3-(2-methylpyridin-4-yl)-1-trityl-1H-pyrazolo[4,3-c]pyridin-4-yl)methanol (58.8 mg, 0.114 mmol), brettphos palladacycle (9.08 mg, 0.011 mmol), cesium carbonate (96 mg, 0.296 mmol), (R)-1-(1-phenylethyl)urea (28 mg, 0.171 mmol), and 2-(dicyclohexylphosphino)3,6-dimethoxy-2',4',6'-triisopropyl-1,1'-biphenyl (6.10 mg, 0.011 mmol) were dissolved in dioxane (1 mL). The vial was degassed with argon for 5 min and the reaction stirred at 100° C. for 6 hrs. Room temperature was attained, the reaction mixture was filtered through celite, eluting with MeOH, and the filtrate was concentrated in vacuo. The residue was dissolved in TFA (0.5 mL) and triethylsilane (0.027 mL, 0.171 mmol) was added. The reaction mixture was stirred at room temperature for 1 hr. The solvent was removed in vacuo, diluted with DMSO (1 mL), filtered, and purified by mass-triggered reverse-phase HPLC. The fractions containing pure product were freebased with a PL-HCO$_3$ cartridge and concentrated in vacuo to give (R)-1-(4-(hydroxymethyl)-3-(2-methylpyridin-4-yl)-1H-pyrazolo[4,3-c]pyridin-6-yl)-3-(1-phenylethyl)urea. MS ESI calc'd. for $C_{22}H_{23}N_6O_2$ [M+1]$^+$ 403. found 403. $^1$H NMR (500 MHz, DMSO-d$_6$) δ 13.42 (s, 1H), 9.16 (s, 1H), 8.53 (d, J=5.0 Hz, 1H), 7.53 (d, J=5.1 Hz, 1H), 7.43 (s, 1H), 7.38-7.28 (m, 4H), 7.21 (t, J=7.1 Hz, 1H), 5.19 (t, J=5.4 Hz, 1H), 4.93-4.83 (m, 1H), 4.61 (d, J=5.4 Hz, 2H), 2.53 (s, 3H), 1.40 (d, J=6.9 Hz, 3H).

The following examples were prepared according to Scheme 3 following similar procedures described for Example 4 using the appropriate pyrazolopyridine (Intermediate 8A), the appropriate boronic acids or esters, and commercial or synthesized ureas (Intermediates 60A, 61A, 62A, 63A, 64A), which can be achieved by those of ordinary skill in the art of organic synthesis. The compounds of examples 5, 6, 7, 8, 12, 14, and 15 were obtained as the trifluoroacetic acid salt.

TABLE 4

| Ex | Structure | IUPAC Name | Exact Mass [M + H]+ |
|---|---|---|---|
| 5 | 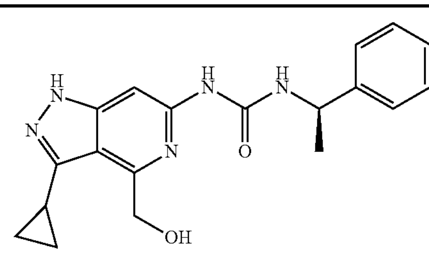 | (R)-1-(3-cyclopropyl-4-(hydroxymethyl)-1H-pyrazolo[4,3-c]pyridin-6-yl)-3-(1-phenylethyl)urea | Calc'd 352.0, found 352 |
| 6 | 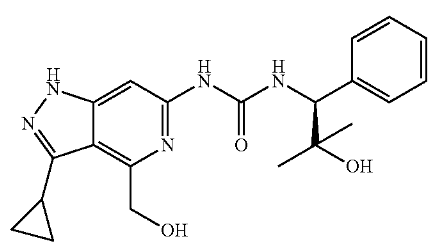 [SMILES: CC(C)(O)[C@@H](NC(=O)Nc1cc2[nH]nc(C3CC3)c2c(CO)n1)c1ccccc1] | 1-[3-cyclopropyl-4-(hydroxymethyl)-1H-pyrazolo[4,3-c]pyridin-6-yl]-3-[(1S)-2-hydroxy-2-methyl-1-phenylpropyl]urea | Calc'd 396.0, found 396 |
| 7 | 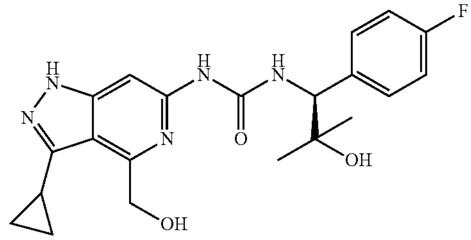 [SMILES: CC(C)(O)[C@@H](NC(=O)Nc1cc2[nH]nc(C3CC3)c2c(CO)n1)c1ccc(F)cc1] | 1-[3-cyclopropyl-4-(hydroxymethyl)-1H-pyrazolo[4,3-c]pyridin-6-yl]-3-[(1S)-1-(4-fluorophenyl)-2-hydroxy-2-methylpropyl]urea | Calc'd 414.0, found 414 |

TABLE 4-continued

| Ex | Structure | IUPAC Name | Exact Mass [M + H]+ |
|---|---|---|---|
| 8 | 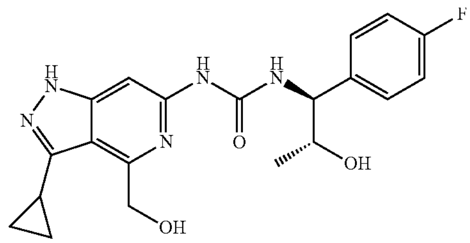 [SMILES: C[C@@H](O)[C@@H](NC(=O)Nc1cc2[nH]nc(C3CC3)c2c(CO)n1)c1ccc(F)cc1] | 1-[3-cyclopropyl-4-(hydroxymethyl)-1H-pyrazolo[4,3-c]pyridin-6-yl]-3-[(1S,2R)-1-(4-fluorophenyl)-2-hydroxypropyl]urea | Calc'd 400.0, found 400 |
| 9 | 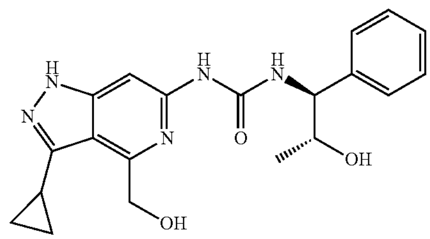 [SMILES: C[C@@H](O)[C@@H](NC(=O)Nc1cc2[nH]nc(C3CC3)c2c(CO)n1)c1ccccc1] | 1-[3-cyclopropyl-4-(hydroxymethyl)-1H-pyrazolo[4,3-c]pyridin-6-yl]-3-[(1S,2R)-2-hydroxy-1-phenylpropyl]urea | Calc'd 382.0, found 382 |
| 10 | 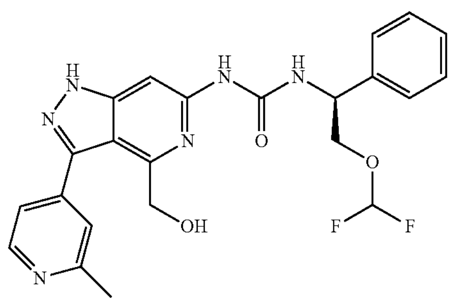 [SMILES: Cc1cc(-c2n[nH]c3cc(NC(=O)N[C@H](COC(F)F)c4ccccc4)nc(CO)c23)ccn1] | 1-[(1S)-2-(difluoromethoxy)-1-phenylethyl]-3-[4-(hydroxymethyl)-3-(2-methylpyridin-4-yl)-1H-pyrazolo[4,3-c]pyridin-6-yl]urea | Calc'd 469.0, found 469 |
| 11 | 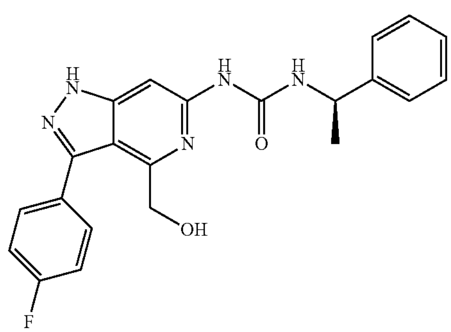 [SMILES: C[C@@H](NC(=O)Nc1cc2[nH]nc(-c3ccc(F)cc3)c2c(CO)n1)c1ccccc1] | 1-[3-(4-fluorophenyl)-4-(hydroxymethyl)-1H-pyrazolo[4,3-c]pyridin-6-yl]-3-[(1R)-1-phenylethyl]urea | Calc'd 406.0, found 406 |
| 12 | 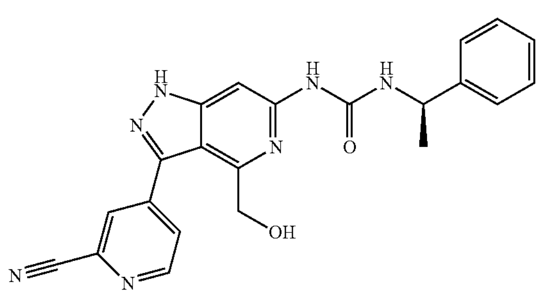 [SMILES: C[C@@H](NC(=O)Nc1cc2[nH]nc(-c3ccnc(C#N)c3)c2c(CO)n1)c1ccccc1] | 1-[3-(2-cyanopyridin-4-yl)-4-(hydroxymethyl)-1H-pyrazolo[4,3-c]pyridin-6-yl]-3-[(1R)-1-phenylethyl]urea | Calc'd 414.0, found 414 |

TABLE 4-continued

| Ex | Structure | IUPAC Name | Exact Mass [M + H]+ |
|---|---|---|---|
| 13 | 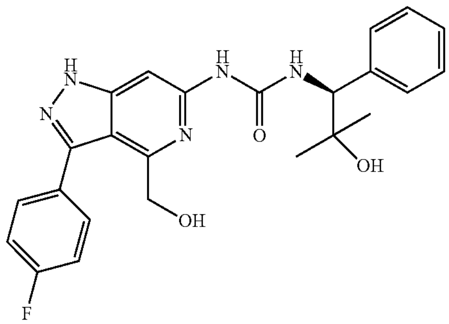 [SMILES: CC(C)(O)[C@@H](NC(=O)Nc1cc2[nH]nc(-c3ccc(F)cc3)c2c(CO)n1)c1ccccc1] | 1-[3-(4-fluorophenyl)-4-(hydroxymethyl)-1H-pyrazolo[4,3-c]pyridin-6-yl]-3-[(1S)-2-hydroxy-2-methyl-1-phenylpropyl]urea | Calc'd 450.0, found 450 |
| 14 | 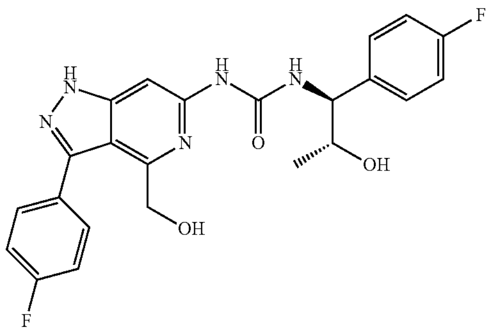 [SMILES: C[C@@H](O)[C@@H](NC(=O)Nc1cc2[nH]nc(-c3ccc(F)cc3)c2c(CO)n1)c1ccc(F)cc1] | 1-[3-(4-fluorophenyl)-4-(hydroxymethyl)-1H-pyrazolo[4,3-c]pyridin-6-yl]-3-[(1S,2R)-1-(4-fluorophenyl)-2-hydroxypropyl]urea | Calc'd 454.0, found 454 |
| 15 | 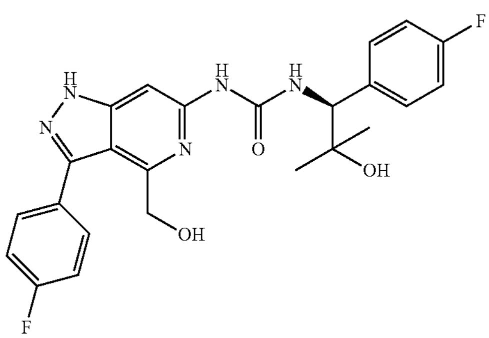 [SMILES: CC(C)(O)[C@@H](NC(=O)Nc1cc2[nH]nc(-c3ccc(F)cc3)c2c(CO)n1)c1ccc(F)cc1] | 1-[(1S)-1-(4-fluorophenyl)-2-hydroxy-2-methylpropyl]-3-[3-(4-fluorophenyl)-4-(hydroxymethyl)-1H-pyrazolo[4,3-c]pyridin-6-yl]urea | Calc'd 468.0, found 468 |
| 16 | 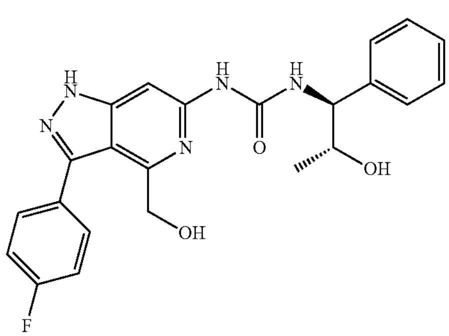 [SMILES: C[C@@H](O)[C@@H](NC(=O)Nc1cc2[nH]nc(-c3ccc(F)cc3)c2c(CO)n1)c1ccccc1] | 1-[3-(4-fluorophenyl)-4-(hydroxymethyl)-1H-pyrazolo[4,3-c]pyridin-6-yl]-3-[(1S,2R)-2-hydroxy-1-phenylpropyl]urea | Calc'd 436.0, found 436 |

TABLE 4-continued

| Ex | Structure | IUPAC Name | Exact Mass [M + H]+ |
|----|-----------|------------|---------------------|
| 17 | 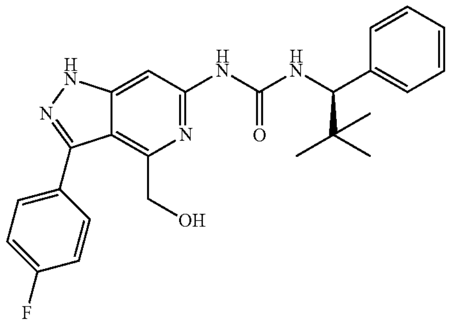 [SMILES: CC(C)(C)[C@@H](NC(=O)Nc1cc2[nH]nc(-c3ccc(F)cc3)c2c(CO)n1)c1ccccc1] | 1-[(1R)-2,2-dimethyl-1-phenylpropyl]-3-[3-(4-fluorophenyl)-4-(hydroxymethyl)-1H-pyrazolo[4,3-c]pyridin-6-yl]urea | Calc'd 448.0, found 448 |
| 18 | 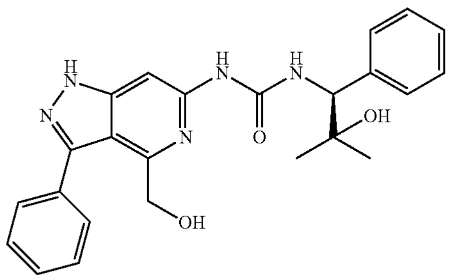 [SMILES: CC(C)(O)[C@@H](NC(=O)Nc1cc2[nH]nc(-c3ccccc3)c2c(CO)n1)c1ccccc1] | 1-[(1S)-2-hydroxy-2-methyl-1-phenylpropyl]-3-[4-(hydroxymethyl)-3-phenyl-1H-pyrazolo[4,3-c]pyridin-6-yl]urea | Calc'd 432.0, found 432 |
| 19 | 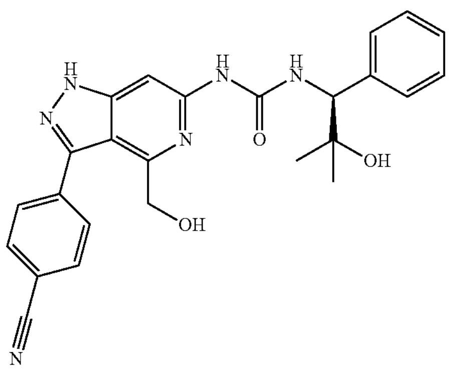 [SMILES: CC(C)(O)[C@@H](NC(=O)Nc1cc2[nH]nc(-c3ccc(C#N)cc3)c2c(CO)n1)c1ccccc1] | 1-[3-(4-cyanophenyl)-4-(hydroxymethyl)-1H-pyrazolo[4,3-c]pyridin-6-yl]-3-[(1S)-2-hydroxy-2-methyl-1-phenylpropyl]urea | Calc'd 457.0, found 457 |

The following example was prepared according to scheme 4.

Example 20

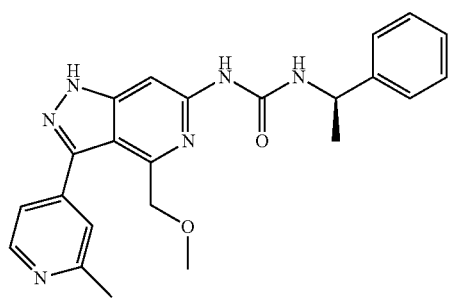 [SMILES: COCc1nc(NC(=O)N[C@H](C)c2ccccc2)cc2[nH]nc(-c3ccnc(C)c3)c12]

(R)-1-(4-(Methoxymethyl)-3-(2-methylpyridin-4-yl)-1H-pyrazolo[4,3-c]pyridin-6-yl)-3-(1-phenylethyl)urea

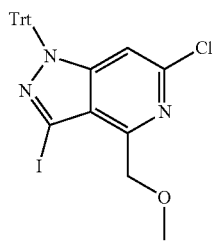

Step 1: 6-Chloro-3-iodo-4-(methoxymethyl)-1-trityl-1H-pyrazolo[4,3-c]pyridine (6-Chloro-3-iodo-1-trityl-1H-pyrazolo[4,3-c]pyridin-4-yl)methanol (Intermediate 8A, 200 mg, 0.362 mmol) was dissolved in DMF (2 mL) and cooled to 0° C. Sodium hydride (17.40 mg, 0.435 mmol) was added and the reaction stirred at 0° C. for 30 min. Methyl iodide (0.027 mL, 0.435 mmol) was then added, the reaction mixture was warmed to room temperature, and stirred for 1 hrs. Sodium hydride (17.40 mg, 0.435 mmol) was added and the reaction mixture was stirred for 15 min followed by addition of methyl iodide (0.027 mL, 0.435 mmol). The reaction mixture stirred at room temperature for 1 hr. The reaction was diluted with EtOAc and washed with brine. The combined organic layers were dried over sodium sulfate, filtered, and concentrated in vacuo while loading onto silica gel. Purification of the residue by flash chromatography (5-40% EtOAc/Hexanes) gave 6-chloro-3-iodo-4-(methoxymethyl)-1-trityl-1H-pyrazolo[4,3-c]pyridine. MS ESI calc'd. for $C_{27}H_{22}ClIN_3O$ $[M+1]^+$ 566. found 566.

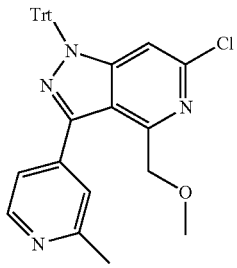

Step 2: 6-Chloro-4-(methoxymethyl)-3-(2-methyl-pyridin-4-yl)-1-trityl-1H-pyrazolo[4,3-c]pyridine 6-Chloro-4-(methoxymethyl)-3-(2-methylpyridin-4-yl)-1-trityl-1H-pyrazolo[4,3-c]pyridine was prepared using the same procedure as 6-chloro-4-methyl-3-(2-methylpyridin-4-yl)-1-trityl-1H-pyrazolo[4,3-c]pyridine (Example 1, Step 1). MS ESI calc'd. for $C_{33}H_{28}ClN_4O$ $[M+1]^+$ 531. found 531.

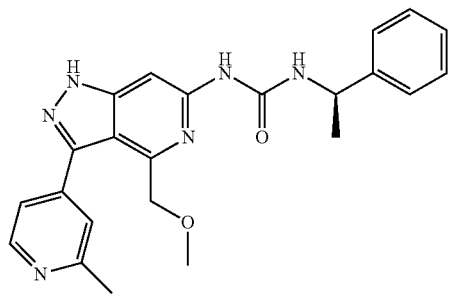 [SMILES: COCc1nc(NC(=O)N[C@H](C)c2ccccc2)cc2[nH]nc(-c3ccnc(C)c3)c12]

Step 3: (R)-1-(4-(Methoxymethyl)-3-(2-methylpyridin-4-yl)-1H-pyrazolo[4,3-c]pyridin-6-yl)-3-(1-phenylethyl)urea 6-Chloro-4-(methoxymethyl)-3-(2-methylpyridin-4-yl)-1-trityl-1H-pyrazolo[4,3-c]pyridine (19.1 mg, 0.036 mmol), brettphos palladacycle (2.87 mg, 3.60 µmol), cesium carbonate (30.5 mg, 0.094 mmol), (R)-1-(1-phenylethyl)urea (8.86 mg, 0.054 mmol), and 2-(dicyclohexylphosphino)3,6-dimethoxy-2',4',6'-triisopropyl-1,1'-biphenyl (1.931 mg, 3.60 µmol) were dissolved in Dioxane (1 mL). The vial was degassed with argon for 5 min and the reaction stirred at 100° C. for 6 hrs. Room temperature was attained, the reaction mixture was filtered through celite, eluting with MeOH, and the filtrate was concentrated in vacuo. The residue was dissolved in TFA (0.75 mL) and triethylsilane (8.62 µl, 0.054 mmol) was added. The reaction mixture was stirred at room temperature for 1 hr. The solvent was removed in vacuo, diluted with DMSO (1 mL), filtered, and purified by mass-triggered reverse-phase HPLC. The fractions containing pure product were concentrated in vacuo to afford (R)-1-(4-(methoxymethyl)-3-(2-methylpyridin-4-yl)-1H-pyrazolo[4,3-c]pyridin-6-yl)-3-(1-phenylethyl)urea as the trifluoroacetic acid salt. MS ESI calc'd. for $C_{23}H_{25}N_6O_2$ $[M+1]^+$417. found 417. $^1$H NMR (500 MHz, DMSO-$d_6$) δ 13.84 (s, 1H), 9.24 (s, 1H), 8.80 (s, 1H), 8.04 (d, J=4.9 Hz, 1H), 7.67 (s, 1H), 7.37-7.35 (m, 4H), 7.24 (s, 1H), 4.88 (t, J=7.0 Hz, 1H), 4.59 (s, 2H), 3.04 (s, 3H), 2.73 (s, 3H), 1.41 (d, J=7.1 Hz, 3H).

The following example was prepared according to scheme 5.

Example 21

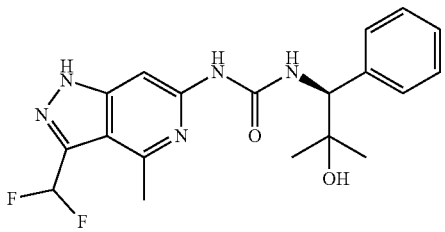 [SMILES: Cc1nc(NC(=O)N[C@@H](c2ccccc2)C(C)(C)O)cc2[nH]nc(C(F)F)c12]

(S)-1-(3-(difluoromethyl)-4-methyl-1H-pyrazolo[4,3-c]pyridin-6-yl)-3-(2-hydroxy-2-methyl-1-phenyl-propyl)urea

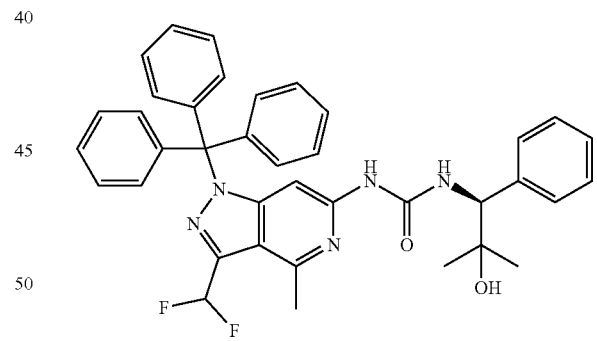

Step 1: (S)-1-(3-(difluoromethyl)-4-methyl-1-trityl-1H-pyrazolo[4,3-c]pyridin-6-yl)-3-(2-hydroxy-2-methyl-1-phenylpropyl)urea 6-chloro-3-(difluoromethyl)-4-methyl-1-trityl-1H-pyrazolo[4,3-c]pyridine (Intermediate 16A, 70 mg, 0.152 mmol), Brett Phos Pre-Catalyst (12.16 mg, 0.015 mmol), (S)-1-(2-hydroxy-2-methyl-1-phenylpropyl)urea (Intermediate 60A, 47.5 mg, 0.228 mmol), and cesium carbonate (149 mg, 0.457 mmol) were combined in a 2.0 mL microwave vial. The vial was evacuated and backfilled (3×) with $N_2$ gas before adding 1,4-dioxane (1.50 mL). The reaction was allowed to stir at 100° C. overnight. Room temperature was attained and the mixture was filtered through a celite plug eluting with EtOAc. The crude mixture was concentrated in vacuo. The desired product, (S)-1-(3-(difluoromethyl)-4-methyl-1-trityl-1H-pyrazolo[4,3-c]pyridin-6-yl)-3-(2-hydroxy-2-methyl-1-phenylpropyl)urea, was obtained and was carried forward without purification. MS ESI calc'd. for $C_{38}H_{36}F_2N_5O_2$ [M+1]$^+$ 632. found 632.

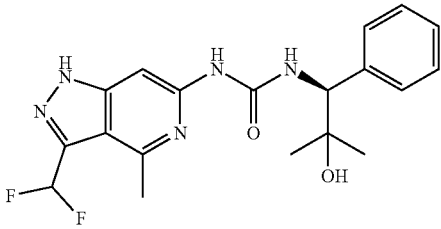 [SMILES: Cc1nc(NC(=O)N[C@@H](c2ccccc2)C(C)(C)O)cc2[nH]nc(C(F)F)c12]

Step 2: (S)-1-(3-(difluoromethyl)-4-methyl-1H-pyrazolo[4,3-c]pyridin-6-yl)-3-(2-hydroxy-2-methyl-1-phenylpropyl)urea (S)-1-(3-(difluoromethyl)-4-methyl-1-trityl-1H-pyrazolo[4,3-c]pyridin-6-yl)-3-(2-hydroxy-2-methyl-1-phenylpropyl)urea was taken up in TFA (1.5 ml) and triethylsilane (36.5 µl, 0.228 mmol) was added dropwise. The reaction mixture was allowed to stir at room temperature for 1 hr. The mixture was concentrated in vacuo and resuspended in MeOH/DMSO. The sample was purified via mass-triggered reverse-phase preparative HPLC followed by MPLC 25-100% DCM/EtOAc to give (S)-1-(3-(difluoromethyl)-4-methyl-1H-pyrazolo[4,3-c]pyridin-6-yl)-3-(2-hydroxy-2-methyl-1-phenylpropyl)urea as the trifluoroacetic acid salt. MS ESI calc'd. for $C_{19}H_{22}F_2N_5O_2$[M+1]$^+$ 390. found 390. $^1$H NMR (500 MHz, DMSO-d$_6$) δ 13.49 (s, 1H), 9.29 (s, 1H), 8.40 (br s, 1H), 7.42 (s, 1H), 7.40-7.17 (m, 6H), 4.58 (d, J=9.0 Hz, 1H), 2.73 (s, 3H), 1.17 (s, 3H), 0.99 (s, 3H).

The following example was prepared according to scheme 6.

Example 22

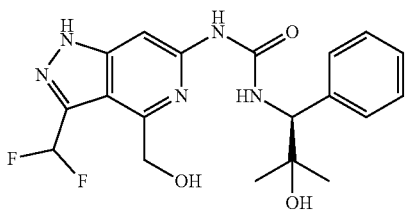 [SMILES: CC(C)(O)[C@@H](NC(=O)Nc1cc2[nH]nc(C(F)F)c2c(CO)n1)c1ccccc1]

(S)-1-(3-(difluoromethyl)-4-(hydroxymethyl)-1H-pyrazolo[4,3-c]pyridin-6-yl)-3-(2-hydroxy-2-methyl-1-phenylpropyl)urea

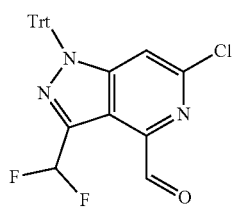

Step 1: 6-chloro-3-(difluoromethyl)-1-trityl-1H-pyrazolo[4,3-c]pyridine-4-carbaldehyde Intermediate 16A (423 mg, 0.920 mmol) was dissolved in dioxane (10 mL) and selenium dioxide (306 mg, 2.76 mmol) was added. The reaction mixture was stirred overnight at reflux. The reaction was filtered through celite, washed with EtOAc, and concentrated in vacuo while loading onto silica gel. Purification by flash chromatography (10-50% EtOAc/Hexanes) gave 6-chloro-3-(difluoromethyl)-1-trityl-1H-pyrazolo[4,3-c]pyridine-4-carbaldehyde. The material was carried crude into subsequent reaction step where M+ was determined.

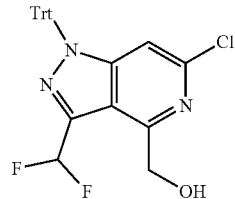

Step 2: (6-chloro-3-(difluoromethyl)-1-trityl-1H-pyrazolo[4,3-c]pyridin-4-yl)methanol (6-chloro-3-(difluoromethyl)-1-trityl-1H-pyrazolo[4,3-c]pyridin-4-yl)methanol was prepared using the same procedure as (6-chloro-3-iodo-1-trityl-1H-pyrazolo[4,3-c]pyridin-4-yl)methanol (Intermediate 8A, Step 2) to give (6-chloro-3-(difluoromethyl)-1-trityl-1H-pyrazolo[4,3-c]pyridin-4-yl)methanol. MS ESI calc'd. for $C_{27}H_{21}ClF_2N_3O$ [M+1]$^+$ 476. found 476.

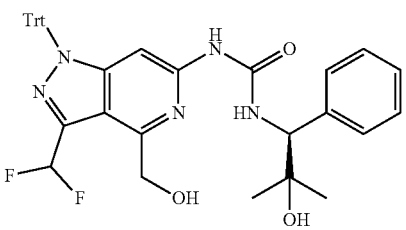

Step 3: (S)-1-(3-(difluoromethyl)-4-(hydroxymethyl)-1-trityl-1H-pyrazolo[4,3-c]pyridin-6-yl)-3-(2-hydroxy-2-methyl-1-phenylpropyl)urea (6-chloro-3-(difluoromethyl)-1-trityl-1H-pyrazolo[4,3-c]pyridin-4-yl)methanol (90 mg, 0.189 mmol), BrettPhos Precatalyst (15.11 mg, 0.019 mmol), cesium carbonate (185 mg, 0.567 mmol), and (S)-1-(2-hydroxy-2-methyl-1-phenylpropyl)urea (Intermediate 60A, 60 mg, 0.288 mmol) were combined in a 5 mL microwave vial. The vial was evacuated and back-filled three tiems with nitrogen gas before adding dioxane (2.5 ml). The reaction mixture was stirred at 90° C. for 2 hrs. Room temperature was attained. The reaction mixture was filtered through a celite frit, eluting with EtOAc/DCM. The mixture was then concentrated in vacuo and loaded directly onto silica gel for purification by MPLC 0-100% EtOAc/DCM to give (S)-1-(3-(difluoromethyl)-4-(hydroxymethyl)- 1-trityl-1H-pyrazolo[4,3-c]pyridin-6-yl)-

3-(2-hydroxy-2-methyl-1-phenylpropyl)urea. MS ESI calc'd. for $C_{38}H_{36}F_2N_5O_3$ [M+1]$^+$ 648. found 648.

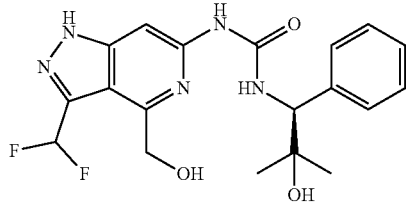 [SMILES: CC(C)(O)[C@@H](NC(=O)Nc1cc2[nH]nc(C(F)F)c2c(CO)n1)c1ccccc1]

Step 4: (S)-1-(3-(difluoromethyl)-4-(hydroxymethyl)-1H-pyrazolo[4,3-c]pyridin-6-yl)-3-(2-hydroxy-2-methyl-1-phenylpropyl)urea (S)-1-(3-(difluoromethyl)-4-(hydroxymethyl)-1-trityl-1H-pyrazolo[4,3-c]pyridin-6-yl)-3-(2-hydroxy-2-methyl-1-phenylpropyl)urea (90 mg, 0.139 mmol) was taken up in TFA (2.0 mL) and triethylsilane (0.033 ml, 0.208 mmol) was added dropwise while the reaction mixture was stirring at room temperature. The reaction was allowed to stir for 30 mins until complete by LCMS. The mixture was concentrated in vacuo then suspended in DMSO/MeOH (3.0 mL) for purification by reverse phase mass-triggered preparative HPLC. Fractions containing pure product were evaporated to dryness, resulting in (S)-1-(3-(difluoromethyl)-4-(hydroxymethyl)-1H-pyrazolo[4,3-c]pyridin-6-yl)-3-(2-hydroxy-2-methyl-1-phenylpropyl)urea, as the trifluoroacetic acid salt. MS ESI calc'd. for $C_{19}H_{22}F_2N_5O_3$ [M+1]$^+$ 406. found 406. $^1$H NMR (500 MHz, DMSO-$d_6$) δ 13.70 (s, 1H), 9.60 (s, 1H), 8.40 (br s, 1H), 7.46 (s, 1H), 7.38 (t, J=55, 1H), 7.35-7.31 (m, 2H), 7.29-7.25 (m, 2H), 7.22-7.18 (m, 1H), 4.58 (s, 2H), 4.60 (d, J=9.5 Hz, 1H), 1.17 (s, 3H), 0.99 (s, 3H).

The following examples were prepared according to Scheme 6 following similar procedures described for Example 22 using the appropriate pyrazolopyridine (Intermediate 16A) and commercial or synthesized ureas (Intermediate 61A), which can be achieved by those of ordinary skill in the art of organic synthesis. The compounds of examples 23 and 24 were obtained as the trifluoroacetic acid salt.

The following example was prepared according to scheme 7.

Example 25

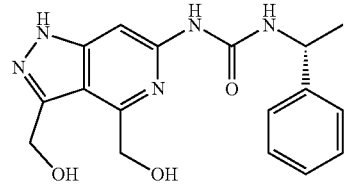

(R)-1-(3,4-bis(hydroxymethyl)-1H-pyrazolo[4,3-c]pyridin-6-yl)-3-(1-phenylethyl)urea

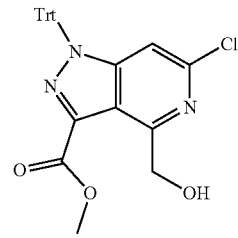

Step 1: Methyl 6-chloro-4-(hydroxymethyl)-1-trityl-1H-pyrazolo[4,3-c]pyridine-3-carboxylate A suspension of sodium acetate (0.223 g, 2.72 mmol), PdCl2(dppf)CH$_2$Cl$_2$ (0.148 g, 0.181 mmol) and Intermediate 8A (1.0 g, 1.812 mmol) in MeOH (20 ml) was stirred under CO (80 psi) at 65° C. for 3 days. The reaction mixture was diluted with DCM and dry loaded onto silica gel. Purification by MPLC 0-30% EtOAc/Hexanes to provide methyl 6-chloro-4-(hydroxymethyl)-1-trityl-1H-pyrazolo[4,3-c]pyridine-3-carboxylate. MS ESI calc'd. for $C_{28}H_{23}ClN_3O_3$ [M+1]$^+$ 484. found 484.

TABLE 5

| Ex | Structure | IUPAC Name | Exact Mass [M + H]+ |
|---|---|---|---|
| 23 | 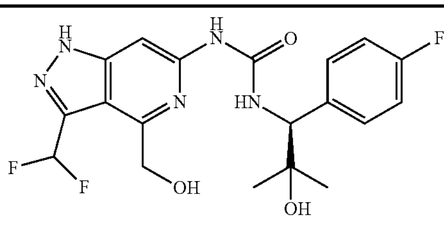 | 1-[3-(difluoromethyl)-4-(hydroxymethyl)-1H-pyrazolo[4,3-c]pyridin-6-yl]-3-[(1S)-1-(4-fluorophenyl)-2-hydroxy-2-methylpropyl]urea | Calc'd 424.0, found 424 |
| 24 | 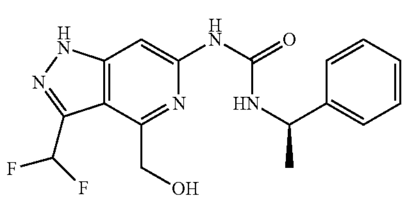 [SMILES: C[C@@H](NC(=O)Nc1cc2[nH]nc(C(F)F)c2c(CO)n1)c1ccccc1] | 1-[3-(difluoromethyl)-4-(hydroxymethyl)-1H-pyrazolo[4,3-c]pyridin-6-yl]-3-[(1R)-1-phenylethyl]urea | Calc'd 362.0, found 362 |

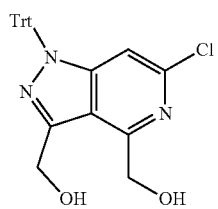

Step 2: (6-chloro-1-trityl-1H-pyrazolo[4,3-c]pyridine-3,4-diyl)dimethanol

At −78° C., to a solution of methyl 6-chloro-4-(hydroxymethyl)-1-trityl-1H-pyrazolo[4,3-c]pyridine-3-carboxylate (250 mg, 0.517 mmol) in DCM (3.0 ml) under an inert atmosphere of nitrogen gas, 1.0 M DIBAL-H (1.136 ml, 1.136 mmol) in THF was added dropwise. The reaction mixture was allowed to stir at −78° C. for 2 hrs. EtOAc and Rochelle salt solution were added into the reaction mixture and the water layer was extracted into EtOAc for two additional times. The organic layers were combined and washed by water and brine, dried over $Na_2SO_4$, then concentrated in vacuo. The residue was purified on silica gel 0-50% EtOAc/Hexanes to provide (6-chloro-1-trityl-1H-pyrazolo[4,3-c]pyridine-3,4-diyl)dimethanol. MS ESI calc'd. for $C_{27}H_{23}ClN_3O_2$ $[M+1]^+$ 456. found 456.

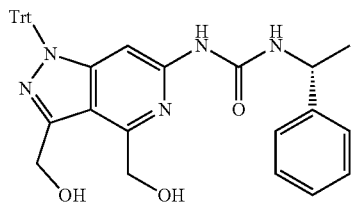

Step 3: (R)-1-(3,4-bis(hydroxymethyl)-1-trityl-1H-pyrazolo[4,3-c]pyridin-6-yl)-3-(1-phenylethyl)urea (6-chloro-1-trityl-1H-pyrazolo[4,3-c]pyridine-3,4-diyl)dimethanol (130 mg, 0.285 mmol), (R)-1-(1-phenylethyl)urea (94 mg, 0.570 mmol), cesium carbonate (279 mg, 0.855 mmol), Brettphos palladacycle (22.78 mg, 0.029 mmol) and BrettPhos (15.30 mg, 0.029 mmol) were taken up in Dioxane (6.0 ml) in a 20 mL microwave vial. The vial was evacuated and back-filled with $N_2$ gas three times before heating to 90° C. for 24 hrs. The reaction mixture was filtered though celite and concentrated in vacuo. The residue (R)-1-(3,4-bis(hydroxymethyl)-1-trityl-1H-pyrazolo[4,3-c]pyridin-6-yl)-3-(1-phenylethyl)urea was used in next step without purification. MS ESI calc'd. for $C_{36}H_{34}N_5O_3$ $[M+1]^+$ 584. found 584.

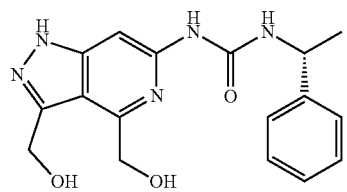 [SMILES: C[C@@H](NC(=O)Nc1cc2[nH]nc(CO)c2c(CO)n1)c1ccccc1]

Step 4: (R)-1-(3,4-bis(hydroxymethyl)-1H-pyrazolo[4,3-c]pyridin-6-yl)-3-(1-phenylethyl)urea To the solution of (R)-1-(3,4-bis(hydroxymethyl)-1-trityl-1H-pyrazolo[4,3-c]pyridin-6-yl)-3-(1-phenylethyl)urea (145 mg, 0.248 mmol) and TFA (0.957 ml, 12.42 mmol) in DCM (1.0 ml) was added triethylsilane (0.060 ml, 0.373 mmol). The resulting mixture was allowed to stir at ambient temperature for 18 hrs. Solvent was evaporated in vacuo and the oil was diluted with DMSO, filtered, and purified by mass-triggered reverse-phase HPLC. The fractions containing product were evaporated and the solid was dissolved in MeOH and filtered through a PL-$HCO_3$ cartridge to liberate the freebase as (R)-1-(3,4-bis(hydroxymethyl)-1H-pyrazolo[4,3-c]pyridin-6-yl)-3-(1-phenylethyl)urea. MS ESI calc'd. for $C_{17}H_{20}N_5O_3[M+1]^+$ 342. found 342. $^1$H NMR (500 MHz, DMSO-$d_6$) δ 13.31 (br s, 1H), 8.32 (br s, 1H), 7.50-7.09 (m, 6H), 5.10 (s, 2H), 4.95-4.83 (m, 1H), 4.73 (s, 2H), 1.39 (d, J=23.6, 3H).

The following example was prepared according to scheme 8.

Example 26

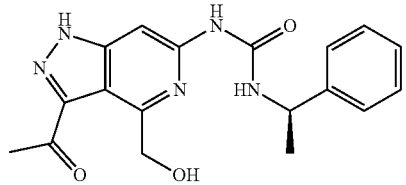 [SMILES: CC(=O)c1n[nH]c2cc(NC(=O)N[C@H](C)c3ccccc3)nc(CO)c12]

(R)-1-(3-acetyl-4-(hydroxymethyl)-1H-pyrazolo[4,3-c]pyridin-6-yl)-3-(1-phenylethyl)urea

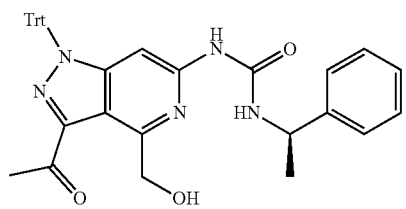

Step 1: (R)-1-(3-acetyl-4-(hydroxymethyl)-1-trityl-1H-pyrazolo[4,3-c]pyridin-6-yl)-3-(1-phenylethyl)urea 1-(6-chloro-4-(hydroxymethyl)-1-trityl-1H-pyrazolo[4,3-c]pyridin-3-yl)ethanone (Intermediate 27A, 114 mg, 0.244 mmol), (R)-1-(1-phenylethyl)urea (80 mg, 0.487 mmol), cesium carbonate (238 mg, 0.731 mmol), Brettphos palladacycle (19.45 mg, 0.024 mmol) and BrettPhos (13.08 mg, 0.024 mmol) were taken up in Dioxane (5.0 ml) in a 5 mL microwave vial. The vial was evacuated and back-filled with $N_2$ three times before heating to 90° C. for 24 hrs. The reaction mixture was filtered though celite and concentrated in vacuo. The residue (R)-1-(3-acetyl-4-(hydroxymethyl)-1-trityl-1H-pyrazolo[4,3-c]pyridin-6-yl)-3-(1-phenylethyl)urea was used in next step without purification. MS ESI calc'd. for $C_{37}H_{34}N_5O_3$ $[M+1]^+$ 496. found 496.

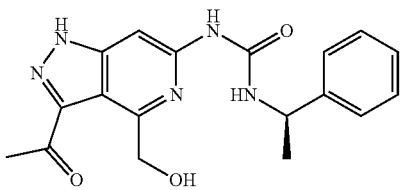 [SMILES: CC(=O)c1n[nH]c2cc(NC(=O)N[C@H](C)c3ccccc3)nc(CO)c12]

Step 2: (R)-1-(3-acetyl-4-(hydroxymethyl)-1H-pyrazolo[4,3-c]pyridin-6-yl)-3-(1-phenylethyl)urea To the solution of (R)-1-(3-acetyl-4-(hydroxymethyl)-1-trityl-1H-pyrazolo[4,3-c]pyridin-6-yl)-3-(1-phenylethyl) urea (145 mg, 0.243 mmol) and TFA (0.938 ml, 12.17 mmol) in dichloromethane (1.0 ml) was added triethylsilane (0.058 ml, 0.365 mmol). The resulting mixture was allowed to stir at room temperature for 1 hr. The solvent was evaporated in vacuo and the oil was diluted with DMSO, filtered, and purified by mass-triggered reverse-phase HPLC to give (R)-1-(3-acetyl-4-(hydroxymethyl)-1H-pyrazolo[4,3-c]pyridin-6-yl)-3-(1-phenylethyl)urea, which was obtained as the trifluoroacetic acid salt. MS ESI calc'd. for $C_{18}H_{20}N_5O_3$ [M+1]$^+$ 354. found 354. $^1$H NMR (500 MHz, dmso) δ 14.10 (br s, 1H), 10.29-9.73 (m, 1H), 8.46 (br s, 1H), 7.47-7.09 (m, 6H), 5.12 (s, 2H), 4.89 (m, J=7.1, 1H), 2.63 (s, 3H), 1.42 (d, J=6.9, 3H).

The following example was prepared according to scheme 9.

Example 27

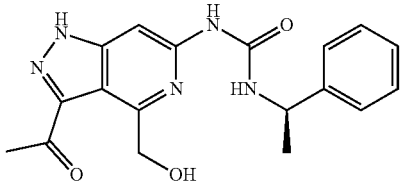 [SMILES: CC(=O)c1n[nH]c2cc(NC(=O)N[C@H](C)c3ccccc3)nc(CO)c12]

1-(3-(1-hydroxyethyl)-4-(hydroxymethyl)-1H-pyrazolo[4,3-c]pyridin-6-yl)-3-((R)-1-phenylethyl)urea

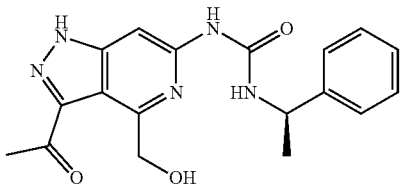 [SMILES: CC(=O)c1n[nH]c2cc(NC(=O)N[C@H](C)c3ccccc3)nc(CO)c12]

Step 1: 1-(3-(1-hydroxyethyl)-4-(hydroxymethyl)-1H-pyrazolo[4,3-c]pyridin-6-yl)-3-((R)-1-phenylethyl)urea To the solution of (R)-1-(3-acetyl-4-(hydroxymethyl)-1H-pyrazolo[4,3-c]pyridin-6-yl)-3-(1-phenylethyl)urea (Example 26) (7.8 mg, 0.022 mmol) in DCM (1.0 ml) and MeOH (1.5 ml) was added sodium borohydride (0.919 mg, 0.024 mmol). The resulting solution was allowed to stir at ambient temperature for 1 hr. DCM (5 ml) and water (3 ml) were added into the solution and the organic layer was collected. The organics were washed with brine, dried over $Na_2SO_4$, and concentrated in vacuo. The residue was purified on silica gel 0-100% EtOAc/DCM to provide 1-(3-(1-hydroxyethyl)-4-(hydroxymethyl)-1H-pyrazolo[4,3-c]pyridin-6-yl)-3-((R)-1-phenylethyl)urea. MS ESI calc'd. for $C_{18}H_{22}N_5O_3$[M+1]$^+$ 356. found 356. $^1$H NMR (500 MHz, DMSO-d$_6$) δ 9.08 (s, 1H), 7.66 (t, J=17.6, 1H), 7.28 (m, 5H), 5.14 (m, 1H), 4.87 (dd, J=19.7, 32.3, 2H), 4.20-3.94 (m, 1H), 1.47-1.14 (m, 3H), 0.93-0.76 (m, 3H).

The following example was prepared according to scheme 10.

Example 28

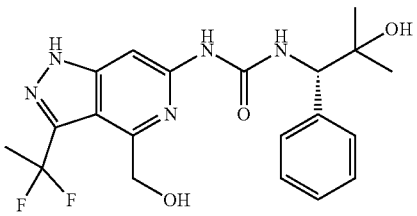 [SMILES: CC(F)(F)c1n[nH]c2cc(NC(=O)N[C@@H](c3ccccc3)C(C)(C)O)nc(CO)c12]

(S)-1-(3-(1,1-difluoroethyl)-4-(hydroxymethyl)-1H-pyrazolo[4,3-c]pyridin-6-yl)-3-(2-hydroxy-2-methyl-1-phenylpropyl)urea

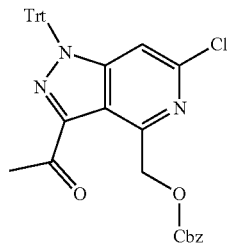

Step 1: (3-acetyl-6-chloro-1-trityl-1H-pyrazolo[4,3-c]pyridin-4-yl)methyl benzyl carbonate To the solution of Intermediate 27A (700 mg, 1.496 mmol), DMAP (18.28 mg, 0.150 mmol) and DIPEA (0.392 ml, 2.244 mmol) in THF (10 ml) was added benzyl chloroformate (0.235 ml, 1.645 mmol) dropwise. The resulting solution was allowed to stir at ambient temperature for 24 hrs. The reaction mixture was diluted with DCM and washed with saturated NaHCO$_3$ and brine. The organic phase was dried over Na$_2$SO$_4$ and concentrated in vacuo. Purification on silica gel 0-50% EtOAc/Hexanes provided (3-acetyl-6-chloro-1-trityl-1H-pyrazolo[4,3-c]pyridin-4-yl)methyl benzyl carbonate. MS ESI calc'd. for $C_{36}H_{29}ClN_3O_4$[M+1]$^+$ 602. found 602.

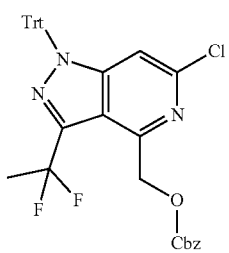

Step 2: benzyl ((6-chloro-3-(1,1-difluoroethyl)-1-trityl-1H-pyrazolo[4,3-c]pyridin-4-yl)methyl) carbonate A solution of (3-acetyl-6-chloro-1-trityl-1H-pyrazolo[4,3-c]pyridin-4-yl)methyl benzyl carbonate (315 mg, 0.523 mmol) and BAST (0.965 ml, 5.23 mmol) in DCE (5.0 ml) was allowed to stir at 65° C. for 20 hours. The reaction was cooled to ambient temperature and then diluted with DCM. Water and saturated NaHCO₃ were added. The products were extraced two times into DCM. The organic extracts were collected, washed with brine, dried over Na₂SO₄, and concentrated in vacuo The residue was purified on silica gel 0-50% EtOAc/Hexanes to provide benzyl ((6-chloro-3-(1,1-difluoroethyl)-1-trityl-1H-pyrazolo[4,3-c]pyridin-4-yl)methyl) carbonate. MS ESI calc'd. for $C_{36}H_{29}ClF_2N_3O_3$ [M+1]⁺ 624. found 624.

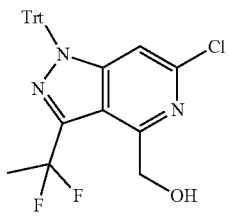

Step 3: (6-chloro-3-(1,1-difluoroethyl)-1-trityl-1H-pyrazolo[4,3-c]pyridin-4-yl)methanol To the solution of benzyl ((6-chloro-3-(1,1-difluoroethyl)-1-trityl-1H-pyrazolo[4,3-c]pyridin-4-yl)methyl) carbonate (280 mg, 0.449 mmol) in MeOH (8.0 ml) under an atmosphere of hydrogen gas (at 1 atm) was added palladium hydroxide on carbon (63.0 mg, 0.090 mmol). The resulting reaction mixture was allowed to stir at ambient temperature for 18 hrs. The solution was filtered through celite and concentrated in vacuo. The residue was purified on silica gel 0-50% EtOAc/Hexanes to provide (6-chloro-3-(1,1-difluoroethyl)-1-trityl-1H-pyrazolo[4,3-c]pyridin-4-yl)methanol. MS ESI calc'd. for $C_{28}H_{23}ClF_2N_3O$ [M+1]⁺490. found 490.

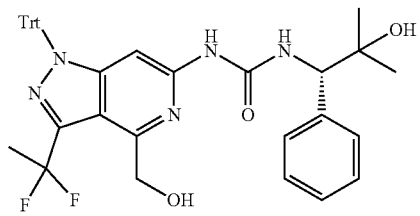

Step 4: (S)-1-(3-(1,1-difluoroethyl)-4-(hydroxymethyl)-1-trityl-1H-pyrazolo[4,3-c]pyridin-6-yl)-3-(2-hydroxy-2-methyl-1-phenylpropyl)urea (6-chloro-3-(1,1-difluoroethyl)-1-trityl-1H-pyrazolo[4,3-c]pyridin-4-yl)methanol (80 mg, 0.163 mmol), (S)-1-(2-hydroxy-2-methyl-1-phenylpropyl)urea (Intermediate 60A, 68.0 mg, 0.327 mmol), cesium carbonate (160 mg, 0.490 mmol), BrettPhos Palladacycle (13.04 mg, 0.016 mmol) and BrettPhos (8.76 mg, 0.016 mmol) were taken up in dioxane (3.0 ml) in a 20 mL microwave vial. The vial was evacuated and back-filled with N₂ gas three times before heating to 90° C. for 24 hrs. The reaction mixture was filtered though celite and concentrated. The products were used directly in the next step without purification. MS ESI calc'd. for $C_{39}H_{38}F_2N_5O_3$[M+1]⁺ 662. found 662.

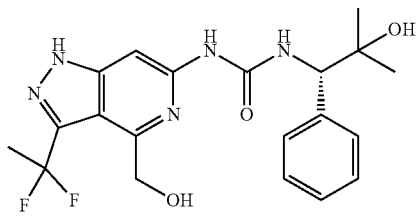 [SMILES: CC(F)(F)c1n[nH]c2cc(NC(=O)N[C@@H](c3ccccc3)C(C)(C)O)nc(CO)c12]

Step 5: (S)-1-(3-(1,1-difluoroethyl)-4-(hydroxymethyl)-1H-pyrazolo[4,3-c]pyridin-6-yl)-3-(2-hydroxy-2-methyl-1-phenylpropyl)urea (S)-1-(3-(1,1-difluoroethyl)-4-(hydroxymethyl)-1H-pyrazolo[4,3-c]pyridin-6-yl)-3-(2-hydroxy-2-methyl-1-phenylpropyl)urea was prepared using the same procedure as (R)-1-(3,4-bis(hydroxymethyl)-1H-pyrazolo[4,3-c]pyridin-6-yl)-3-(1-phenylethyl)urea (Example 25, Step 4). MS ESI calc'd. for $C_{20}H_{24}F_2N_5O_3$[M+1]⁺ 420. found 420. ¹H NMR (500 MHz, DMSO-d₆) δ 13.76 (brs, 1H), 9.86 (brs, 1H), 7.43-7.13 (m, 6H), 4.99-4.87 (m, 2H), 4.61 (d, J=8.9, 1H), 2.15 (s, 3H), 1.19 (s, 3H), 0.99 (s, 3H).

The following example was prepared according to scheme 11.

Example 29

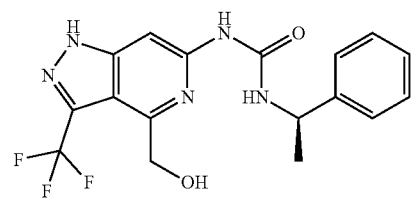 [SMILES: C[C@@H](NC(=O)Nc1cc2[nH]nc(C(F)(F)F)c2c(CO)n1)c1ccccc1]

(R)-1-(4-(hydroxymethyl)-3-(trifluoromethyl)-1H-pyrazolo[4,3-c]pyridin-6-yl)-3-(1-phenylethyl)urea

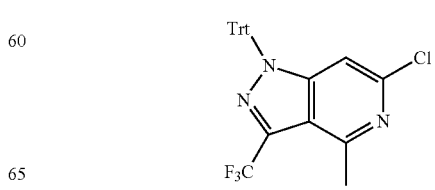

Step 1: 6-chloro-4-methyl-3-(trifluoromethyl)-1-trityl-1H-pyrazolo[4,3-c]pyridine 6-chloro-3-iodo-4-methyl-1-trityl-1H-pyrazolo[4,3-c]pyridine (Intermediate 1A, 370 mg, 0.691 mmol) and trifluoromethyl(1,10-phenanthroline)copper (324 mg, 1.036 mmol) were added to an oven-dried 4 mL microwave tube equipped with magnetic stir bar and evacuated under nitrogen gas. DMF (2.8 ml) was added and the reaction was heated to 50° C. overnight. The reaction temperature was raised to 90° C. and stirred for an additional 24 hours. The reaction was diluted with 2 mL DCM, filtered through a syringe filter and the solvents were evaporated in vacuo. The residue was purified on silica gel, 5-20% EtOAc/hexanes to provide 6-chloro-4-methyl-3-(trifluoromethyl)-1-trityl-1H-pyrazolo[4,3-c]pyridine. MS ESI calc'd. for $C_{27}H_{20}ClF_3N_3$ [M+1]$^+$ 478. found [M+Na] 500.

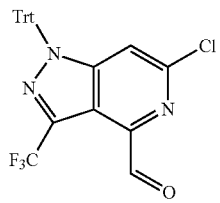

Step 2: Step 1: 6-chloro-4-methyl-3-(trifluoromethyl)-1-trityl-1H-pyrazolo[4,3-c]pyridine 6-chloro-4-methyl-3-(trifluoromethyl)-1-trityl-1H-pyrazolo[4,3-c]pyridine (130 mg, 0.272 mmol) and selenium dioxide (91 mg, 0.816 mmol) were added to a 2 mL microwave tube, charged with 1,4-dioxane (2.0 mL) and heated to 100° C. over the weekend. The reaction was filtered through a syringe filter and the solvents were removed in vacuo. The residue was purified on silica gel, 0-10% EtOAc/DCM to provide 6-chloro-3-(trifluoromethyl)-1-trityl-1H-pyrazolo[4,3-c]pyridine-4-carbaldehyde. $^1$H NMR (500 MHz, CDCl$_3$) δ 10.19 (s, 1H), 7.41-7.27 (m, 10H), 7.09 (m, 5H), 6.45 (s, 1H).

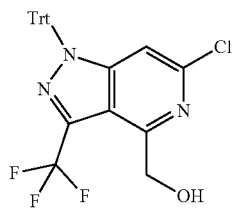

Step 3: (6-chloro-3-(trifluoromethyl)-1-trityl-1H-pyrazolo[4,3-c]pyridin-4-yl)methanol 6-chloro-3-(trifluoromethyl)-1-trityl-1H-pyrazolo[4,3-c]pyridine-4-carbaldehyde (122 mg, 0.248 mmol) was taken up in DCM (1250 μl) and MeOH (1000 μl). The solution was treated with sodium borohydride (14.07 mg, 0.372 mmol) and the mixture was allowed to stir at room temperature for 1 hour. The reaction was partitioned between DCM and saturated aqueous brine. The aqeous layer was extracted with DCM (×2), combined oraganics were dried over Na$_2$SO$_4$ and solvent was evaporated in vacuo affording (6-chloro-3-(trifluoromethyl)-1-trityl-1H-pyrazolo[4,3-c]pyridin-4-yl)methanol. Material was used with no further purification. MS ESI calc'd. for $C_{27}H_{20}ClF_3N_3O$ [M+1]$^+$ 494. found 494.

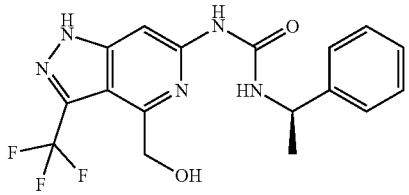 [SMILES: C[C@@H](NC(=O)Nc1cc2[nH]nc(C(F)(F)F)c2c(CO)n1)c1ccccc1]

Step 4: (R)-1-(4-(hydroxymethyl)-3-(trifluoromethyl)-1H-pyrazolo[4,3-c]pyridin-6-yl)-3-(1-phenylethyl)urea (6-chloro-3-(trifluoromethyl)-1-trityl-1H-pyrazolo[4,3-c]pyridin-4-yl)methanol (96.0 mg, 0.194 mmol), (R)-1-(1-phenylethyl)urea (63.8 mg, 0.389 mmol), cesium carbonate (158 mg, 0.486 mmol), BrettPhos-precatalyst (9.32 mg, 0.012 mmol), BrettPhos (6.26 mg, 0.012 mmol) and Dioxane (1593 μl) were charge in a 5 mL pressure vessel. The system was degassed and stirred at 100° C. for 3 hr. Room temperature was attained and additional (R)-1-(1-phenylethyl)urea (23.94 mg, 0.146 mmol), BrettPhos (6.26 mg, 0.012 mmol) and BrettPhos Precatalyst (9.32 mg, 0.012 mmol) were added to the reaction. The system was degassed and backfilled with nitrogen gas and was allowed to stir at 100° C. for 10 mins. Room temperature was attained then the reaction mixture was diluted w/ EtOAc, filtered, and evaporated in vacuo affording an oil. The oil was treated with a solution of TFA (1.8 ml, 23.32 mmol) and triethylsilane (78 μl, 0.486 mmol) and stirred for 3 hrs at 40° C. The solvent was evaporated in vacuo and the oil was diluted with DMSO, filtered, and purified by mass-triggered reverse-phase HPLC. The fractions containing pure product were collected and then freebased using an PL-HCO$_3$ cartridge to afford (R)-1-(4-(hydroxymethyl)-3-(trifluoromethyl)-1H-pyrazolo[4,3-c]pyridin-6-yl)-3-(1-phenylethyl)urea. MS ESI calc'd. for $C_{17}H_{17}F_3N_5O_2$ [M+1]$^+$ 380. found 380. $^1$H NMR (500 MHz, DMSO-d$_6$) δ 9.22 (s, 1H), 8.42 (bs, 1H), 7.50 (s, 1H), 7.33 (m, J=7.5, 4H), 7.21 (m, 1H), 5.30 (s, 1H), 4.88 (dd, J=7.2, 14.5, 1H), 4.79 (d, J=3.7, 2H), 1.40 (d, J=6.9, 3H)

Assays

Active Human ERK2 (hERK2) Activity Assay:

Activated ERK2 activity was determined in an IMAP-FP assay (Molecular Devices). Using this assay format, the potency (IC$_{50}$) of each compound was determined from a 10 point (1:3 serial dilution, 3 μM starting compound concentration) titration curve using the following outlined procedure. To each well of a black Corning 384-well plate (Corning Catalog #3575), 7.5 nL of compound (3333 fold dilution in final assay volume of 25 μL) was dispensed, followed by the addition of 15 μL of kinase buffer (tween containing kinase buffer, Molecular Devices) containing 0.0364 ng/mL (0.833 nM) of phosphorylated active hERK2 enzyme. Following a 15 minute compound & enzyme incubation, each reaction was initiated by the addition of 10 μL kinase buffer containing 2.45 μM ERK2 IMAP substrate peptides and 75 μM ATP. The final reaction in each well of 25 μL consists of 0.5 nM hERK2, 900 nM unlabeled peptide, 80 nM labeled-peptide, and 30 μM ATP. Phosphorylation reactions were allowed to proceed for 60 minutes and were immediately quenched by the addition of 60 μL IMAP detection beads (1:1000 dilutions) in IMAP binding buffer (Molecular Devices) with 24 mM NaCl. Plates were read on EnVision reader after 60 minutes binding equilibration using Fluorescence Polarization protocol (Perkin Elmer).

Assay Data

The ERK2 $IC_{50}$ in nanomolar (nM) for the compounds of Examples 1 to 29 is in Table 6.

TABLE 6

| Ex | $IC_{50}$ |
|---|---|
| 1 | 0.37 |
| 2 | 1.24 |
| 3 | 0.92 |
| 4 | 0.39 |
| 5 | 0.72 |
| 6 | 4.34 |
| 7 | 0.83 |
| 8 | 0.91 |
| 9 | 0.75 |
| 10 | 0.66 |
| 11 | 0.45 |
| 12 | 1.64 |
| 13 | 0.31 |
| 14 | 0.39 |
| 15 | 0.29 |
| 16 | 0.23 |
| 17 | 8.64 |
| 18 | 0.37 |
| 19 | 0.53 |
| 20 | 1.13 |
| 21 | 0.61 |
| 22 | 0.75 |
| 23 | 0.49 |
| 24 | 1.25 |
| 25 | 1.85 |
| 26 | 12.73 |
| 27 | 5.52 |
| 28 | 14.09 |
| 29 | 13.25 |

While the present invention has been described in conjunction with the specific examples set forth above, many alternatives, modifications and variations thereof will be apparent to those of ordinary skill in the art. All such alternatives, modifications and variations are intended to fall within the spirit and scope of the present invention.

What is claimed is:

1. A compound of formula (1):

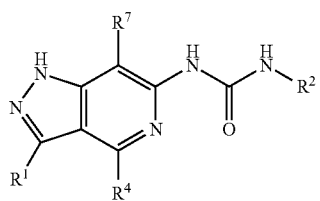

(1.0)

or a pharmaceutically acceptable salt thereof, wherein:

$R^1$ is selected from the group consisting of: H, halo, —CN, $(C_1$-$C_6)$alkyl, substituted $(C_1$-$C_6)$alkyl, $(C_2$-$C_6)$alkenyl, $(C_3$-$C_6)$cycloalkyl, substituted $(C_3$-$C_6)$cycloalkyl, heteroaryl, substituted heteroaryl, heterocycloalkyl-, substituted heterocycloalkenyl, —$(C_1$-$C_6)$alkyl-O—$(C_1$-$C_6)$alkyl, —$(C_1$-$C_6)$alkyl-O-(substituted $(C_1$-$C_6)$ alkyl), -(substituted $(C_1$-$C_6)$ alkyl)-O-(substituted $(C_1$-$C_6)$ alkyl), -(substituted $(C_1$-$C_6)$alkyl)-O—$(C_1$-$C_6)$ alkyl), aryl, substituted aryl, —C(O)($C_1$-$C_6$alkyl), —C(O)(substituted $(C_1$-$C_6)$alkyl), —C(O)O($C_1$-$C_6)$alkyl, —C(O)NH($C_1$-$C_6)$alkyl, —C(O)N(($C_1$-$C_6)$alkyl)$_2$ wherein each alkyl is independently selected, —C(O)—$(C_1$-$C_6)$ alkyl-C(O)—$(C_1$-$C_6)$alkyl, —$(C_1$-$C_4)$alkyl-C(O)—O—$(C_1$-$C_4)$alkyl, —C(O)NH—$(C_1$-$C_2)$alkyl-fused heteroarylheteroaryl, —C(O)NH—$(C_1$-$C_2)$alkyl-(substituted fused heteroarylheteroaryl), —C(O)NH—$(C_1$-$C_2)$alkyl-$(C_3$-$C_6)$cycloalkyl-N$(R^8)_2$, —C(O)NH—$(C_1$-$C_2)$alkyl-(substituted $(C_3$-$C_6)$cycloalkyl)-N$(R^8)_2$, —C(O)NH—$(C_1$-$C_2)$alkylheterocycloalkyl, —C(O)NH—$(C_1$-$C_2)$alkyl(substituted heterocycloalkyl), —C(O)NH—$(C_1$-$C_2)$alkylheteroaryl, —C(O)NH—$(C_1$-$C_2)$alkyl(substituted heteroaryl), —C(O)NH—$(C_1$-$C_6)$alkyl-$(C_3$-$C_6)$cycloalkyl, —C(O)NH—$(C_1$-$C_6)$alkyl-(substituted $(C_3$-$C_6)$cycloalkyl), —C(O)NH—$(C_1$-$C_6)$alkyl-O—$(C_1$-$C_6)$alkyl, —C(O)NH—$(C_1$-$C_6)$alkylheterocycloalkyl, —C(O)NH—$(C_1$-$C_6)$alkyl(substituted heterocycloalkyl), —C(O)NH—$(C_1$-$C_2)$-(bridged multicyclic cycloalkyl), —C(O)NH—$(C_1$-$C_2)$-(bridged tricyclic cycloalkyl), —C(O)NH—$(C_1$-$C_2)$-(substituted bridged multicyclic cycloalkyl), —C(O)NH—$(C_1$-$C_2)$-(substituted bridged tricyclic cycloalkyl), —C(O)-heterocycloalkyl-S—$(C_1$-$C_6)$ alkyl, —C(O)-(substituted heterocycloalkyl-S—$(C_1$-$C_6)$alkyl, —C(O)-heterocycloalkyl, —C(O)-(substituted heterocycloalkyl), fused arylheteroaryl, fused (substituted arylheteroaryl), fused heteroarylheteroaryl, fused (substituted heteroarylheteroaryl), —$(C_1$-$C_4)$alkyl-S(O)$_2$—$(C_1$-$C_6)$alkyl, and —$(C_1$-$C_4)$alkyl-NH—$(C_1$-$C_6)$alkyl;

and wherein said substituted $R^1$ groups, other than said substituted $(C_1$-$C_6)$alkyl, are substituted with 1 to 3 substituents independently selected from the group consisting of: —$(C_1$-$C_6)$alkyl, —$(C_1$-$C_6)$alkoxy, halo, CN, —OH, —$CF_3$, =O, —$NH_2$, —NH($C_1$-$C_6)$alkyl, —S(O)$_2$($C_1$-$C_6)$alkyl, —$(C_3$-$C_6)$cycloalkyl, —(($C_1$-$C_6)$alkyl)OH, —$(C_3$-$C_6)$cycloalkyl-S—$(C_3$-$C_6)$cycloalkyl, —N(($C_1$-$C_6)$alkyl)$_2$ wherein each alkyl is independently selected, —C(O)O—$(C_1$-$C_6)$alkyl, —C(O)OH, —$OCF_3$, —C(O)NH($C_1$-$C_6)$alkyl, heteroaryl, —$(C_1$-$C_6)$alkyl)-O—$(C_1$-$C_6)$ alkyl, fused heteroarylaryl-, heterocycloalkyl, and heterocycloalkenyl;

and wherein the substituted $(C_1$-$C_6)$alkyl $R^1$ group, and the substituted $(C_1$-$C_6)$alkyl moieties of the substituted $R^1$ groups comprising said substituted $(C_1$-$C_6)$ alkyl moieties, are substituted with 1 to 3 substituents independently selected from the group consisting of: —$(C_1$-$C_6)$alkoxy, halo, CN, —OH, =O, —$CF_3$, —$NH_2$, —NH($C_1$-$C_6)$alkyl, —S(O)$_2$($C_1$-$C_6)$alkyl, fused heteroarylaryl-, heterocycloalkyl, and heterocycloalkenyl;

$R^2$ is selected from the group consisting of: H, $(C_6$-$C_{10})$aryl-$(C_1$-$C_4$alkyl)-heterocycloalkyl-, —$(C_1$-$C_6$alkyl), —$(C_1$-$C_6$alkyl)-O—$(C_1$-$C_6$alkyl), —$(C_1$-$C_6$alkyl)-heterocycloalkyl-$(C_6$-$C_{10}$aryl), —$(C_1$-$C_4$alkyl)($C_6$-$C_{10})$aryl, —$(C_1$-$C_3$alkyl)heteroaryl, —$(C_3$-$C_6$cycloalkyl)-$(C_6$-$C_{10}$aryl), -heterocycloalkyl-$(C_6$-$C_{10}$aryl); and wherein said aryl, heterocycloalkyl, heteroaryl, and cycloalkyl moieties of said $R^2$ groups are optionally substituted with 1-3 substituents independently selected from the group consisting of: halo, —O—$(C_1$-$C_6$alkyl), —OH, —$CF_3$, and —$(C_1$-$C_6$alkyl); and wherein said alkyl moieties of said R² groups are optionally substituted with 1-3 substituents independently selected from the group consisting of: halo, —O—($C_1$-$C_6$alkyl), —O-(substituted $C_1$-$C_6$alkyl), —OH and —$CF_3$, and wherein said substituted $C_1$-$C_6$alkyl moiety of said —O-(substituted $C_1$-$C_6$alkyl) group is substituted with 1-3 independently selected halo atoms;

R³ is selected from the group consisting of: H, ($C_1$-$C_6$) alkyl, or substituted ($C_1$-$C_6$)alkyl, wherein said substituted ($C_1$-$C_6$)alkyl is substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —$S(O)_2$($C_1$-$C_6$)alkyl, fused heteroarylaryl-, heterocycloalkyl, and heterocycloalkenyl;

R⁴ is selected from the group consisting of: —NHR³, —OR⁵, —CH(OH)R⁶, halo, —($C_1$ to $C_6$alkyl), —($C_3$-$C_6$ cycloalkyl), hydroxy substituted —($C_1$-$C_6$alkyl), —($C_1$-$C_6$alkyl)-O—($C_1$-$C_6$alkyl), —($C_1$-$C_6$alkyl)-N($C_1$-$C_6$alkyl)₂ wherein each alkyl is independently selected, and —($C_1$-$C_6$alkyl)-heterocycloalkyl;

R⁵ is selected from the group consisting of: H, —($C_1$-$C_6$alkyl), and -(substituted $C_1$-$C_6$alkyl), wherein said substituted alkyl is substituted with 1 to 3 substituents independently selected from the group consisting of: —($C_1$-$C_6$)alkoxy, halo, CN, —OH, =O, —$CF_3$, —$NH_2$, —NH($C_1$-$C_6$)alkyl, —$S(O)_2$($C_1$-$C_6$) alkyl, fused heteroarylaryl-, heterocycloalkyl, and heterocycloalkenyl;

R⁶ is selected from the group consisting of: —($C_1$-$C_6$alkyl) and —($C_3$-$C_6$ cycloalkyl);

R⁷ is selected from the group consisting of: H, halo, —($C_1$ to $C_6$alkyl), —($C_3$-$C_6$ cycloalkyl), hydroxy substituted —($C_1$-$C_6$alkyl); and each R⁸ is independently selected from the group consisting of: —($C_1$-$C_6$)alkyl.

2. The compound of claim 1 wherein R¹ is selected from the group consisting of: methylpyridyl, fluoropyridyl, —$CF_3$, —$C(O)CH_3$, —$CH_2OH$, cyclopropyl, —$CHF_2$, —CH(OH)$CH_3$, fluorophenyl, cyanopyridyl, and cyanophenyl.

3. The compound of claim 1 wherein R² is selected from the group consisting of: —CH($CH_3$)phenyl, —CH($CH_2OCHF_2$)-phenyl, —CHC($CH_3$)$_2$OH-phenyl, —CHC($CH_3$)$_2$OH—F-phenyl, —CHC($CH_3$)$_2$OH-phenyl, —CHCH($CH_3$)(OH)—F-phenyl, —CHCH($CH_3$)(OH)-phenyl, and —CHC($CH_3$)$_2$OH-phenyl.

4. The compound of claim 1 wherein R¹ is selected from the group consisting of: methylpyridyl, fluoropyridyl, —$CF_3$, —$C(O)CH_3$, —$CH_2OH$, cyclopropyl, —$CHF_2$, —CH(OH)$CH_3$, fluorophenyl, cyanopyridyl, and cyanophenyl.

5. The compound of claim 1 wherein R¹ is selected from the group consisting of: —$CF_3$, —$C(O)CH_3$, —$CH_2OH$, cyclopropyl, —$CH_2F$, and —CH(OH)$CH_3$.

6. The compound of claim 1 wherein R⁴ is selected from the group consisting of: —NHR³, —OR⁵, —CH(OH)R⁶, —($C_1$ to $C_2$alkyl), hydroxy substituted —($C_1$-$C_2$alkyl), and —($C_1$-$C_2$alkyl)-O—($C_1$-$C_2$alkyl).

7. The compound of claim 1 wherein R¹ is selected from the group consisting of: methylpyridyl, fluoropyridyl, —$CF_3$, —$C(O)CH_3$, —$CH_2OH$, cyclopropyl, —$CHF_2$, —CH(OH)$CH_3$, fluorophenyl, cyanopyridyl, and cyanophenyl; and R⁴ is selected from the group consisting of: —NHR₃, —OR', —CH(OH)R⁶, —($C_1$ to $C_2$alkyl), hydroxy substituted —($C_1$-$C_2$alkyl), and —($C_1$-$C_2$alkyl)-O—($C_1$-$C_2$alkyl).

8. The compound of claim 1 wherein R⁷ is H.
9. The compound of claim 7 wherein R⁷ is H.
10. A compound selected from the group consisting of
(R)-1-(4-Methyl-3-(2-methylpyridin-4-yl)-1H-pyrazolo[4,3-c]pyridin-6-yl)-3-(1-phenylethyl)urea,
1-[3-(2-fluoropyridin-4-yl)-4-methyl-1H-pyrazolo[4,3-c]pyridin-6-yl]-3-[(1R)-1-phenylethyl]urea,
(R)-1-(3-(2-fluoropyridin-4-yl)-4-(hydroxymethyl)-1H-pyrazolo[4,3-c]pyridin-6-yl)-3-(1-phenylethyl)urea,
(R)-1-(4-(hydroxymethyl)-3-(2-methylpyridin-4-yl)-1H-pyrazolo[4,3-c]pyridin-6-yl)-3-(1-phenylethyl)urea,
(R)-1-(3-cyclopropyl-4-(hydroxymethyl)-1H-pyrazolo[4,3-c]pyridin-6-yl)-3-(1-phenylethyl)urea,
1-[3-cyclopropyl-4-(hydroxymethyl)-1H-pyrazolo[4,3-c]pyridin-6-yl]-3-[(1S)-2-hydroxy-2-methyl-1-phenylpropyl]urea,
1-[3-cyclopropyl-4-(hydroxymethyl)-1H-pyrazolo[4,3-c]pyridin-6-yl]-3-[(1S)-1-(4-fluorophenyl)-2-hydroxy-2-methylpropyl]urea,
1-[3-cyclopropyl-4-(hydroxymethyl)-1H-pyrazolo[4,3-c]pyridin-6-yl]-3-[(1S,2R)-1-(4-fluorophenyl)-2-hydroxypropyl]urea,
1-[3-cyclopropyl-4-(hydroxymethyl)-1H-pyrazolo[4,3-c]pyridin-6-yl]-3-[(1S,2R)-2-hydroxy-1-phenylpropyl]urea,
1-[(1S)-2-(difluoromethoxy)-1-phenylethyl]-3-[4-(hydroxymethyl)-3-(2-methylpyridin-4-yl)-1H-pyrazolo[4,3-c]pyridin-6-yl]urea,
1-[3-(4-fluorophenyl)-4-(hydroxymethyl)-1H-pyrazolo[4,3-c]pyridin-6-yl]-3-[(1R)-1-phenylethyl]urea,
1-[3-(2-cyanopyridin-4-yl)-4-(hydroxymethyl)-1H-pyrazolo[4,3-c]pyridin-6-yl]-3-[(1R)-1-phenylethyl]urea,
1-[3-(4-fluorophenyl)-4-(hydroxymethyl)-1H-pyrazolo[4,3-c]pyridin-6-yl]-3-[(1S)-2-hydroxy-2-methyl-1-phenylpropyl]urea,
1-[3-(4-fluorophenyl)-4-(hydroxymethyl)-1H-pyrazolo[4,3-c]pyridin-6-yl]-3-[(1S,2R)-1-(4-fluorophenyl)-2-hydroxypropyl]urea,
1-[(1S)-1-(4-fluorophenyl)-2-hydroxy-2-methylpropyl]-3-[3-(4-fluorophenyl)-4-(hydroxymethyl)-1H-pyrazolo[4,3-c]pyridin-6-yl]urea,
1-[3-(4-fluorophenyl)-4-(hydroxymethyl)-1H-pyrazolo[4,3-c]pyridin-6-yl]-3-[(1S,2R)-2-hydroxy-1-phenylpropyl]urea,
1-[(1R)-2,2-dimethyl-1-phenylpropyl]-3-[3-(4-fluorophenyl)-4-(hydroxymethyl)-1H-pyrazolo[4,3-c]pyridin-6-yl]urea,
1-[(1S)-2-hydroxy-2-methyl-1-phenylpropyl]-3-[4-(hydroxymethyl)-3-phenyl-1H-pyrazolo[4,3-c]pyridin-6-yl]urea,
1-[3-(4-cyanophenyl)-4-(hydroxymethyl)-1H-pyrazolo[4,3-c]pyridin-6-yl]-3-[(1S)-2-hydroxy-2-methyl-1-phenylpropyl]urea,
(R)-1-(4-(Methoxymethyl)-3-(2-methylpyridin-4-yl)-1H-pyrazolo[4,3-c]pyridin-6-yl)-3-(1-phenylethyl)urea,
(S)-1-(3-(difluoromethyl)-4-methyl-1H-pyrazolo[4,3-c]pyridin-6-yl)-3-(2-hydroxy-2-methyl-1-phenylpropyl)urea,
(S)-1-(3-(difluoromethyl)-4-(hydroxymethyl)-1H-pyrazolo[4,3-c]pyridin-6-yl)-3-(2-hydroxy-2-methyl-1-phenylpropyl)urea,
1-[3-(difluoromethyl)-4-(hydroxymethyl)-1H-pyrazolo[4,3-c]pyridin-6-yl]-3-[(1S)-1-(4-fluorophenyl)-2-hydroxy-2-methylpropyl]urea,
1-[3-(difluoromethyl)-4-(hydroxymethyl)-1H-pyrazolo[4,3-c]pyridin-6-yl]-3-[(1R)-1-phenylethyl]urea, (R)-1-(3,4-bis(hydroxymethyl)-1H-pyrazolo[4,3-c]pyridin-6-yl)-3-(1-phenylethyl)urea, (R)-1-(3-acetyl-4-(hydroxymethyl)-1H-pyrazolo[4,3-c]pyridin-6-yl)-3-(1-phenylethyl)urea, 1-(3-(1-hydroxyethyl)-4-(hydroxymethyl)-1H-pyrazolo[4,3-c]pyridin-6-yl)-3-((R)-1-phenylethyl)urea, (S)-1-(3-(1,1-difluoroethyl)-4-(hydroxymethyl)-1H-pyrazolo[4,3-c]pyridin-6-yl)-3-(2-hydroxy-2-methyl-1-phenylpropyl)urea, or (R)-1-(4-(hydroxymethyl)-3-(trifluoromethyl)-1H-pyrazolo[4,3-c]pyridin-6-yl)-3-(1-phenylethyl)urea, or a pharmaceutically acceptable salt thereof.

11. A pharmaceutical composition comprising an effective amount of a compound of claim 1 and a pharmaceutically acceptable carrier.

12. A pharmaceutical composition comprising an effective amount of a compound of claim 10, and a pharmaceutically acceptable carrier.

13. A method of treating cancer in a patient in need of such treatment, said method comprising administering to said patient an effective amount of at least one compound of claim 1.

14. The method of claim 13 wherein said cancer is colorectal cancer or melanoma.

15. A method of treating cancer in a patient in need of such treatment, said method comprising administering to said patient an effective amount of at least one compound of claim 1 in combination with an effective amount of at least one chemotherapeutic agent.

\* \* \* \* \*